US010800834B2

(12) United States Patent
Kaumaya

(10) Patent No.: US 10,800,834 B2
(45) Date of Patent: Oct. 13, 2020

(54) HER-1, HER-3 AND IGF-1R COMPOSITIONS AND USES THEREOF

(71) Applicant: OHIO STATE INNOVATION FOUNDATION, Columbus, OH (US)

(72) Inventor: Pravin T. P. Kaumaya, Westerville, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/292,032

(22) Filed: Mar. 4, 2019

(65) Prior Publication Data

US 2019/0185542 A1 Jun. 20, 2019

Related U.S. Application Data

(62) Division of application No. 14/770,335, filed as application No. PCT/US2014/018354 on Feb. 25, 2014, now Pat. No. 10,221,230.

(60) Provisional application No. 61/768,881, filed on Feb. 25, 2013, provisional application No. 61/778,766, filed on Mar. 13, 2013.

(51) Int. Cl.
| | |
|---|---|
| *C07K 1/00* | (2006.01) |
| *C07K 14/72* | (2006.01) |
| *A61K 9/00* | (2006.01) |
| *A61K 39/00* | (2006.01) |
| *C07K 16/28* | (2006.01) |
| *C12Q 1/6883* | (2018.01) |
| *C07K 16/32* | (2006.01) |
| *A61K 47/65* | (2017.01) |
| *A61K 47/64* | (2017.01) |
| *A61K 47/34* | (2017.01) |
| *A61K 47/44* | (2017.01) |
| *C07K 14/435* | (2006.01) |
| *C07K 14/475* | (2006.01) |
| *C07K 14/82* | (2006.01) |
| *A61K 38/00* | (2006.01) |

(52) U.S. Cl.
CPC .......... *C07K 14/72* (2013.01); *A61K 9/0019* (2013.01); *A61K 39/0005* (2013.01); *A61K 39/0011* (2013.01); *A61K 47/34* (2013.01); *A61K 47/44* (2013.01); *A61K 47/646* (2017.08); *A61K 47/65* (2017.08); *C07K 14/435* (2013.01); *C07K 14/475* (2013.01); *C07K 14/721* (2013.01); *C07K 14/82* (2013.01); *C07K 16/2863* (2013.01); *C07K 16/32* (2013.01); *C12Q 1/6883* (2013.01); *A61K 38/00* (2013.01); *A61K 2039/505* (2013.01); *A61K 2039/545* (2013.01); *A61K 2039/5555* (2013.01); *A61K 2039/55566* (2013.01); *A61K 2039/585* (2013.01); *A61K 2039/6075* (2013.01); *A61K 2039/627* (2013.01); *A61K 2039/70* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 7,060,284 | B1 | 6/2006 | Kaumaya et al. |
| 7,250,403 | B2 | 7/2007 | Van Nest et al. |
| 7,666,430 | B2 | 2/2010 | Kaumaya |
| 7,691,369 | B2 | 4/2010 | Kataoka |
| 8,080,253 | B2 | 12/2011 | Kaumaya et al. |
| 8,110,657 | B2 | 2/2012 | Kaumaya |
| 8,470,333 | B2 | 6/2013 | Kaumaya |
| 2010/0234283 | A1 | 9/2010 | Kaumaya |
| 2011/0086055 | A1 | 4/2011 | Kaumaya |
| 2012/0121626 | A1 | 5/2012 | Kaumaya et al. |
| 2012/0201841 | A1 | 8/2012 | Kaumaya |
| 2013/0195870 | A1 | 8/2013 | Jaiswal |
| 2013/0216564 | A1 | 8/2013 | Pravin |
| 2013/0230546 | A1 | 9/2013 | Kaumaya et al. |
| 2014/0010831 | A1 | 1/2014 | Kaumaya |

FOREIGN PATENT DOCUMENTS

WO 2012019024 2/2012

OTHER PUBLICATIONS

Adams TE, Epa VC, Garrett TP, Ward CW. Structure and function of the type 1 insulinlike growth factor receptor. Cell. Mol. Life Sci. 57, 1050-1093 (2000).

Agus DB, Akita RW, Fox WD et al. Targeting ligand-activated ErbB2 signaling inhibits breast and prostate tumor growth. Cancer Cell 2, 127-137 (2002).

Agus DB, Gordon MS, Taylor C et al. Phase I clinical study of pertuzumab, a novel HER dimerization inhibitor, in patients with advanced cancer. J. Clin. Oncol 23(11), 2534-2543 (2005).

(Continued)

*Primary Examiner* — Shulamith H Shafer
(74) *Attorney, Agent, or Firm* — Meunier Carlin & Curfman LLC

(57) ABSTRACT

Provided herein are HER-3, HER-1 and IGF-1R B cell epitopes, peptide mimics, chimeric peptides and multivalent peptides. In some embodiments, the chimeric peptides include one or more HER-3, HER-1 and/or IGF-1R B cell epitopes, a linker, and a T helper cell (Th cell) epitope. Pharmaceutical compositions are also provided that contain one or more HER-3, HER-1 and/or IGF-1R chimeric peptides, and optionally, one or more HER-2 chimeric peptides and/or VEGF peptides. Also included herein are methods of treating a cancer using the HER-3, HER-1 and IGF-1R B cell epitopes, chimeric peptides and multivalent peptides.

8 Claims, 40 Drawing Sheets

Specification includes a Sequence Listing.

(56) References Cited

OTHER PUBLICATIONS

Agus DB, Sweeney CJ, Morris MJ et al. Efficacy and safety of single-agent pertuzumab rhuMAb 2C4), a human epidermal growth factor receptor dimerization inhibitor, in castration resistant prostate cancer after progression from taxane-based therapy. J. Clin. Oncol. 25, 675-681 (2007).
Alaoui-Jamali MA, Yen L, Benlimame N et al. Differential regulation of tumor angiogenesis by distinct ErbB homo- and heterodimers. Mol. Biol. Cell 13, 4029-4044 (2002).
Allen SD, Rawale SV, Whitacre CC, Kaumaya PT. Therapeutic peptidomimetic strategies for autoimmune diseases: costimulation blockade. J. Pept. Res. 65, 591-604 (2005).
Allen SD, Garrert JT, Rawale SV et al. Peptide vaccines of the HER-2/neu dimerization loop are effective in inhibiting mammary tumor growth in vivo. J. Immunol. 179, 472-482 (2007).
Amici A, Venanzi FM, Concetti A. Genetic immunization against neu/erbB2 ttansgenic breast cancer. Cancer Immunol. Immunother. 47, 183-190 (1998).
Amler, L.C., HER3 mRNA as a predictive biomarker in anticancer therapy. Expert Opin Biol Ther, 2010. 10(9): p. 1343-55.
An Y, Cai Y, Guan Y, Cai L, Yang Y, Feng X, Zheng J: Inhibitory effect of small interfering RNA targeting insulin-like growth factor-I receptor in ovarian cancer OVCAR3 cells. Cancer Biother Radiopharm, 25(5):545-552.
Angelucci A. Targeting ERBB receptors to inhibit metastasis: old hopes and new certainties. Curr. Cancer Drug Targets 9, 1-18 (2009).
Anghelina M, Schmeisser A, Krishnan P, Moldovan L, Strasser RH, Moldovan NI. Migration of monocytes/macrophages in vitro and in vivo is accompanied by MMP12-dependent tunnels formation, and by neo-vascularization, Cold Spring Harbor Symp. in Quant. Biol., 2002, LXVII: 209-215.
Anghelina M, Krishnan P, Moldovan L, Moldovan NI. Monocytes and macrophages form branched cell columns in matrigel: implications for a role in neovascularization. Stem Cells Dev. 13, 665-676 (2004).
Anghelina M, Moldovan L, Moldovan NI. Preferential activity of Tie2 promoter in arteriolar endothelium. J. Cell. Mol. Med. 2005, 9: 113-121.
Anghelina M, Krishnan P, Moldovan L, Moldovan NI. Monocytes/macrophages cooperate with progenitor cells during neovascularization and tissue repair: conversion of cell columns into fibrovascular bundles. Am. J. Pathol. 168, 529-541 (2006).
Anghelina M, Moldovan L, Zabuala T, Ostrowski M, Moldovan NI. A subpopulation of peritoneal macrophages form capillarylike lumens and branching patterns in vitro. J. Cell. Mol. Med. 2006, 10:708-15.
Arteaga CL, Moulder SL, Yakes FM. HER (erbB) tyrosine kinase inhibitors in the treatment of breast cancer. Semin. Oncol. 29, 4-10 (2002).
Arteaga CL: Overview of epidermal growth factor receptor biology and its role as a therapeutic target in human neoplasia. Semin Oncol 2002, 29(5 Suppl 14):3-9.
Arteaga CL, Baselga J: Tyrosine kinase inhibitors: why does the current process of clinical development not apply to them? Cancer cell 2004, 5(6):525-531.
Arteaga CL, Miller TW, Perez-Totres M et al. Loss of phosphatase and tensin homologue deleted on chromosome 10 engages ErbB3 and insulin-like growth factor-I receptor signaling to promote antiestrogen resistance in breast cancer. Cancer Res. 69, 4192-4201 (2009).
Atzori F, Tabernero J, Cervantes A et al. A Phase I pharmacokinetic and pharmacodynamic study of dalotuzumab (MK-0646), an anti-insulin-like growth factor-1 receptor monoclonal antibody, in patients with advanced solid tumors. Clin. Cancer Res. 17, 6304-6312 (2011).
Balana ME, Labriola L, Salatino M et al. Activation of ErbB-2 via a hierarchical interaction between ErbB-2 and type I insulin-like growth factor receptor in mammary tumor cells. Oncogene 20, 34-47 (2001).

Banappagari S, Corti M, Pincus S, Satyanarayanajois S: Inhibition of protein-protein interaction of HER2-EGFR and HER2-HER3 by a rationally designed peptidomimetic. Journal of biomolecular structure & dynamics 2012, 30(5):594-606.
Barbacci EG, Guarino BC, Stroh JG et al. The structural basis for the specificity of epidermal growth factor and heregulin binding. J. Biol. Chem. 270, 9585-9589 (1995).
Baselga J: Why the epidermal growth factor receptor? The rationale for cancer therapy. The oncologist 2002, 7 Suppl 4:2-8.
Baselga J, Arteaga CL: Critical update and emerging trends in epidermal growth factor receptor targeting in cancer. J Clin Oncol 2005, 23(11):2445-2459.
Baselga J: Targeting tyrosine kinases in cancer: the second wave. Science 2006, 312(5777):1175-1178.
Baselga J, Swain SM. Novel anticancer targets: revisiting ERBB2 and discovering ERBB3. Nat. Rev. Cancer 9, 463-475 (2009).
Baselga J, Cortés J, Kim SB et al. Pertuzumab plus trastuzumab plus docetaxel for metastatic breast cancer. N. Engl. J. Med. 366, 109-119 (2012).
Baxevanis CN, Voutsas IF, Tsitsilonis OE, Gritzapis AD, Sotiriadou R, Papamichail M. Tumor-specific CD4' T lymphocytes from cancer patients are required for optimal induction of cytotoxic T cells against the autologous tumor. J. Immunol. 164, 3902-3912 (2000).
Beerli RR, Graus-Porta D, Woods-Cook K, Chen X, Yarden Y, Hynes NE. Neu differentiation factor activation of ErbB-3 and ErbB-4 is cell specific and displays a differential requirement for ErbB-2. Mol. Cell. Biol. 15, 6496-6505 (1995).
Berchuck A, Rodriguez G, Kinney RB et al. Overexpression of HER-2/neu in endometrial cancer is associated with advanced stage disease. Am. J. Obstet. Gynecol. 164, 15-21 (1991).
Bergers G, Benjamin LE. Tumorigenesis and the angiogenic switch. Nat. Rev. Cancer 3, 401-410 (2003).
Bergmann U, Funatomi H, Yokoyama M, Beger HG, Korc M. Insulin-like growth factor I overexpression in human pancreatic cancer: evidence for autocrine and paracrine roles. Cancer Res. 55, 2007-2011 (1995).
Bhojani N, Jeldres C, Patard JJ et al. Toxicities associated with the administration of sorafenib, sunitinib, and temsirolimus and their management in patients with metastatic renal cell carcinoma. Eur. Urol. 53, 917-930 (2008).
Bianco F, Basini G, Grasselli F. Angiogenic activity of swine granulosa cells: effects of hypoxia and vascular endothelial growth factor Trap R1R2, a VEGF blocker. Domest. Amm. Endocrinol. 28, 308-319 (2005).
Boerner IL, Danielsen A, Maihle NJ: Ligand-independent oncogenic signaling by the epidermal growth factor receptor: v-ErbB as a paradigm. Exp Cell Res 2003, 284(1):111-121.
Boggio K, Nicoletti G, DiCarlo E et al. Interleukin 12-mediated prevention of spontaneous mammary adenocarcinomas in two lines of Her-2/neu transgenic mice. J. Exp. Med. 188, 589-596 (1998).
Borowsky AD, Namba R, Young U, Hunter KW, Hodgson JG, Tepper CG, McGoldrick ET, Muller WJ, Cardiff RD, Gregg JP: Syngeneic mouse mammary carcinoma cell lines: two closely related cell lines with divergent metastatic behavior. Clin Exp Metastasis 2005, 22(1):47-58.
Brabender J, Danenberg KD, Metzger R, Schneider PM, Park I, Salonga D, Holscher AH, Danenberg PV: Epidermal growth factor receptor and HER2-neu mRNA expression in non-small cell lung cancer is correlated with survival. Clinical cancer research : an official journal of the American Association for Cancer Research 2001, 7(7):1850-1855.
Brennan PJ, Kumagai T, Berezov A, Murali R, Greene MI. HER2/Neu: mechanisms of dimerization/oligomerization. Oncogene 19, 6093-6101 (2000).
Brouzes E, Medkova M, Savenelli N, Marran D, Twardowski M, Hutchison JB, Rothberg JM, Link DR, Perrimon N, Samuels ML: Droplet microfluidic technology for single-cell high-throughput screening. Proceedings of the National Academy of Sciences of the United States of America 2009, 106(34):14195-14200.
Brouzes E: Droplet microfluidics for single-cell analysis. Methods in molecular biology 2012, 853:105-139.

(56) References Cited

OTHER PUBLICATIONS

Browder T, Butterfield CE, Kraling BM, Shi B, Marshall B, O'Reilly MS, Folkman J: Antiangiogenic scheduling of chemotherapy improves efficacy against experimental drug-resistant cancer. Cancer Res 2000, 60(7):1878-1886.
Burgess AW, Cho HS, Eigenbrot C, Ferguson KM, Garrett TP, Leahy DJ, Lemmon MA, Sliwkowski MX, Ward CW, Yokoyama 5: An open-and-shut case? Recent insights into the activation of EGF/ErbB receptors. Mal Cell 2003, 12(3):541-552.
Buteau C, Markovic SN, Celis E. Challenges in the development of effective peptide vaccines for cancer. Mayo. Clin. Proc. 77, 339-349 (2002).
Butt O, Kulkarni S, Krishnan P, Ferrari M, Moldovan L, Moldovan NI. Quantification and functional analysis of chemotaxis by Laser Scanning Cytometry. Cytometry, 2005, 64A: 10-15.
Butt, Omar I., et al. "Stimulation of peri-implant vascularization with bone marrow-derived progenitor cells: monitoring by in vivo EPR oximetry." Tissue engineering 13.8 (2007): 2053-2061.
Camirand A, Lu Y, Pollak M. Co-targeting HER2/ErbB2 and insulin-like growth factor-1 receptors causes synergistic inhibition of growth in HER2-ovcrexpressing breast cancer cells. Med. Sci. Monit. 8(12), BR521-BR526 (2002).
Cardiff RD, Anver MR, Gusterson BA et al. The mammary pathology of genetically engineered mice: the consensus report and recommendations from the Annapolis meeting. Oncogene 19, 968-988 (2000).
Cardó-Vila M, Giordano RJ, Sidman RL, Bronk LF, Fan Z, Mendelsohn J, Arap W, Pasqualini R: From combinatorial peptide selection to drug prototype (II): targeting the epidermal growth factor receptor pathway. Proc Natl Acad Sci U S A, 107(11):5118-5123.
Carmeliet P. Angiogenesis in life, disease and medicine. Nature 438, 932-936 (2005).
Carpenito C, Davis PD, Dougherty ST, Dougherty GJ. Exploiting the differential production of angiogenic factors within the tumor microenvironment in the design of a novel vascular-targeted gene therapy-based approach to the treatment of cancer. Int. J. Radiat. Oncol. Biol. Phys. 54, 1473-1478 (2002).
Carter P, Presta L, Gorman CM et al. Humanization of an anti-p185HER2 antibody for human cancer therapy. Proc. Natl Acad Sci. USA 89, 4285-4289 (1992).
Cartwright T, Richards DA, Boehm KA: Cancer of the pancreas: are we making progress? A review of studies in the US Oncology Research Network. Cancer Control 2008, 15(4):308-313.
Casella I, Feccia T, Chelucci C et al. Autocrine-paracrine VEGF loops potentiate the maturation of megakaryocytic precursors through Flt1 receptor. Blood 101, 1316-1323 (2003).
Cefai D, Morrison BW, Sckell A et al. Targeting HER-2/neu for active-specific immunotherapy in a mouse model of spontaneous breast cancer. Int. J. Cancer 83, 393-400 (1999).
Chan JM, Stampfer MJ, Giovannucci E et al. Plasma insulin-like growth factor-I and prostate cancer risk: a prospective study. Science 279, 563-566 (1998).
Cho HS, Leahy DJ: Structure of the extracellular region of HER3 reveals an interdomain tether. Science 2002, 297(5585):1330-1333.
Cho HS, Mason K, Ramyar KX et al. Structure of the extracellular region of HER2 alone and in complex with the Herceptin Fab. Nature 421, 756-760 (2003).
Chorev M. The partial retro-inverso modification: a road traveled together. Biopolymers 80, 67-84 (2005).
Chorev M, Goodman M. Recent developments in retro peptides and proteins—an ongoing topochemical exploration. Trends Biotechnol. 13, 438-445 (1995).
Cirisano FD, Karlan By. The role of the HER-2/neu oncogene in gynecologic cancers. J. Soc. Gynecol. Invest. 3, 99-105 (1996).
Clive KS, Tyler JA, Clifton GT et al. The GP2 peptide: a HER2/neu-based breast cancer vaccine. J. Surg. Oncol. 105, 452-458 (2012).
Cobleigh MA, Langmuir VK, Sledge GW, Miller KD, Haney L, Novotny WF, Reimann JD, Vassel A: A phase I/II dose-escalation trial of bevacizumab in previously tTreated metastatic breast cancer. Semin Oncol 2003, 30(5 Suppl 16):117-124.
Colomer R, Shamon LA, Tsai MS, Lupu R. Herceptin: from the bench to the clinic. Cancer Invest. 19, 49-56 (2001).
Cox E, Verdonck F, Vanrompay D, Goddeeris B. Adjuvants modulating mucosal immune responses or directing systemic responses towards the mucosa. Vet. Res. 37, 511-539 (2006).
Croce CM, lorio MV, Casalini P. et al. microRNA-205 regulates HER3 in human breast cancer. Cancer Res. 69, 2195-2200 (2009).
Daemen T, de Mare A, Bungener L, de Jonge J, Huckriede A, Wilschut J. Virosomes for antigen and DNA delivery. Adv. Drug Deliv. Rev. 57, 451-463 (2005).
Dakappagari NK, Douglas DB, Triozzi PL, Stevens VC, Kaumaya PT. Prevention of mammary tumors with a chimeric HER-2 B-cell epitope peptide vaccine. Cancer Res. 60, 3782-3789 (2000).
Dakappagari NK, Pyles J, Parihar R, Carson WE, Young DC, Kaumaya PT. A chimeric multi-human epidermal growth factor receptor-2 B cell epitope peptide vaccine mediates superior antitumor responses. J. Immunol. 170, 4242-4253 (2003).
Dakappagari NK, Sundaram R, Rawale S, Liner A, Galloway DR, Kaumaya PT: Intracellular delivery of a novel multiepitope peptide vaccine by an amphipathic peptide carrier enhances cytotoxic T-cell responses in HLA-A*201 mice. J Pept Res 2005, 65(2):189-199.
Dakappagari NK, Lute KD, Rawale S et al. Conformational HER-2/neu B-cell epitope peptide vaccine designed to incorporate two native disulfide bonds enhances tumor cell binding and antitumor activities. J. Biol. Chem. 280, 54-63 (2005).
Dankort D, Maslikowski B, Warner N et al. Grb2 and Shc adapter proteins play distinct roles in Neu (ErbB-2)-induced mammary tumorigenesis: implications for human breast cancer. Mol. Cell. Biol. 21, 1540-1551 (2001).
Dela Cruz JS, Lau SY, Ramirez EM et al. Protein vaccination with the HER2/neu extracellular domain plus anti-HER2/neu antibody-cytokine fusion proteins induces a protective anti-HER2/neu immune response in mice. Vaccine 21, 1317-1326 (2003).
Disis ML, Calenoff E, McLaughlin G et al. Existent T-cell arid antibody immunity to HER-2/neu protein in patients with breast cancer. Cancer Res. 54, 16-20 (1994).
Disis ML, Gralow JR, Bernhard H, Hand SL, Rubin WD, Cheever MA. Peptide-based, but not whole protein, vaccines elicit immunity to HER-2/neu, oncogenic self-protein. J. Immunol. 156, 3151-3158 (1996).
Disis ML, Pupa SM, Gralow JR, Dittadi R, Menard S, Cheever MA. High-titer HER-2/ neu protein-specific antibody can be detected in patients with early-stage breast cancer. J. Clin. Oncol. 15, 3363-3367 (1997).
Disis ML, Grabstein KH, Sleath PR, Cheever MA. Generation of immunity to the HER-2/neu oncogenic protein in patients with breast and ovarian cancer using a peptide-based vaccine. Clin. Cancer Res. 5, 1289-1297 (1999).
Diwan M, Tafaghodi M, Samuel J. Enhancement of immune responses by co-delivery of a CpG oligodeoxynucleotide and tetanus toxoid in biodegradable nanospheres. J. Control. Release 85, 247-262 (2002).
Eisenberg D, Singer E, Landgraf R, Horan T. Slamon D. Identification of a heregulin binding site in HER3 extracellular domain. J. Biol. Chem. 276, 44266-44274 (2001).
Eisenhauer EA, Vermorken JB: The taxoids. Comparative clinical pharmacology and therapeutic potential. Drugs 1998, 55(1):5-30.
Elenius K, Erjala K, Sundvall M et al. Signaling via ErbB2 and ErbB3 associates with resistance and epidermal growth factor receptor (EGFR) amplification with sensitivity to EGFR inhibitor gefitinib in head and neck squamous cell carcinoma cells. Clin. Cancer Res. 12, 4103-4111 (2006).
Engelman JA, Zejnullahu K, Mitsudomi T et al. MET amplification leads to gefitinib resistance in lung cancer by activating ERBB3 signaling. Science 316, 1039-1043 (2007).
Engelman JA, Schoeberl B, Faber AC et al. An ErbB3 antibody, MM-121, is active in cancers with ligand-dependent activation. Cancer Res. 70, 2485-2494 (2010).
Epa VC, Ward CW: Model for the complex between the insulin-like growth factor I and its receptor: towards designing antagonists for the IGF-1 receptor. Protein Eng Des Sel 2006, 19(8):377-384.

(56) References Cited

OTHER PUBLICATIONS

Eskens FA, Verweij J: The clinical toxicity profile of vascular endothelial growth factor (VEGF) and vascular endothelial growth factor receptor (VEGFR) targeting angiogenesis inhibitors; a review. Eur I Cancer 2006, 42(18):3127-3139.

Ferguson KM, Berger MB, Mendrola JM, Cho HS, Leahy DJ, Lemmon MA: EGF activates its receptor by removing interactions that autoinhibit ectodomain dimerization. Mol Cell 2003, 11(2):507-517.

Ferrara N, Henzel WJ. Pituitary follicular cells secrete a novel heparin-binding growth factor specific for vascular endothelial cells. Biochem. Biophys. Res. Commun. 161, 851-858 (1989).

Ferrara N. Vascular endothelial growth factor as a target for anticancer therapy. Oncologist 9(Suppl. 1), S2-S10 (2004).

Ferrara N. The role of VEGF in the regulation of physiological and pathological angiogenesis. EXS (94), 209-231 (2005).

Ferrara N. VEGF as a therapeutic target in cancer. Oncology 69(Suppl. 3), S11-S16 (2005).

Ferrell N, Gallego-Perez D, Higuita-Castro N, Butler RT, Reen RK, Gooch KJ, Hansford DJ: Vacuum-assisted cell seeding in a microwell cell culture system. Analytical chemistry 2010, 82(6):2380-2386.

Fisk B, Blevins TL, Wharton JT, Ioannides CG. Identification of an immunodominant peptide of HER-2/neu protooncogene recognized by ovarian tumor-specific cytotoxic T lymphocyte lines. J. Exp. Med. 181, 2109-2117 (1995).

Fletcher MD, Campbell MM. Partially modified retro-inverso peptides: development, synthesis, and conformational behavior. Chem. Rev. 98, 763-796 (1998).

Folkman J. Tumor angiogenesis: therapeutic implications. N. Engl. J. Med. 285, 1182-1186 (1971).

Folkman J. Anti-angiogenesis: new concept for therapy of solid tumors. Ann. Surg. 175, 409-416 (1972).

Folkman J. Tumor suppression by p53 is mediated in part by the antiangiogenic activity of endostatin and tumstatin. Sci. STKE 2006, PE35 (2006).

Foy KC, Liu Z, Phillips G, Miller M, Kaumaya PT. Combination treatment with HER-2 and VEGF peptide mimics induces potent anti-tumor and anti-angiogenic responses in vitro and in vivo. J. Biol. Chem. 286, 13626-13637 (2011).

Foy KC, Miller MJ, Moldovan N, Carson WE, Kaumaya PTP: Combined vaccination with HER-2 peptide followed by therapy with VEGF peptide mimics exerts effective anti-tumor and antiangiogenic effects in vitro and in vivo. OncoImmunology 2012, 1(7):0-1.

Foy KC, Miller MJ, Moldovan N, Bozanovic T, Carson WE, Kaumaya PTP: Immunotherapy with HER2 and VEGF peptide mimics plus metronomic paclitaxel causes superior antineoplastic effects in transplantable and transgenic mouse models of human breast cancer. OncoImmunology 2012, 1(7):1004-1016.

Foy KC, Wygle RM, Miller MJ, Overholser JP, Bekaii-Saab T, Kaumaya PT: Peptide vaccines and peptidomimetics of EGFR (HER-1) ligand binding domain inhibit cancer cell growth in vitro and in vivo. J Immunol 2013, 191(1):217-227.

Franklin MC, Carey KD, Vajdos FF, Leahy DJ, de Vos AM, Sliwkowski MX. Insights into ErbB signaling from the structure of the ErbB2-pertuzumab complex. Cancer Cell 5, 317-328 (2004).

Freier S, Weiss O, Eran M, Flyvbjerg A, Dahan R, Nephesh I, Safra T, Shiloni E, Raz I: Expression of the insulin-like growth factors and their receptors in adenocarcinoma of the colon. Gut 1999, 44(5):704-708.

Frogne, T., et al., Activation of ErbB3, EGFR and ERK is essential for growth of human breast cancer cell lines with acquired resistance to fulvestrant. Breast Cancer Res Treat, 2009. 114(2): p. 263-75.

Fuh G, Wu P, Liang WC et al. Structure-function studies of two synthetic anti-vascular endothelial growth factor Fabs and comparison with the Avastin Fab. J. Biol. Chem. 281, 6625-6631 (2006).

Gallego-Perez D, Higuita-Castro N, Sharma S, Reen RK, Palmer AF, Gooch KJ, Lee LJ, Lannuttill, Hansford JJ: High throughput assembly of spatially controlled 3D cell clusters on a micro/nanoplatform. Lab on a chip 2010, 10(6):775-782.

Garner, A. P. et al. (2013) An antibody that locks HER3 in the inactive conformation inhibits tumor growth driven by HER2 or neuregulin. Cancer research 73, 6024-6035.

Garrett TP, McKern NM, Lou M, Elleman TC, Adams TE, Lovrecz GO, Zhu HI, Walker F, Frenkel MJ, Hoyne PA et al: Crystal structure of a truncated epidermal growth factor receptor extracellular domain bound to transforming growth factor alpha. Cell 2002, 110(6):763-773.

Garrett TP, McKern NM, Lou M et al. The crystal structure of a truncated ErbB2 ectodomain reveals an active conformation, poised to interact with other ErbB receptors. Mol. Cell 11, 495-505 (2003).

Garrett JT, Rawale S, Allen SD et al. Novel engineered trastuzumab conformational epitopes demonstrate in vitro and in vivo antitumor properties against HER-2/neu. J. Immunol. 178, 7120-7131 (2007).

Garrett TP, Burgess AW, Gan HK, Luwor RB, Cartwright G, Walker F, Orchard SG, Clayton AH, Nice EC, Rothacker J et al: Antibodies specifically targeting a locally misfolded region of tumor associated EGFR. Proc Natl Acad Sci U S A 2009, 106(13):5082-5087.

Garrett JT, Olivares MG, Rinehart C et al. 62. Transcriptional and posttranslational upregulation of HER3 (ErbB3) compensates for inhibition of the HER2 tyrosine kinase. Proc. Natl Acad. Sci. USA 108(12), 5021-5026 (2011).

Gasparini G, Longo R, Toi M, Ferrara N. Angiogenic inhibitors: a new therapeutic strategy in oncology. Nat. Clin. Pract. Oncol. 2, 562-577 (2005).

Gest C, Mirshahi P, Li H, Pritchard LL, Joimel U, Blot E, Chidiac J, Poletto B, Vannier JP, Varin R et al: Ovarian cancer: Stat3, RhoA and IGF-IR as therapeutic targets. Cancer Lett, 317(2):207-217.

Gluz 0, Liedtke C, Gottschalk N, Pusztai L, Nitz U, Harbeck N: Triple-negative breast cancer—current status and future directions. Ann Oncol 2009, 20(12):1913-1927.

Gordon MS, Matei D, Aghajanian C et al. Clinical activity of pertuzumab (rhuMAb 2C4), a HER dimerization inhibitor, in advanced ovarian cancer: potential predictive relationship with tumor HER2 activation status. J. Clin. Oncol. 24, 4324-4332 (2006).

Graus-Porta D, Beerli RR, Hynes NE. Single-chain antibody-mediated intracellular retention of ErbB-2 impairs Neu differentiation factor and epidermal growth factor signaling. Mol. Cell. Biol. 15, 1182-1191 (1995).

Graus-Porta D, Beerli RR, Daly JM, Hynes NE. ErbB-2, the preferred heterodimerization partner of all ErbB receptors, is a mediator of lateral signaling. EMBO J. 16, 1647-1655 (1997).

Grothey A. Recognizing and managing toxicities of molecular targeted therapies for colorectal cancer. Oncol (Williston Park) 20, 21-28 (2006).

Grunstein J, Roberts WG, Mathieu-Costello O, Hanahan D, Johnson RS. Tumor-derived expression of vascular endothelial growth factor is a critical factor in tumor expansion and vascular function. Cancer Res. 59, 1592-1598 (1999).

Guan J, Wang F, Li Z, Chen J, Guo X, Liao J, Moldovan NI. The stimulation of the cardiac differentiation of mesenchymal stem cells in tissue constructs that mimic myocardium structure and biomechanics. Biomaterials. 2011;32:5568-80.

Guix M, Faber AC, Wang SE, Olivares MG, Song Y, Qu S, Rinehart C, Seidel B, Yee D, Arteaga CL et al: Acquired resistance to EGFR tyrosine kinase inhibitors in cancer cells is mediated by loss of IGF-binding proteins. The Journal of clinical investigation 2008, 118(7):2609-2619.

Gullick WJ, Bottomley AC, Lofts FJ et al. Three dimensional structure of the transmembrane region of the proto-oncogenic and oncogenic forms of the neu protein. EMBO J. 11, 43-48 (1992).

Guy CT, Webster MA, Schaller M, Parsons TJ, Cardiff RD, Muller WJ. Expression of the neu protooncogene in the mammary epithelium of transgenic mice induces merastatic disease. Proc. Natl Acad. Sci. USA 89, 10578-10582 (1992).

Haluska P, Carboni JM, TenEyck C, Attar RM, Hou X, Yu C, Sagar M, Wong TW, Gottardis MM, Erlichman C: HER receptor signaling confers resistance to the insulin-like growth factor-I receptor inhibitor, BMS-536924. Molecular cancer therapeutics 2008, 7(9):2589-2598.

(56) References Cited

OTHER PUBLICATIONS

Hamburger AW, Zhang YX, Linn D et al. EBP1, an ErbB3-binding cancer and implicated in protein, is decreased in prostate hormone resistance. Mol. Cancer Ther. 7, 3176-3186 (2008).
Hamburger, A.W., The role of ErbB3 and its binding partners in breast cancer progression and resistance to hormone and tyrosine kinase directed therapies. J Mammary Gland Biol Neoplasia, 2008. 13(2): p. 225-33.
Hanahan D, Folkman J. Patterns and emerging mechanisms of the angiogenic switch during tumorigenesis. Cell 86, 353-364 (1996).
Hankinson SE, Willett WC, Colditz GA et al. Circulating concentrations of insulin-like growth factor-I and risk of breast cancer. Lancet 351, 1393-1396 (1998).
Hartmann C, Muller N, Blaukat A, Koch J, Benhar J, Wels WS: Peptide mimotopes recognized by antibodies cetuximab and matuzumab induce a functionally equivalent anti-EGFR immune response. Oncogene 2010, 29(32):4517-4527.
Hennighausen L. Mouse models for breast cancer. Oncogene 19, 966-967 (2000).
Heymach JV, Nilsson M, Blumenschein G, Papadimitrakopoulou V, Herbst R. Epidermal growth factor receptor inhibitors in development for the treatment of non-small cell lung cancer. Clin. Cancer Res. 12, 4441S-4445S (2006).
Hirsch FR, Varella-Garcia M, Bunn PA, Jr., Di Maria MV, Veve R, Bremmes RM, Baron AE, Zeng C, Franklin WA: Epidermal growth factor receptor in non-small-cell lung carcinomas: correlation between gene copy number and protein expression and impact on prognosis. J Clin Oncol 2003, 21(20):3798-3807.
Hoeben A, Landuyt B, Highley MS, Wildiers H, Van Oosterom AT, De Bruijn EA. Vascular endothelial growth factor and angiogenesis. Pharmacol. Rev. 56, 549-580 (2004).
Holash J, Davis S, Papadopoulos N et al. VEGF-trap: a VEGF blocker with potent antitumor effects. Proc. Natl Acad. Sci. USA 99, 11393-11398 (2002).
Holbro, T., et al., The ErbB2/ErbB3 heterodimer functions as an oncogenic unit: ErbB2 requires ErbB3 to drive breast tumor cell proliferation. Proc Natl Acad Sci U S A, 2003. 100(15): p. 8933-8.
Holmes FA, Walters RS, Theriault RL, Forman AD, Newton LK, Raber MN, Buzdar AU, Frye DK, Hortobagyi GN: Phase II trial of taxol, an active drug in the treatment of metastatic breast cancer. Natl Cancer Inst 1991, 83(24):1797-1805.
Houck KA, Ferrara N, Winer J, Cachianes G, Li B, Leung DW. The vascular endothelial growth factor family: identification of a fourth molecular species and characterization of alternative splicing of RNA. Mol. Endocrinol. 5, 1806-1814 (1991).
Hruby VJ. Conformational and topographical considerations in the design of biologically active peptides. Biopolymers 33, 1073-1082 (1993).
Hudis CA, Gianni L: Triple-negative breast cancer: an unmet medical need. The oncologist 2011, 16 Suppl 1:1-11.
Hudziak RM, Lewis GD, Winget M, Fendly BM, Shepard HM, Ullrich A: p185HER2 monoclonal antibody has antiproliferative effects in vitro and sensitizes human breast tumor cells to tumor necrosis factor. Mal Cell Biol 1989, 9(3):1165-1172.
Hynes NE, Lane HA. ERBB receptors and cancer: the complexity of targeted inhibitors. Nat. Rev. Cancer 5, 341-354 (2005).
Hynes Ne, Holbro T, Beerli RR, Maurer F, Koziczak M, Barbas CF. The ErbB2/ ErbB3 heterodimer functions as an oncogenic unit: ErbB2 requires ErbB3 to drive breast 65. tumor cell proliferation. Proc. Natl Acad. Sci. USA 100, 8933-8938 (2003).
Hynes NE, Stern DF. The biology of erbB-2/ neu/HEr-2 and its role in cancer. Biochim. Biophys. Acta 1198, 165-184 (1994).
Inno A, Di Salvatore M, Cenci T, Martini M, Orlandi A, Strippoli A, Ferrara AM, Bagala C, Cassano A, Larocca LM et al: Is there a role for IGF1R and c-MET pathways in resistance to cetuximab in metastatic colorectal cancer? Clin Colorectal Cancer, 10(4):325-332.
Inoue K, Slaton JW, Perrotte P, Davis DW, Bruns CJ, Hicklin DJ, McConkey DJ, Sweeney P, Radinsky R, Dinney CP: Paclitaxel enhances the effects of the anti-epidermal growth factor receptor monoclonal antibody ImClone C225 in mice with metastatic human bladder transitional cell carcinoma. Clin Cancer Res 2000, 6(12):4874-4884.
Inoue K, Slaton JW, Davis DW, Hicklin DJ, McConkey DJ, Karashima T, Radinsky R, Dinney CP: Treatment of human metastatic transitional cell carcinoma of the bladder in a murine model with the anti-vascular endothelial growth factor receptor monoclonal antibody DCIOI and paclitaxel. Clin Cancer Res 2000, 6(7):2635-2643.
International Search Report and Written Opinion of the U.S. International Searching Authority of Application No. PCT/US2014/018354, dated Aug. 8, 2014.
Iorio, M.V., et al., microRNA-205 regulates HER3 in human breast cancer. Cancer Res, 2009. 69(6): p. 2195-200.
Ishiwata T, Bergmann U, Kornmann M, Lopez M, Beger HG, Korc M: Altered expression of insulin-like growth factor II receptor in human pancreatic cancer. Pancreas 1997, 15(4):367-373.
Izumi Y, Xu L, di Tomaso E, Fukumura D, Jain RK. Tumour biology: herceptin acts as an anti-angiogenic cocktail. Nature 416, 279-280 (2002).
Jackson DC, Lau YF, Le T et al. A totally synthetic vaccine of generic structure that targets Toll-like receptor 2 on dendritic cells and promotes antibody or cytotoxic T cell responses. Proc. Natl Acad. Sci. USA 101, 15440-15445 (2004).
Jain RK. Normalization of tumor vasculature: an emerging concept in antiangiogenic therapy. Science 307, 58-62 (2005).
Jain RK, Duda DG, Clark JW, Loeffler JS: Lessons from phase III clinical trials on anti-VEGF therapy for cancer. Nat Clin Pract Oncol 2006, 3(1):24-40.
Jasinska J, Wagner S, Radauer C et al. Inhibition of tumor cell growth by antibodies induced after vaccination with peptides derived from the extracellular domain of Her-2/neu. Int. J. Cancer 107, 976-983 (2003).
Jemal A, Siegel R, Xu J, Ward E: Cancer statistics, 2010. CA Cancer J Clin 2010, 60(5):277-300.
Johnston JB. Navaratnam S, Pitz MW et al. Targeting the EGFR pathway for cancer therapy. Curr. Med. Chem. 13, 3483-3492 (2006).
Jordan VC, Osipoic, Meeke K et al. Role for HER2/neu and HER3 in fulvestrant-resistant breast cancer. Int. J. Oncol. 30, 509-520 (2007).
Kalli KR, Conover CA: The insulin-like growth factor/insulin system in epithelial ovarian cancer. Front Biosci 2003, 8:d714-722.
Kamat V, Donaldson JM, Kari C, Quadros MR, Lelkes PI, Chaiken I, Cocklin S, Williams JC, Papazoglou E, Rodeck U: Enhanced EGFR inhibition and distinct epitope recognition by EGFR antagonistic mAbs C225 and 425. Cancer Biol Ther 2008, 7(5):726-733.
Kamath, A.V., et al., Preclinical pharmacokinetics of MEHD7945A, a novel EGFR/HER3 dual-action antibody, and prediction of its human pharmacokinetics and efficacious clinical dose. Cancer Chemother Pharmacol, 2012, 1063-1069.
Kaumaya PT, Berndt KD, Heidorn DB, Trewhella J, Kezdy FJ, Goldberg E. Synthesis and biophysical characterization of engineered topographic immunogenic determinants with alpha alpha topology. Biochemistry 29, 13-23 (1990).
Kaumaya PT, VanBuskirk AM, Goldberg E, Pierce SK. Design and immunological properties of topographic immunogenic determinants of a protein antigen (LDH-C4) as vaccines. J. Biol. Chem. 267, 6338-6346 (1992).
Kaumaya PT, Kobs-Conrad S, Seo YH et al. Peptide vaccines incorporating a 'promiscuous' T-cell epitope bypass certain haplotype restricted immune responses and provide broad spectrum immunogenicity. J. Mol. Recogn. 6, 81-94 (1993).
Kaumaya PT, Foy KC, Garrett J et al. Phase I active immunotherapy with combination of two chimeric, human epidermal growth factor receptor 2, B-cell epitopes fused to a promiscuous T-cell epitope in patients with metastatic and/or recurrent solid tumors. J. Clin. Oncol. 27, 5270-5277 (2009).
Kaumaya PT. Could precision-engineered peptide epitopes/vaccines be the key to a cancer cure? Future Oncol. 7, 807-810 (2011).

(56) References Cited

OTHER PUBLICATIONS

Kaumaya PT, Foy KC: Peptide vaccines and peptidomimetics targeting HEr and VEGF proteins may offer a potentially new paradigm in cancer immunotherapy. Future Oncol 2012, 8(8):961-987.
Kerbel RS. Inhibition of tumor angiogenesis as a strategy to circumvent acquired resistance to anti-cancer therapeutic agents. Bioessays 13, 31-36 (1991).
Kern JA, Schwartz DA, Nordberg JE et al. p185neu expression in human lung adenocarcinomas predicts shortened survival. Cancer Res. 50, 5184-5187 (1990).
Keyt BA, Nguyen HV, Berleau LT et al. Identification of vascular endothelial growth factor determinants for binding KDR and FLT-1 receptors. Generation of receptorselective Vegf variants by site-directed mutagenesis. J. Biol. Chem. 271, 5638-5646 (1996).
Khosravi Shahi P, Fernandez Pineda I. Tumoral angiogenesis: review of the literature. Cancer Invest. 26, 104-108 (2008).
Kim JY, Sun Q, Oglesbee M, Yoon SO. The role of ErbB2 signaling in the onset of terminal differentiation of oligodendrocytes in vivo. J. Neurosci. 23, 5561-5571 (2003).
Kim DW, Huamani J, Fu A, Hallahan DE. Molecular strategies targeting the host component of cancer to enhance tumor response to radiation therapy. Int. J. Radiat. Oncol. Biol. Phys. 64, 38-46 (2006).
Klein DE, Nappi VM, Reeves GT, Shvartsman SY, Lemmon MA: Argos inhibits epidermal growth factor receptor signalling by ligand sequestration. Nature 2004, 430(7003):1040-1044.
Klein DE, Stayrook SE, Shi F, Narayan K, Lemmon MA: Structural basis for EGFR ligand sequestration by Argos. Nature 2008, 453(7199):1271-1275.
Klement G, Baruchel S, Rak J, Man S, Clark K, Hicklin DJ, Bohlen P, Kerbel RS: Continuous low-dose therapy with vinblastine and VEGF receptor-2 antibody induces sustained tumor regression without overt toxicity. J Clin Invest 2000, 105(8):RI5-24.
Kluftinger AM, Robinson BW, Quenville NF, Finley RJ, Davis NL: Correlation of epidermal growth factor receptor and c-erbB2 onco-gene product to known prognostic indicators of colorectal cancer. Surg Oncol 1992, 1(1):97-105.
Kobayashi H, Wood M, Song Y, Appella E, Celis E. Defining promiscuous MHC class II helper T-cell epitopes for the HER2/neu tumor antigen. Cancer Res. 60, 5228-5236 (2000).
Kobs-Conrad S, Lee H, DiGeorge AM, Kaumaya PT. Engineered topographic determinants with alpha beta, beta alpha beta, and beta alpha beta alpha topologies show high affinity binding to native protein antigen (lactate dehydrogenase-C4). J. Biol. Chem. 268, 25285-25295 (1993).
Konecny GE, Meng YG, Untch M et al. Association between HER-2/neu and vascular endothelial growth factor expression predicts clinical outcome in primary breast cancer patients. Clin. Cancer Res. 10, 1706-1716 (2004).
Koutras, A.K., et al., The upgraded role of HER3 and HER4 receptors in breast cancer. Crit Rev Oncol Hematol, 2010. 74(2): p. 73-78.
Kulkarni S, Orth R, Moldovan NI. Micropatterning of endothelial cells by guided stimulation with angiogenic factors. Biosensors and Bioelectronics, 2004, 19: 1401-1407.
Kuo CJ, Farnebo F, Yu EY et al. Comparative evaluation of the antitumor activity of antiangiogenic proteins delivered by gene transfer. Proc. Natl Acad. Sci. USA 98, 4605-4610 (2001).
KuribayashAa, Kataoka K, Kurabayashi T, Miura M. Evidence that basal activity, but not transactivation, of the epidermal growth factor receptor tyrosine kinase is required for insulin-like growth factor I-induced activation of extracellular signal-regulated kinase in oral carcinoma cells. Endocrinology 145, 4976-4984 (2004).
Lahm H, Suardet L, Laurent PL, Fischer JR, Ceyhan A, Givel JC, Odartchenko N: Growth regulation and co-stimulation of human colorectal cancer cell lines by insulin-like growth factor I, II and transforming growth factor alpha. Br J Cancer 1992, 65(3):341-346.
Lairmore MD, DiGeorge AM, Conrad SF, Trevino AV, Lal RB, Kaumaya PT. Human T-Lymphotropic virus type 1 peptides in chimeric and multivalent constructs with promiscuous T-cell epitopes enhance immunogenicity and overcome genetic restriction. J. Virol. 69, 6077-6089 (1995).
Landgraf, R. and D. Eisenberg, Heregulin reverses the oligomerization of HER3. Biochemistry, 2000. 39(29): p. 8503-11.
Lazoura E, Apostolopoulos V. Rational peptide-based vaccine design for cancer immunotherapeutic applications. Curr. Med. Chem. 12, 629-639 (2005).
Lee-Hoeflich ST, Crocker L, Yao E et al. A central role for HER3 in HER2-amplified breast cancer: implications for targeted therapy. Cancer Res. 68, 5878-5887 (2008).
Le Tourneau C, Raymond E, Faivre S. Sunitinib: a novel tyrosine kinase inhibitor. A brief review of its therapeutic potential in the treatment of renal carcinoma and gastrointestinal stromal tumors (GIST). Ther. Clin Risk Manag. 3, 341-348 (2007).
Levitzki A. Tyrphostins: tyrosine kinase blockers as novel antiproliferative agents and dissectors of signal transduction. FASEB J6:3275-82 (1990).
Levitzki A. Tyrphostins—potential antiproliferative agents and novel molecular tools. Biochemical. Pharmacol. 40, 913-918 (1990).
Li B, Ogasawara AK, Yang R, Wei W, He GW, Zioncheck TF, Bunting S, de Vos AM, Jin H: KDR (VEGF receptor 2) is the major mediator for the hypotensive effect of VEGF. Hypertension 2002, 39(6):1095-1100.
Li Calzi S, Neu MB, Shaw LC, Kielczewski JL, Moldovan NI, Grant MB. EPCs and pathological angiogenesis: when good cells go bad. Microvasc Res. 2010, 79:207-16.
Li P, Veldwijk MR, Zhang Q, Li ZB, Xu WC, Fu S: Co-inhibition of epidermal growth factor receptor and insulin-like growth factor receptor 1 enhances radiosensitivity in human breast cancer cells. BMC Cancer 2013, 13:297.
Li S, Schmitz KR, Jeffrey PD, Wiltzius JJ, Kussie P, Ferguson KM: Structural basis for inhibition of the epidermal growth factor receptor by cetuximab. Cancer Cell 2005, 7(4):301-311.
Li S, Kussie P, Ferguson KM: Structural basis for Egf receptor inhibition by the therapeutic antibody IMC-11F8. Structure 2008, 16(2):216-227.
Liang Y, Brekken RA, Hyder SM: Vascular endothelial growth factor induces proliferation of breast cancer cells and inhibits the anti-proliferative activity of anti-hormones. Endocr Relat Cancer 2006, 13(3):905-919.
Lin EY, Jones JG, Li P et al. Progression to malignancy in the polyoma middle T oncoprotein mouse breast cancer model provides a reliable model for human diseases. Am. J. Pathol. 163, 2113-2126 (2003).
Lindencrona JA, Preiss S, Kammertoens T et al. CD430 T cell-mediated HER-2/neuspecific tumor rejection in the absence of B cells. Int. J. Cancer 109, 259-264 (2004).
Lindstrom S, Andersson-Svahn H: Overview of single-cell analyses: microdevices and applications. Lab on a chip 2010, 10(24):3363-3372.
Liu BL, Ordonez-Ercan D, Fan ZY, Edgerton SM, Yang XH, Thor AD. Downregulation of erbB3 abrogates erbB2-mediated tamoxifen resistance in breast cancer cells. Int. J. Cancer 120, 1874-1882 (2007).
Lu Y, Zi X, Pollak M: Molecular mechanisms underlying IGF-I-induced attenuation of the growth-inhibitory activity of trastuzumab (Herceptin) on SKBR3 breast cancer cells. International journal of cancer Journal international du cancer 2004, 108(3):334-341.
Lykkesfeldt AE, Frogne T, Benjaminsen RV et al. Activation of ErbB3, EGFR and Erk is essential for growth of human breast cancer cell lines with acquired resistance to fulvestrant. Breast Cancer Res. Treat. 114, 263-275 (2009).
Lynch JM, Briles DE, Metzger DW. Increased protection against pneumococcal disease by mucosal administration of conjugate vaccine plus interleukin-12. Infect. Immun. 71, 4780-4788 (2003).
Ma J, Pollak MN, Giovannucci E et al. Prospective study of colorectal cancer risk in men and plasma levels of insulin-like growth factor (IGF)-I and IGF-binding protein-3. J. Natl Cancer Inst. 91, 620-625 (1999).
McMahon G. VEGF receptor signaling in tumor angiogenesis. Oncologist 5(Suppl. 1), S3-S10 (2000).

(56) References Cited

OTHER PUBLICATIONS

McNeela EA, Mills KH. Manipulating the immune system: humoral versus cell-mediated immunity. Adv. Drug Deliv. Rev. 51, 43-54 (2001).
Mendelsohn J, Baselga J: Epidermal growth factor receptor targeting in cancer. Semin Oneal 2006, 33(4):369-385.
Mendelsohn J. Targeting the epidermal growth factor receptor for cancer therapy. J. Clin. Oncol 20, 1S-13S (2002).
Miller, T.W., et al., Loss of Phosphatase and Tensin homologue deleted on chromosome 10 engages ErbB3 and insulin-like growth factor-I receptor signaling to promote antiestrogen resistance in breast cancer. Cancer Res, 2009. 69(10): p. 4192-201.
Mimura K, Kono K, Hanawa M et al. Frequencies of HER-2/neu expression and gene amplification in patients with oesophageal squamous cell carcinoma. Br. J. Cancer 92, 1253-1260 (2005).
Mirschberger, C. et al. (2013) RG7116, a therapeutic antibody that binds the inactive HER3 receptor and is optimized for immune effector activation. Cancer Res 73, 5183-5194.
Mittendorf EA, Storrer CE, Foley RJ et al. Evaluation of the HER2/neu-derived peptide GP2 for use in a peptide-based breast cancer vaccine trial. Cancer 106, 2309-2317 (2006).
Mittendorf EA, Clifton GT, Holmes JP et al. Clinical trial results of the HER-2/neu (E75) vaccine to prevent breast cancer recurrence in high-risk patients: from US Military Cancer Institute Clinical Trials Group Study 1-01 and 1-02. Cancer 118(10), 2594-2602 (2012).
Mizejewski GJ. Peptides as receptor ligand drugs and their relationship to G-coupled signal transduction. Expert Opin Invest. Drugs 10, 1063-1073 (2001).
Moasser MM, Sergina NV, Rausch M et al. Escape from HER-family tyrosine kinase inhibitor therapy by the kinase-inactive HER3. Nature 445, 437-441 (2007).
Moasser MM, Sergina NV. The Her family and cancer: emerging molecular mechanisms and therapeutic targets. Trends Mol. Med. 13, 527-534 (2007).
Moldovan NI, Goldschmidt-Clermont P, Parker-Thornburg J, Kolattukudy PE. Contribution of Monocytes/Macrophages to Compensatory Neovascularization: The Drilling of Metalloelastase-Positive Tunnels in Ischemic Myocardium. Circ. Res. 2000, 87: 378-384.
Moldovan NI, Asahara T. Role of blood mononuclear cells in recanalization and vascularization of thrombi: Past, present and future, Trends Cardiovasc. Med., 2003, 13: 265-269.
Moldovan NI. Functional adaptation: the key to plasticity of cardiovascular "stem" cells? Stem Cells Dev. 14, 111-121 (2005).
Moldovan L, Moldovan NI. Role of monocytes and macrophages in angiogenesis. EXS (94), 127-146 (2005).
Monsky WL, Mouta Carreira C, Tsuzuki Y, Gohongi T, Fukumura D, Jain RK. Role of host microenvironment in angiogenesis and microvascular functions in human breast cancer xenografts: mammary fat pad versus cranial tumors. Clin. Cancer Res. 8, 1008-1013 (2002).
Morgillo F, Woo JK, Kim ES, Hong WK, Lee HY. Heterodimerization of insulin-like growth factor receptor/epidermal growth factor receptor and induction of survivin expression counteract the antitumor action of erlotinib. Cancer Res. 66, 10100-10111 (2006).
Morrison C, Zanagnolo V, Ramirez N. et al. HER-2 is an independent prognostic factor in endometrial cancer: association with outcome in a large cohort of surgically staged patients. J. Clin. Oncol. 24, 2376-2385 (2006).
Muller YA, Christinger HW, Keyt BA, de Vos AM. The crystal structure of vascular endothelial growth factor (VEGF) refined to 1.93 A resolution: multiple copy flexibility and receptor binding. Structure 5, 1325-1338 (1997).
Muller YA, Li B, Christinger HW, Wells IA, Cunningham BC, de Vos AM. Vascular endothelial growth factor: crystal structure and functional mapping of the kinase domain receptor binding site. Proc. Natl Acad. Sci. USA 94, 7192-7197 (1997).
Nagy JA, Dvorak AM, Dvorak HF. VEGF-A and the induction of pathological angiogenesis. Annu. Rev. Pathol. 2, 251-275 (2007).
Nagy JA, Benjamin L, Zeng H, Dvorak AM, Dvorak HF. Vascular permeability, vascular hyperpermeability and angiogenesis. Angiogenesis 11, 109-119 (2008).
Nahta R, Hung MC, Esteva FJ. The HER-2-targeting antibodies trastuzumab and pertuzumab synergistically inhibit the survival of breast cancer cells. Cancer Res. 64, 2343-2346 (2004).
Nahta R, Yuan LX, Zhang B, Kobayashi R, Esteva FJ. Insulin-like growth factor-I receptor/human epidermal growth factor receptor 2 heterodimerization contributes to trastuzumab resistance of breast cancer cells. Cancer Res. 65, 11118-11128 (2005).
Nahta R, Yu D, Hung MC, Hortobagyi GN, Esteva FJ. Mechanisms of disease: understanding resistance to HER2-targeted therapy in human breast cancer. Nat. Clin. Pract. Oncol. 3, 269-280 (2006).
Nahta R. Pharmacological strategies to overcome HER2 cross-talk and trastuzumab resistance. Curr. Med. Chem. 19, 1065-1075 (2012).
Nair S, Boczkowski D, Moeller B, Dewhirst M, Vieweg J, Gilboa E. Synergy between tumor immunotherapy and antiangiogenic therapy. Blood 102, 964-971 (2003).
Nanni P, Nicoletti G, De Giovanni C et al. Combined allogeneic tumor cell vaccination and systemic interleukin 12 prevents mammary carcinogenesis in HER-2/neu transgenic mice. J. Exp. Med. 194, 1195-1205 (2001).
Naumov GN, Bender E, Zurakowski D et al. A model of human tumor dormancy: an angiogenic switch from the nonangiogenic phenotype. J. Natl Cancer Inst. 98, 316-325 (2006).
Nelson NJ. Angiogenesis research is on fast forward. J. Natl Cancer Inst. 91, 820-822 (1999).
Niehans GA, Singleton TP, Dykoski D, Kiang DT. Stability of HER-2/neu expression over time and at multiple metastatic sites. J. Natl Cancer Inst. 85, 1230-1235 (1993).
O'Hagan DT, Valiante NM. Recent advances in the discovery and delivery of vaccine adjuvants. Nat. Rev. Drug Discov. 2, 727-735 (2003).
Olayioye MA, Neve RM, Lane HA, Hynes NE. The ErbB signaling network: receptor heterodimerization in development and cancer. EMBO J. 19, 3159-3167 (2000).
Oshima RG, Lesperance J, Munoz V et al. Angiogenic acceleration of Neu induced mammary tumor progression and metastasis. Cancer Res. 64, 169-179 (2004).
Osipo, C., et al., Role for HER2/neu and HER3 in fulvestrant-resistant breast cancer. Int. J Oncol, 2007. 30(2): p. 509-20.
Paik S, Hazan R, Fisher ER et al. Pathologic findings from the National Surgical Adjuvant Breast and Bowel Project: prognostic significance of erbB-2 protein overexpression in primary breast cancer. J. Clin. Oncol. 8, 103-112 (1990).
Paniana-Bordignon P, Tan A, Termijtelen A, Demotz S, Corradin G, Lanzavecchia A. Universally immunogenic T cell epitopes: promiscuous binding to human MHC class II and promiscuous recognition by T cells. Eur. J. Immunol. 19, 2237 (1989).
Partidos CD, Steward MW. Prediction and identification of a T cell epitope in the fusion protein of measles virus immunodominant in mice and humans. J. Gen. Virol. 71(Pt 9), 2099-2105 (1990).
Patan S. Vasculogenesis and angiogenesis as mechanisms of vascular network formation, growth and remodeling. J. Neurooncol. 50, 1-15 (2000).
Pei XF, Noble MS, Davoli MA, Rosfjord E, Tilli MT, Furth PA, Russell R, Johnson MD, Dickson RB: Explant-cell culture of primary mammary tumors from MMTV-c-Myc transgenic mice. In Vitro Cell Dev Biol Anim 2004, 40(1-2):14-21.
Pennarun B, Kleibeuker JH, Oenema T, Stegehuis JH, de Vries EG, de Jong S: Inhibition of IGF-1R-dependent PI3K activation sensitizes colon cancer cells specifically to DR5-mediated apoptosis but not to rhTRAIL. Anal Cell Pathol (Amst), 33(5):229-244.
Perez SA, Sociropoulou PA, Sotiriadou NN et al. HER-2/neu-derived peptide 884-899 is expressed by human breast, colorectal and pancreatic adenocarcinomas and is recognized by in-vitro-induced specific CD4(+) T cell clones. Cancer Immunol. Immunother. 50, 615-624 (2002).
Perona R. Cell signalling: growth factors and tyrosine kinase receptors. Clin. Transl Oncol. 8, 77-82 (2006).
Peters G, Gongoll S, Langner C, Mengel M, Piso P, Klempnauer J, Ruschoff J, Kreipe H, von Wasielewski R: IGF-1R, IGF-1 and

(56) References Cited

OTHER PUBLICATIONS

IGF-2 expression as potential prognostic and predictive markers in colorectal-cancer. Virchows Arch 2003, 443(2):139-145.
Piechocki MP, Pilon SA, Wei WZ. Complementary antitumor immunity induced by plasmid DNa encoding secreted and cytoplasmic human ErbB-2. J. Immunol. 167, 3367-3374 (2001).
Pinkas-Kramarski R, Soussan L, Waterman H et al. Diversification of Neu differentiation factor and epidermal growth factor signaling 60. By combinatorial receptor interactions. EMBo J. 15, 2452-2467 (1996).
Pintens S, Neven P, Drijkoningen M, Van Belle V, Moerman P, Christiaens MR, Smeets A, Wildiers H, Vanden Bempt I: Triple negative breast cancer: a study from the point of view of basal CK5/6 and HER-1. J Clin Pathol 2009, 62(7):624-628.
Pomerantz MM, Shrestha Y, Flavin RJ et al. Analysis of the 10q11 cancer risk locus implicates MSMB and NCOA4 in human prostate tumorigenesis. PLoS Genet. 6, e1001204 (2010).
Pollak MN, Schernhammer ES, Hankinson SE: Insulin-like growth factors and neoplasia. Nat Rev Cancer 2004, 4(7):505-518.
Press MF, Cordon-Cardo C, Slamon DJ. Expression of the HER-2/neu proto-oncogene in normal human adult and fetal tissues. Oncogene 5(7) 953-962 (1990).
Press MF, Lenz HJ: EGFR, HER2 and VEGF pathways: validated targets for cancer treatment. Drugs 2007, 67(14):2045-2075.
Pupa SM, Invernizzi AM, Ford S et al. Prevention of spontaneous neu-expressing mammary tumor development in mice transgenic for rat proto-neu by DNA vaccination. Gene Ther. 8, 75-79 (2001).
Radinsky R, Risin S, Fan D, Dong Z, Bielenberg D, Bucana CD, Fidler IJ: Level and function of epidermal growth factor receptor predict the metastatic potential of human colon carcinoma cells. Clin Cancer Res 1995, 1(1):19-31.
Rajkumar, T., et al., c-erbB3 protein expression in ovarian cancer. Clin Mol Pathol, 1996. 49(4): p. M199-202.
Rajkumar T, Stamp GWH, Pandha HS, Waxman J, Gullick WJ. Expression of the type 1 tyrosine kinase growth factor receptors EGF receptor, c-erbB2 and c-erbB3 in bladder cancer. J Pathol. 179, 381-385 (1996).
Reilly RT, Gottlieb MB, Ercolini AM et al. HER-2/neu is a tumor rejection target in tolerized HER-2/neu transgenic mice. Cancer Res. 60, 3569-3576 (2000).
Reinacher-Schick A, Pohl M, Schmiegel W. Drug insight: antiangiogenic therapies for gastrointestinal cancers—focus on monoclonal antibodies. Nat. Clin. Pract. Gastroenterol. Hepatol. 5, 250-267 (2008).
Riemer AB, Klinger M, Wagner S et al. Generation of peptide mimics of the epitope recognized by trastuzumab on the oncogenic protein Her-2/neu. J. Immunol. 173, 394-401 (2004).
Riemer AB, Kraml G, Scheiner O, Zielinski CC, Jensen-Jarolim E. Matching of trastuzumab (Herceptin) epitope mimics onto the surface of Her-2/neu—a new method of epitope definition. Mol. Immunol. 42, 1121-1124 (2005).
Rivera F, Vega-Villegas ME, Lopez-Brea MF, Marquez R: Current situation of Panitumumab, Matuzumab, Nimotuzumab and Zalutumumab. Acta oncologica 2008, 47(1):9-19.
Roop RP, Ma CX. Endocrine resistance in breast cancer: molecular pathways and rational development of targeted therapies. Future Oncol. 8, 273-292 (2012).
Rowinsky, E.K., The erbB family: targets for therapeutic development against cancer and therapeutic strategies using monoclonal antibodies and tyrosine kinase inhibitors. Annu Rev Med, 2004. 55: p. 433-57.
Ryan AJ, Wedge SR. ZD6474—a novel inhibitor of VEGFR and EGFR tyrosine kinase activity. Br. J. Cancer 92 (Suppl. 1), S6-S13 (2005).
Saito H, Tsujitani S, Ikeguchi M, Maeta M, Kaibara N. Relationship between the expression of vascular endothelial growth factor and the density of dendritic cells in gastric adenocarcinoma tissue. Br. J. Cancer 78, 1573-1577 (1998).
Sawano A, Takayama S, Matsuda M, Miyawaki A: Lateral propagation of EGF signaling after local stimulation is dependent on receptor density. Dev Cell 2002, 3(2):245-257.

Scheuer W, FriessT, Burtscher H, Bossenmuer B, Endl J, Hasmann M. Strongly enhanced antitumor activity of trastuzumab and pertuzumab combination treatment on HER2-positive human xenograft tumor models. Cancer Res. 24, 9330-9336 (2009).
Schmiedel J, Blaukat A, Li S, Knochel T, Ferguson KM: Matuzumab binding to EGFR prevents the conformational rearrangement required for dimerization. Cancer Cell 2008, 13(4):365-373.
Schmitz KR, Ferguson KM: Interaction of antibodies with ErbB receptor extracellular regions. Experimental cell research 2009, 315(4):659-670.
Schneider BP, Wang M, Radovich M et al. Association of vascular endothelial growth factor and vascular endothelial growth factor receptor-2 genetic polymorphisms with outcome in a trial of paclitaxel compared with paclitaxel plus bevacizumab in advanced breast cancer: ECOG 2100. J. Clin. Oncol. 26, 4672-4678 (2008).
Schoeberl, B., et al., An ErbB3 antibody, MM-121, is active in cancers with ligand-dependent activation. CancerRes, 2010. 70(6): p. 2485-94.
Scholl S, Beuzeboc P, Pouillart P. Targeting HER2 in other tumor types. Ann. Oncol. 12 (Suppl. 1), S81-S87 (2001).
Sears AK, Perez SA, Clifton GT et al. AE37: a novel T-cell-eliciting vaccine for breast cancer. Expert Opin Biol. Ther. 11, 1543-1550 (2011).
Sengupta N, Caballero S, Sullivan SM, Chang LI, Afzal A, Li Calzi S, Kielczewski JL, Prabarakan S, Ellis EA, Moldovan L, Moldovan NI, Boulton ME, Grant MB. Regulation of adult hematopoietic stem cells fate for enhanced tissue-specific repair. Mol Ther. 2009, 17:1594-604.
Sergina, N.V., et al., Escape from HER-family tyrosine kinase inhibitor therapy by the kinase-inactive HER3. Nature, 2007. 445(7126): p. 437-41.
Sergina, N.V. and M.M. Moasser, The HER family and cancer: emerging molecular mechanisms and therapeutic targets. Trends Mol Med, 2007. 13(12): p. 527-34.
Sereno M, Brunello A, Chiappori A et al. Cardiac toxicity: old and new issues in anticancer drugs. Clin. Transl Oncol. 10, 35-46 (2008).
Shepard HM, Lewis GD, Sarup JC, Fendly BM, Maneval D, Mordenti J, Figari I, Kotts CE, Palladino MA, Jr., Ullrich A et al: Monoclonal antibody therapy of human cancer: taking the HER2 protooncogene to the clinic. ] Clin Immunol 1991, 11(3):117-127.
Sherwood ER, Van Dongen JL, Wood CG, Liao S, Kozlowski JM, Lee C: Epidermal growth factor receptor activation in androgen-independent but not androgen-stimulated growth of human prostatic carcinoma cells. Br J Cancer 1998, 77(6):855-861.
Shi, F., et al., ErbB3/HER3 intracellular domain is competent to bind ATP and catalyze autophosphorylation. Proc Natl Acad Sci U S A, 2010. 107(17): p. 7692-7.
Sithanandam G, Anderson LM. The ERBB3 receptor in cancer and cancer gene therapy. Cancer Gene Ther. 15, 413-448 (2008).
Sliwkowski MX, Lee-Hoeflich ST, Crocker L et al. A central role for HER3 in HER2-amplified breast cancer: implications for targeted therapy. Cancer Res. 68, 5878-5887 (2008).
Slomiany MG, Black LA, Kibbey MM, Day TA, Rosenzweig SA. IGF-1 induced vascular endothelial growth factor secretion in head and neck squamous cell carcinoma. Biochem. Biophys. Res. Commun. 342, 851-858 (2006).
Smith WD, Wells PW, Burrells C, Dawson AM. Immunoglobulins, antibodies and inhibitors of parainfluenza 3 virus in respiratory secretions of sheep. Arch. Virol. 49, 329-337 (1975).
Sotiriadou R, Perez SA, Gritzapis AD et al. Peptide HER2(776-788) represents a naturally processed broad MHC class II-restricted T cell epitope. Br. J. Cancer 85, 1527-1534 (2001).
Srinivasan R, Leverton KE, Sheldon H, Hurst HC, Sarraf C, Gullick WJ. Intracellular expression of the truncated extracellular domain of c-erbB-3/HER3. Cell. Signal. 13, 321-330 (2001).
Srinivasan M, Wardtop RM, Gienapp IE, Stuckman SS, Whitacre CC, Kaumaya PT. A retro-inverso peptide mimic of CD28 encompassing the MYPPPY motif adopts a polyproline type II helix and inhibits encephalitogenic T cells in vitro. J. Immunol. 167, 578-585 (2001).

(56) References Cited

OTHER PUBLICATIONS

Srinivasan M, Gienapp IE, Stuckman SS et al. Suppression of experimental autoimmune encephalomyelitis using peptide mimics of CD28. J. Immunol. 169, 2180-2188 (2002).
Stern DF. ERBB3/HER3 and ERBB2/HER2 duet in mammary development and breast cancer. J. Mammary Gland Biol. 13, 215-223 (2008).
Stoeltzing O, Liu W, Reinmuth N, Fan F, Parikh AA, Bucana CD, Evans DB, Semenza GL, Ellis LM: Regulation of hypoxia-inducible factor-1alpha, vascular endothelial growth factor, and angiogenesis by an insulin-like growth factor-I receptor autocrine loop in human pancreatic cancer. Am J Pathol 2003, 163(3):1001-1011.
Sun X, Kanwar JR, Leung E, Lehnert K, Wang D, Krissansen GW. Angiostatin enhances B7.1-mediated cancer immunotherapy independently of effects on vascular endothelial growth factor expression. Cancer Gene Ther. 8, 719-727 (2001).
Sun JF, Phung T, Shiojima I, Felske T, Upalakalin JN, Feng D, Kornaga T, Dor T, Dvorak AM, Walsh K et al: Microvascular patterning is controlled by fine-tuning the Akt signal. Proc Natl Acad Sci U S A 2005, 102(1):128-133.
Sundaram R, Dakappagari NK, Kaumaya PT. Synthetic peptides as cancer vaccines. Biopolymers 66, 200-216 (2002).
Sutherland RL. Endocrine resistance in breast cancer: new roles for ErbB3 and ErbB4. Breast Cancer Res. 13(3), 106 (2011).
Taylor EM, Otero DA, Banks WA, O'Brien JS. Retro-inverso prosaptide peptides retain bioactivity, are stable in vivo, and are blood-brain barrier permeable. J. Pharmacol. Exp. Ther. 295, 190-194 (2000).
Teicher BA, Holden SA, Ara G, Sotomayor EA, Huang ZD, Chen YN, Brem H: Potentiation of cytotoxic cancer therapies by TNP-470 alone and with other anti-angiogenic agents. Int J Cancer 1994, 57(6):920-925.
Tischer E, Mitchell R, Hartman T et al. The human gene for vascular endothelial growth factor. Multiple protein forms are encoded through alternative exon splicing. J. Biol. Chem. 266, 11947-11954 (1991).
Tonra JR, Corcoran E, Deevi DS, Steiner P, Kearney J, Li H, Ludwig DL, Zhu Z, Witte L, Surguladze D et al: Prioritization of EGFR/IGF-IR/VEGFR2 combination targeted therapies utilizing cancer models. Anticancer Res 2008, 29(6):1999-2007.
Tuttle TM, Anderson BW, Thompson WE et al. Proliferative and cytokine responses to class II HER-2/neu-associated peptides in breast cancer patients. Clin. Cancer Res. 4, 2015-2024 (1998).
Tzahar E, Waterman H, Chen X et al. A hierarchical network of interreceptor interactions determines signal transduction by Neu differentiation factor/neuregulin and epidermal growth factor. Mol. Cell. Biol. 16, 5276-5287 (1996).
Ueno, Y., et al., Heregulin-induced activation of ErbB3 by EGFR tyrosine kinase activity promotes tumor growth and metastasis in melanoma cells. In J Cancer, 2008. 123(2): p. 340-7.
Valsecchi ME, McDonald M, Brody JR, Hyslop T, Freydin B, Yeo CJ, Solomides C, Peiper SC, Witkiewicz AK: Epidermal growth factor receptor and insulinlike growth factor 1 receptor expression predict poor survival in pancreatic ductal adenocarcinoma. Cancer 2012, 118(14):3484-3493.
Vicari D, Foy KC, Liotta EM, Kaumaya PT. Engineered conformation-dependent VEGF peptide mimics are effective in inhibiting VEGF signaling pathways. J. Biol. Chem. 286(15), 13612-13625 (2011).
Vinter-Jensen L. Pharmacological effects of epidermal growth factor (EGF) with focus on the urinary and gastrointestinal tracts. APMIS Suppl. 93, 1-42 (1999).
Walshe JM, Denduluri N, Berman AW, Rosing DR, Swain SM. A Phase II trial with trastuzumab and pertuzumab in patients with HER2-overexpressed locally advanced and metastatic breast cancer. Clin. Breast Cancer 6, 535-539 (2006).
Weber J. Peptide vaccines for cancer. Cancer Invest. 20, 208-221 (2002).
Weigand M, Hantel P, Kreienberg R, Waltenberger I: Autocrine vascular endothelial growth factor signalling in breast cancer. Evidence from cell lines and primary breast cancer cultures in vitro. Angiogenesis 2005, 8(3):197-204.
Wheeler DL, Huang S, Kruser TJ, Nechrebecki MM, Armstrong EA, Benavente S, Gondi V, Hsu KT, Harari PM: Mechanisms of acquired resistance to cetuximab: role of HER (ErbB) family members. Oncogene 2008, 27(28):3944-3956.
Wiedermann U, Wiltschke C, Jasinska I et al. A virosomal formulated Her-2/neu multipeptide vaccine induces Her-2/neu-specific immune responses in patients with metastatic breast cancer: a Phase I study. Breast Cancer Res. Treat. 119, 673-683 (2010).
Woodburn JR: The epidermal growth factor receptor and its inhibition in cancer therapy. Pharmacol Ther 1999, 82(2-3):241-250.
Wu X, Zhao H, Do KA et al. Serum levels of insulin growth factor (IGF-I) and IGFbinding protein predict risk of second primary tumors in patients with head and neck cancer. Clin. Cancer Res. 10, 3988-3995 (2004).
Yakar S, Leroith D, Brodt P. The role of the growth hormone/insulin-like growth factor axis in tumor growth and progression: lessons from animal models. Cytokine Growth Factor Rev. 16, 407-420 (2005).
Yang X, Qu L, Wang X, Zhao M, Li W, Hua J, Shi M, Moldovan NI, H. Wang, Z. Dou. Plasticity of epidermal adult stem cells derived from adult goat ear skin. Mol. Reprod. Dev. 2007, 74:386-96.
Yano T, Doi T Ohtsu A et al. Comparison of HER2 gene amplification assessed by fluorescence in situ hybridization and HER2 protein expression assessed by immunohistochemistry in gastric cancer. Oncol. Rep. 15, 65-71 (2006).
Yang X, Moldovan NI, Qu L, Wang X, Zhao M, Li W, Hua J, Shi M, Wang H, Dou Z. Epidermal adult stem cells possess the capacity to activate corneal genetic programs in response to corneal stromal stimuli. Mol Vis. 2008;14:1064-70.
Yen L, You XL, Al Moustafa AE et al. Heregulin selectively upregulates vascular endothelial growth factor secretion in cancer cells and stimulates angiogenesis. Oncogene 19, 3460-3469 (2000).
Yen, L., et al., Differential regulation of tumor angiogenesis by distinct ErbB homo- and heterodimers. Mol Biol Cell, 2002. 13(11): p. 4029-44.
Yip YL, Smith G, Koch J, Dubel S, Ward RL. Identification of epitope regions recognized by tumor inhibitory and stimulatory anti-ErbB-2 monoclonal antibodies: implications for vaccine design. J. Immunol. 166, 5271-5278 (2001).
Yu H, Spitz MR, Mistry J, Gu J, Hong WK, Wu X. Plasma levels of insulin-like growth factor-I and lung cancer risk: a case-control analysis. J. Natl Cancer Inst. 91, 151-156 (1999).
Zabuawala T, Taffany DA, Sharma SM et al. An ets2-driven transcriptional program in tumor-associated macrophages promotes tumor metastasis. Cancer Res. 70, 1323-1333 (2010).
Zhu Z, Witte L. Inhibition of tumor growth and metastasis by targeting tumor-associated angiogenesis with antagonists to the receptors of vascular endothelial growth factor. Invest. N. Drugs 17, 195-212 (1999).
Alimandi M, Romano A, Curia MC et al. Cooperative signaling of Erbb3 and Erbb2 in 61. neoplastic transformation and human mammary carcinomas. Oncogene 10, 1813-1821 (1995).
Sundberg EJ, Mariuzza RA: Molecular recognition in antibody-antigen complexes. Adv Protein Chem 2002, 61:119-160.
Amler L, Makhija S, Januano T et al. Downregulation of HER3 may predict clinical benefit in ovarian cancer from pertuzumab, a HER2 dimerization-inhibiting antibody. Presented at: ASCO-NCI-EORTC Annual Meeting on Molecular Markers in Cancer. Abstract 25 (2008).
Chow NH, Liu HS, Lee EI et al. Significance of urinary epidermal growth factor and its receptor expression in human bladder cancer. Anticancer Res. 17, 1293-1296 (1997).
Dong M, Nio Y, Guo KJ, Tamura K, Tian YL, Dong YT: Epidermal growth factor and its receptor as prognostic indicators in Chinese patients with pancreatic cancer. Anticancer Res 1998, 18(68):4613-4619.
Fischer PM. The design, synthesis and application of stereochemical and directional peptide isomers: a critical review. Curr. Protein Peptide Sci. 4, 339-356 (2003).

(56) References Cited

OTHER PUBLICATIONS

Fisk B, Hudson JM, Kavanagh J et al. Existent proliferative responses of peripheral blood mononuclear cells from healthy donors and ovarian cancer patients to HER-2 peptides. Anticancer Res. 17, 45-53 (1997).
Goodman M, Ro S, Yamazaki T et al. Topochemical design of bioactive peptides and peptidomimetics. Bioorg. Khim. 18, 1375-1393 (1992).
Kaumaya et al., "De Novo" Engineering of Peptide Immunogenic and Antigenic Determinants as Potential Vaccines. In Peptides, Design, Synthesis and Biological Activity Anantharamaiah GM (Ed.). Springer-Verlag, Berlin, Germany, 133-164 (1994).
Pollak MN. Insulin-like growth factors and neoplasia. Novartis Found. Symp. 262, 84-98 Discussion 98-107, 265-268 (2004).
Wang Y, Sun Y: Insulin-like growth factor receptor-1 as an anti-cancer target: blocking transformation and inducing apoptosis. Curr Cancer Drug Targets 2002, 2(3):191-207.
Schaefer et al., Cancer Cell 20:472-486.

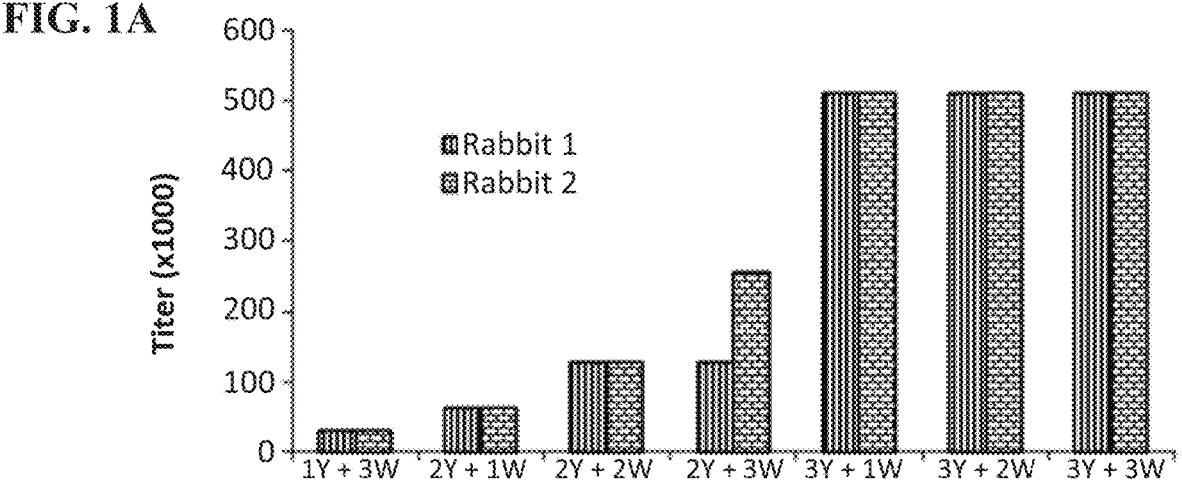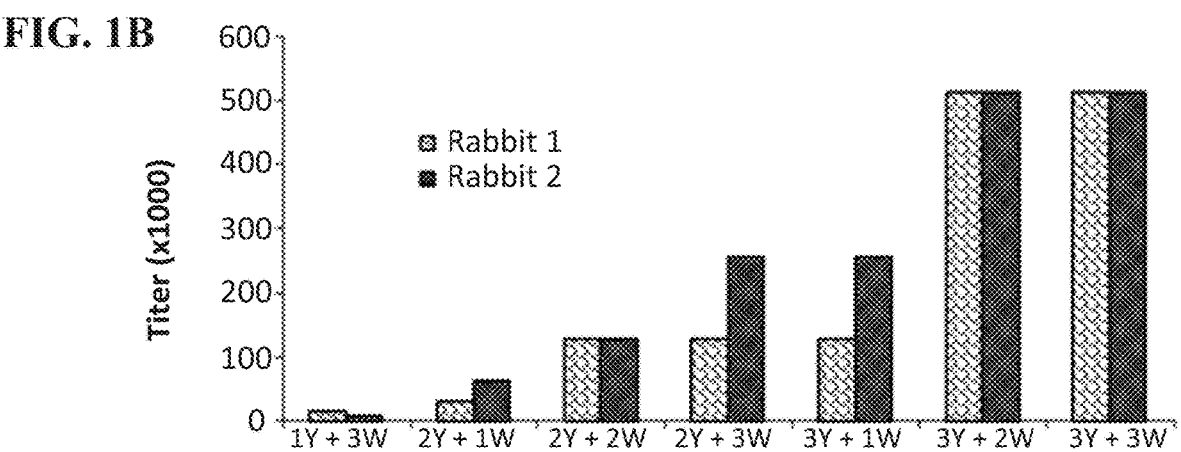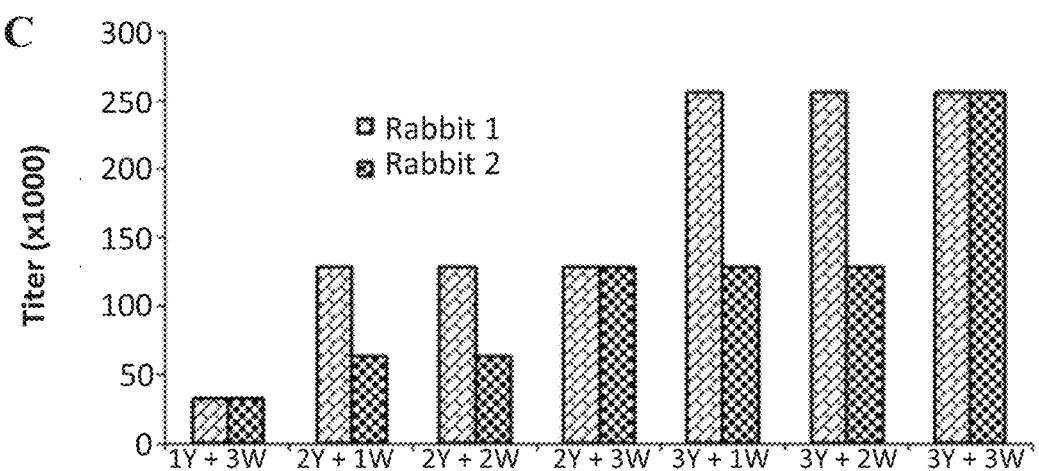

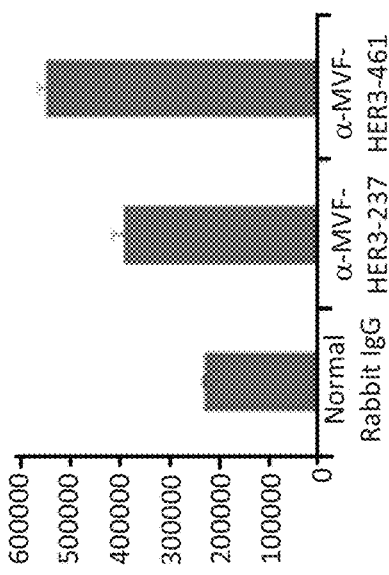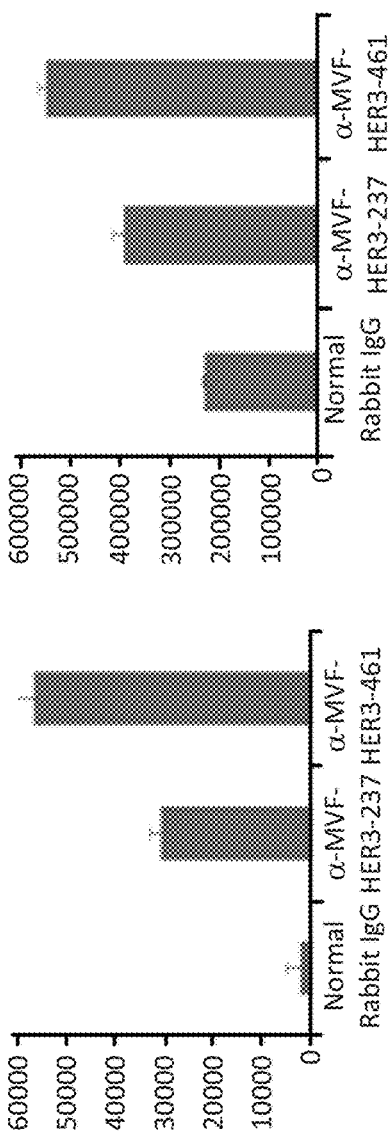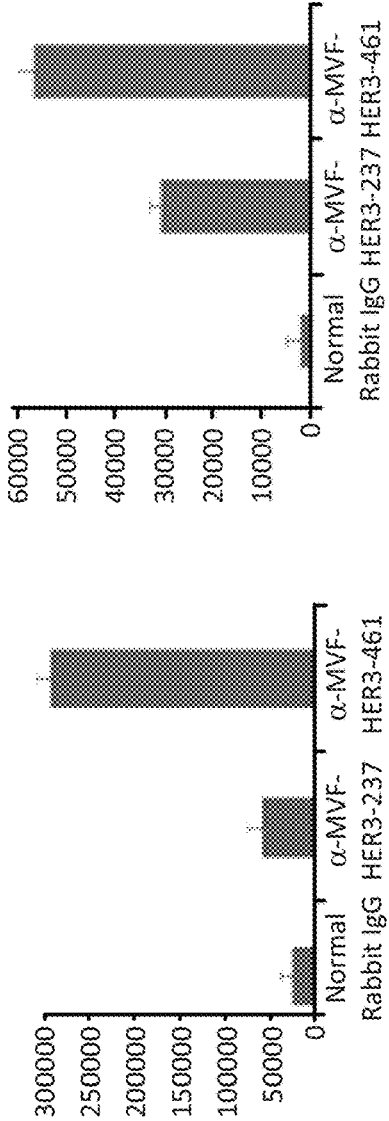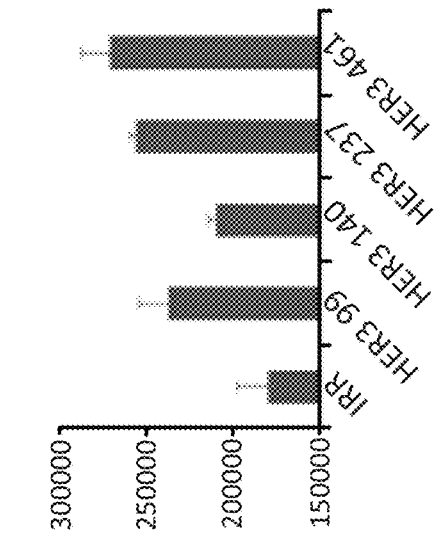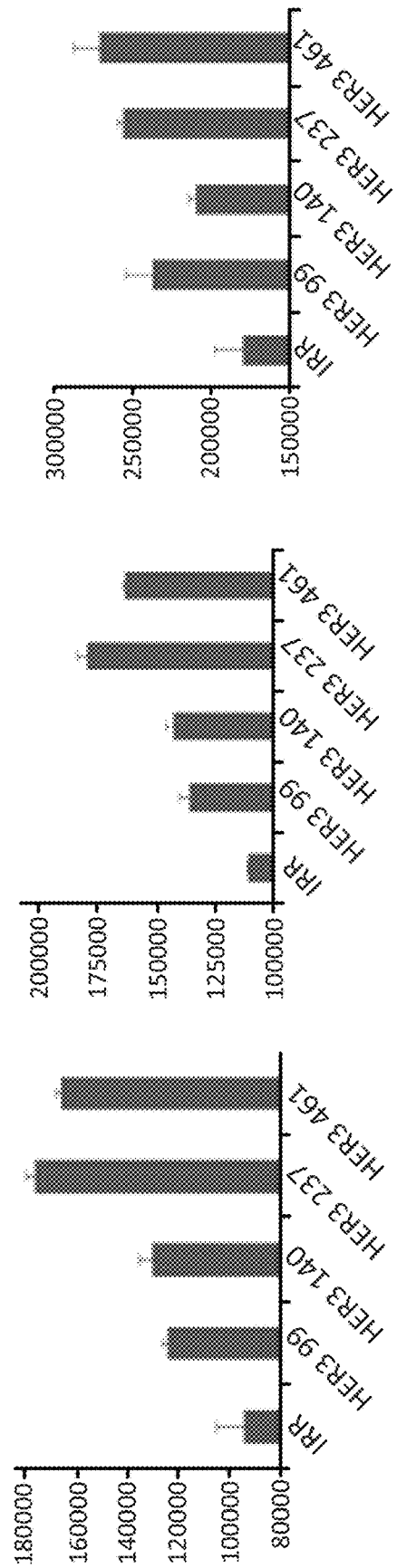
FIG. 14A  FIG. 14B  FIG. 14C  FIG. 14D  FIG. 14E  FIG. 14F

# HER-1, HER-3 AND IGF-1R COMPOSITIONS AND USES THEREOF

CROSS REFERENCE TO RELATED APPLICATIONS

This application is a divisional of and claim priority to U.S. application Ser. No. 14/770,335, filed on Aug. 25, 2015, which is a national stage application filed under 35 USC § 371 of PCT Application No. PCT/US2014/018354, filed on Feb. 25, 2014 which claims the benefit of U.S. Provisional Patent Application Ser. No. 61/768,881 filed Feb. 25, 2013 and U.S. Provisional Patent Application Ser. No. 61/778,766 filed Mar. 13, 2013. Each of these applications is hereby incorporated by reference in their entirety.

FIELD OF THE INVENTION

The application is generally related to HER-1, HER-3 and IGF-1R compositions and methods of their use.

BACKGROUND

Epidermal growth factor receptor (EGFR or HER-1) is central to human tumorigenesis, and dysregulation of this receptor is mainly due to increased expression [Arteaga, C. L. 2002. Semin. Oncol. 29(Suppl 14):3-9] and mutations in different domains of the receptor [Boerner, J. L., A. Danielsen, and N. J. Maihle. 2003. Exp. Cell Res. 284: 111-121]. HER-1 is overexpressed in most epithelial cancers including breast/triple-negative breast cancer (TNBC; 14-90%) [Gluz, O., et. al. 2009. Ann. Oncol. 20: 1913-1927, Pintens, S., et al. 2009. J. Clin. Pathol. 62: 624-628], non-small cell lung (40-80%) [Hirsch, F. R., et al. 2003. J. Clin. Oncol. 21: 3798-3807], head and neck (80-100%), colorectal (25-77%), and other cancers. HER-1 overexpression in tumors is responsible for aggressiveness, poor prognosis, decreased survival, poor response to therapy, and development of resistance [Arteaga, C. L., and J. Baselga. 2004. Cancer Cell 5: 525-531]. HER-1 forms heterodimers with other human epidermal growth factor receptor (HER) family members like HER-2, HER-3, and HER-4 resulting in aggressive forms of cancer with lower survival rates [Brabender, et al. 2001. Clin. Cancer Res. 7: 1850-1855].

The development of antibodies targeting HER-1 is mainly dependent on structural studies that help outline the details of the receptors and other conformational changes affecting its activation and downstream signaling. HER-1 signaling is highly dependent on ligand binding, which is a key factor in releasing the dimerization arm of the receptors [Ferguson, K. M., et al. 2003. Mol. Cell 11: 507-51], and this explains why many of the anti-HER-1 antibodies are directed toward the ligand-binding region. Cetuximab, a humanized mAb, binds HER-1, prevents ligand binding, and is Food and Drug Administration—approved for the treatment of metastatic colorectal cancers with high HER-1 expression [Li, S., et al. 2005. Cancer Cell 7: 301-311]. However, the emergence of resistance to cetuximab has led to the proposal that other mechanisms exist that are independent of ligand binding, and this has led to the development of other antibodies with key epitopes that are different from cetuximab. For instance, activation of other HER family receptors may help in the stabilization of HER-1 even in the absence of ligand binding [Sawano, A., et al. 2002. Dev. Cell 3: 245-257].

Further, mAbs have additional limitations such as repeated frequency of i.v. treatments and infusion reactions that can be lethal in some patients [Grothey, A. 2006. Oncology (Huntingt.) 20(Suppl 10): 21-28]. Inhibition of metastasis by these agents has been shown to be nonspecific in both preclinical and clinical settings, and the toxicity caused by these agents clearly illustrates the potential risks of their continuous use in the clinic. Given these caveats, there is an urgent unmet need for developing more efficacious, safer, and less toxic anti-HER-1 agents.

Like HER-1, HER-3 (ErbB3) is a member of the human epidermal growth factor family of receptors. Efforts at targeting HER-3 have lagged behind the other members of this family, due in part to its impaired kinase activity. However, several recent studies have shown that HER-3 may be an attractive target against many types of cancer. HER-3 is frequently up-modulated in cancers with HER-1 or HER-2 overexpression, and HER-3 may provide a route for resistance to agents that target EGFR or HER-2. Currently, therapeutic monoclonal antibodies such as AMG 888 and MM-121 specifically target HER-3 and are currently being evaluated in clinical trials. Yet again, great limitations exist with TKIs and monoclonal antibodies, including: severe toxicities, repeated treatments, high costs, development of resistance, and limited duration of action.

Apart from the HER family receptors, the insulin-like growth factor (IGF-1R) has also emerged as a key regulator of tumorigenesis in colorectal cancer [Lu Y., et al. International Journal of Cancer 2004, 108(3):334-341, Haluska P, et al. 2008. Molecular Cancer Therapeutics 7(9):2589-2598]. Accordingly, there is a need for new agents that target HER-1, HER-3 and IGF-1R for the treatment of cancer.

SUMMARY OF THE INVENTION

Provided herein is a HER-1 chimeric peptide for stimulating an immune response to a HER-1 protein comprising one or more HER-1 B cell epitopes, a T helper (Th) epitope, and a linker joining the HER-1 B cell epitope to the Th epitope. In some embodiments, the one or more HER-1 B cell epitopes consist of a sequence selected from the group consisting of: SEQ ID NO: 1, SEQ ID NO: 2, and SEQ ID NO: 3. The Th epitope comprises a sequence selected from the group consisting of: SEQ ID NO: 12, SEQ ID NO:13, SEQ ID NO: 14, SEQ ID NO: 15, SEQ ID NO: 16 SEQ ID NO: 17, SEQ ID NO: 18, and SEQ ID NO:19 and the linker comprises a sequence that is from 1 to 15 amino acids in length. In one embodiment, the Th epitope comprises SEQ ID NO:17. In another or further embodiment, the linker comprises SEQ ID NO:20.

Also provided herein is a HER-3 chimeric peptide for stimulating an immune response to a HER-3 protein comprising one or more HER-3 B cell epitopes, a Th epitope, and a linker joining the HER-3 B cell epitope to the Th epitope. In some embodiments, the one or more HER-3 B cell epitopes consist of a sequence selected from the group consisting of SEQ ID NO:4, SEQ ID NO:5, SEQ ID NO:6, and SEQ ID NO:7. The Th epitope and linker may be those indicated above.

Further provided herein is an IGF-1R chimeric peptide for stimulating an immune response to an IGF-1R protein comprising one or more IGF-1R B cell epitopes, a Th epitope, and a linker joining the IGF-1R B cell epitope to the Th epitope. In some embodiments, the one or more IGF-1R B cell epitopes consist of a sequence selected from the group consisting of SEQ ID NO:8, SEQ ID NO:9, SEQ ID NO:10, and SEQ ID NO:11. The Th epitope and linker may be those indicated above.

The HER-1, HER-3 and IGF-1R chimeric peptides are also provided in a pharmaceutical composition including a pharmaceutically acceptable vehicle. The pharmaceutical composition can further contain one or more HER-2 B cell epitopes, a second Th epitope, and a linker joining the HER-2 B cell epitope to the Th epitope. The one or more HER-2 B cell epitopes may be selected from the group consisting of: SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO:40. The pharmaceutical composition may also or optionally contain a VEGF peptide selected from the group consisting of: SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, and SEQ ID NO:54.

The vehicle of the pharmaceutical composition is preferably biodegradable and is selected from the group consisting of an emulsion comprising a pharmaceutically acceptable oil/water emulsion and a biodegradable microsphere or nanosphere comprising a polylactide-polyglycolic acid polymer. The oil in the oil/water emulsion may be squalene or squalene. The microsphere may be from 0.1 to 50 nanometers in diameter and comprises poly (D, L lactide-co-glycide).

A surprising finding of the present invention is that the HER-1, HER-3 and IGF-1R chimeric peptides may be used to stimulate an immune response to a HER-1, HER-3 and IGF-1R protein, respectively, in a subject. Accordingly, included herein are methods of using the HER-1, HER-3 and IGF-1R chimeric peptides to stimulate an immune response in a subject. Also provided are methods of treating a cancer using the HER-1, HER-3 and IGF-1R chimeric peptides. In some embodiments, the cancer is selected from breast cancer, ovarian cancer, lung cancer, prostate cancer, and colon cancer. These methods include administration of a combination of different HER-1, HER-3 and IGF-1R chimeric peptides, and optionally, HER-2 chimeric peptides and/or VEGF peptides. Such combination treatments provide even more surprising synergistic treatment results.

BRIEF DESCRIPTION OF THE FIGURES

FIG. 14 (A-F) contains graphs showing apoptosis of cells treated with HER-3 anti-peptide antibodies (A-C) or HER-3 peptide mimics (D-F) wherein the y axis shows luminescence (RLU) and the x-axis shows peptide mimics at 150 µg/ml.

DETAILED DESCRIPTION OF THE INVENTION

Figure 1D:
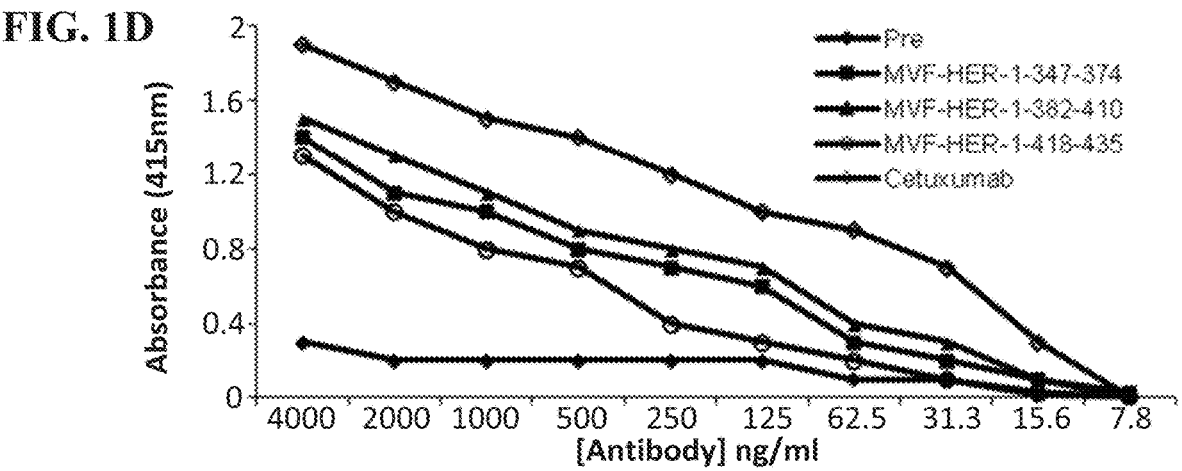
FIG. 1 (A-F) contains graphs showing the immunogenicity of EGFR (HER-1) peptide vaccine in outbred rabbits and antiproliferative effects in rabbit Abs and chimeric peptides. (A-C) Relative levels of vaccine Abs measured in an ELISA assay showing immunogenicity of peptide constructs in rabbits (two per each construct). 2y+3w, for example, indicates the titer of blood drawn 3 weeks after the second immunization. (D) Binding of vaccine Abs to rhEGFR. y-axis represents absorbance, which shows levels of binding. MTT cell proliferation assay with breast and lung cancer cells using 50 mg/ml of vaccine Abs (E) and 50 mg/ml of peptide mimics (F) as inhibitors. The percentage inhibition was calculated using the formula (ODUNTREATED−ODTREATED)/ODUNTREATED×100, and data shown represent an average of three different experiments, with error bars showing SD from the mean.

Provided herein are HER-3, HER-1 and IGF-1R B cell epitopes, peptide mimics, chimeric peptides and multivalent peptides. The peptide mimics include one or more HER-3, HER-1 and/or IGF-1R B cell epitopes and are acetylated and amidated at the amino and carboxyl termini. The chimeric peptides include one or more HER-3, HER-1 and/or IGF-1R B cell epitopes, a linker, and a T helper cell (Th cell) epitope. Pharmaceutical compositions are also provided that contain one or more HER-3, HER-1 and/or IGF-1R peptide mimics or chimeric peptides, and optionally, one or more HER-2 chimeric peptides and/or VEGF peptide mimics. It is a surprising finding of the present invention that these peptides and compositions may be used in the treatment of cancer. Accordingly, also included herein are methods of treating a cancer using the HER-3, HER-1 and IGF-1R B cell epitopes, peptide mimics, chimeric peptides and multivalent peptides. Terms used throughout this application are to be construed with ordinary and typical meaning to those of ordinary skill in the art. However, Applicants desire that the following terms be given the particular definition provided below.

I. Definitions

As used in the specification and the appended claims, the singular forms "a," "an" and "the" include plural referents unless the context clearly dictates otherwise.

The term "about" as used herein means greater or lesser than the value or range of values stated by 1/10 of the stated values, but is not intended to limit any value or range of values to only this broader definition. Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats, and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "administering" refers to an administration that is oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. Embodiments defined by each of these transition terms are within the scope of this invention.

An "effective amount" is an amount sufficient to effect beneficial or desired results. An effective amount can be administered in one or more administrations, applications or dosages.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. "Overexpression" as applied to a gene, refers to the overproduction of the mRNA transcribed from the gene or the protein product encoded by the gene, at a level that is 2.5 times higher, preferably 5 times higher, more preferably 10 times higher than the expression level detected in a control sample.

As used herein, the terms "neoplastic cells," "neoplasia," "tumor," "tumor cells," "cancer," and "cancer cells" (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign. A metastatic cell or tissue means that the cell can invade and destroy neighboring body structures.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SCI., 15th Ed. (Mack Publ. Co., Easton (1975)).

The term "pharmaceutically acceptable carrier or excipient" includes a carrier or excipient that is useful in preparing a pharmaceutical composition that is generally safe, nontoxic and neither biologically nor otherwise undesirable, and further includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount", "therapeutically effective amount" or "therapeutically effective dose" are used interchangeably and refer to the amount of a compound such as a HER-1 chimeric peptide, a HER-3 chimeric peptide or an IGF-1R chimeric peptide that will elicit the biological or medical response of a tissue, system, animal, or human that is being sought by the researcher, veterinarian, medical doctor or other clinician. The pharmaceutically effective amount will vary depending on the compound such as a HER-1 chimeric peptide, a HER-3 chimeric peptide or an IGF-1R chimeric peptide, the disorder or condition and its severity, the route of administration, time of administration, rate of excretion, drug combination, judgment of the treating physician, dosage form, and the age, weight, general health, sex and/or diet of the subject to be treated.

The terms "treat", "treating", "treatment" and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, pallatively or remedially. In some instances, the terms "treat", "treating", "treatment" and grammatical variations thereof, include partially or completely reducing the size of a tumor, reducing the number of tumors, and reducing the severity/metastatic ability of a tumor as compared with prior to treatment of the subject or as compared with the incidence of such symptom in a general or study population.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound. As used herein, a "wt. %" or "weight percent" or "percent by weight" of a component, unless specifically stated to the contrary, refers to the ratio of the weight of the component to the total weight of the composition in which the component is included, expressed as a percentage.

II. Compositions

HER-1, HER-3 and IGF-1R Epitopes

The present invention provides new compositions for stimulating the immune system and for treating malignancies associated with over-expression or over-activation of the HER-1, HER-3 and/or IGF-R1 protein. The compounds are immunogenic B cell epitopes of the HER-1, HER-3 and/or IGF-R1 protein, and chimeric and multivalent peptides which comprise such epitopes.

As mentioned above, the HER-1 protein is also known as epidermal growth factor receptor (EGFR) and ErbB-1. HER-1 is a transmembrane glycoprotein that is a member of the protein kinase superfamily that binds to epidermal growth factor. Binding of the protein to a ligand induces receptor dimerization and tyrosine autophosphorylation and leads to cell proliferation. Multiple alternatively spliced transcript variants that encode different protein isoforms have been found for this gene. The amino acid sequence of one HER-1 protein is shown in GenBank Accession No. AAH94761. One of skill in the art is aware that additional information regarding HER-1, its various isoforms, and the one or more genes that encode the protein and/or isoforms can be found associated with the following identifiers: HGNC: 3236' Entrez Gene: 1956, Ensembl: ENSG00000146648, OMIM: 131550, and UniProtKB: P00533. It should be understood that the term "HER-1" encompasses all such proteins, isoforms and genes.

The HER-1 B cell epitopes provided herein comprise from about 15 to about 50 amino acids, more preferably from 17 to 40 amino acids, most preferably from 18 to 35 amino acids of HER-1. Preferably, the HER-1 B cell epitope comprises a sequence selected from the following group listed in Table 1 or a functional equivalent thereof:

TABLE 1

| Peptide Designation | Sequence | SEQ ID NO: |
|---|---|---|
| HER-1 (347-374) | ILPVAFRGDSFTHTPPLDPQELDILKTV | 1 |
| HER-1 (382-410) | LIQAWPENRTDLHAFENLEIIRGRTKQHG | 2 |
| HER-1 (418-435) | SLNITSLGLRSLKEISDG | 3 |

The HER-1 B cell epitopes listed above and their functional equivalents have the ability to induce production of antibodies which are immunoreactive with the extracellular domain of the HER-1 protein. Also included herein are HER-1 peptide mimics that comprise one or more HER-1 B cell epitopes and are acetylated at one peptide terminus and amidated at the other peptide terminus.

As noted above, the HER-3 protein is a member of the epidermal growth factor receptor (EGFR) family of receptor tyrosine kinases and is also known as ErbB-3. This membrane-bound protein has a neuregulin binding domain but not an active kinase domain. It therefore can bind this ligand but not convey the signal into the cell through protein phosphorylation. However, it does form heterodimers with other EGF receptor family members which do have kinase activity. Heterodimerization leads to the activation of pathways which lead to cell proliferation or differentiation. Amplification of this gene and/or overexpression of its protein have been reported in numerous cancers, including prostate, bladder, and breast tumors. Alternate transcriptional splice variants encoding different isoforms have been characterized. One of skill in the art is aware that additional information regarding HER-3, its various isoforms, and the one or more genes that encode the protein and/or isoforms can be found associated with the following identifiers: HGNC: 3431, Entrez Gene: 2065, OMIM: 190151, Ensembl: ENSG00000065361, and UniProtKB: P21860. It should be understood that the term "HER-3" encompasses all such proteins, isoforms, and genes.

The HER-3 B cell epitopes provided herein comprise from about 15 to about 50 amino acids, more preferably from 17 to 40 amino acids, most preferably from 18 to 35 amino acids of HER-3. Preferably, the HER-3 B cell epitope comprises a sequence selected from the following group listed in Table 2 or a functional equivalent thereof:

TABLE 2

| Peptide Designation | Sequence | SEQ ID NO: |
|---|---|---|
| HER-3 (237-269) | VPRCPQPLVYNKLTFQLEPNPHTKYQYGGVCVA | 4 |
| HER-3 (461-479) | ERLDIKHNRPRRDCVAEGK | 5 |
| HER-3 (99-122) | FVMLNYNTNSSHALRQLRLTQLTE | 6 |
| HER-3 (140-162) | DTIDWRDIVRDRDAEIVVKDNGR | 7 |

The HER-3 B cell epitopes listed above and their functional equivalents have the ability to induce production of antibodies which are immunoreactive with the extracellular domain of the HER-3 protein. Also included herein are HER-3 peptide mimics that comprise one or more HER-3 B cell epitopes and are acetylated at one peptide terminus and amidated at the other peptide terminus.

The IGF-1R protein binds IGF-1 with high affinity and IGF2 and insulin (INS) with a lower affinity. The activated IGF-1R is involved in cell growth and survival control. IGF-1R is crucial for tumor transformation and survival of malignant cells. Ligand binding activates the receptor kinase, leading to receptor autophosphorylation, and tyrosines phosphorylation of multiple substrates, that function as signaling adapter proteins including, the insulin-receptor substrates (IRS1/2), Shc and 14-3-3 proteins. One of skill in the art is aware that additional information regarding IGF-1R, its various isoforms, and the one or more genes that encode the protein and/or isoforms can be found associated with the following identifiers: HGNC: 5465, Entrez Gene: 3480, Ensembl: ENSG00000140443' OMIM: 1473705, and UniProtKB: P08069. It should be understood that the term "IGF-1R" encompasses all such proteins, isoforms and genes.

The IGF-1R B cell epitopes provided herein comprise from about 15 to about 50 amino acids, more preferably from 17 to 40 amino acids, most preferably from 18 to 35 amino acids of IGF-1R. Preferably, the IGF-1R B cell epitope comprises a sequence selected from the following group listed in Table 3 or a functional equivalent thereof:

TABLE 3

| Peptide Designation | Sequence | SEQ ID NO: |
|---|---|---|
| IGF-1R (6-26) | GIDIRNDYQQLKRLENCTVIE | 8 |
| IGF-1R (26-42) | EGYLHILLISKAEDYRSYRF | 9 |
| IGF-1R (56-81) | LLFRVAGLESLGDLFPNLTVIRGWKL | 10 |
| IGF-1R (234-252) | ACPPNTYRFEGWRCVDRDF | 11 |

The IGF-1R B cell epitopes listed above and their functional equivalents have the ability to induce production of antibodies which are immunoreactive with the extracellular domain of the IGF-1R protein. Also included herein are IGF-1R peptide mimics that comprise one or more IGF-1R B cell epitopes and are acetylated at one peptide terminus and amidated at the other peptide terminus.

As described herein, the HER-1, HER-3 and/or IGF-R1 B cell epitopes also encompass peptides that are functional equivalents of the epitopes shown in Table 1, 2 or 3 above. Such functional equivalents have an altered sequence in which one or more of the amino acids in the corresponding reference sequence is substituted or in which one or more amino acids are deleted from or added to the corresponding HER-1, HER-3 and/or IGF-R1 sequence shown in Table 1, 2 or 3 above. For example, cysteine residues may be deleted or replaced with other amino acids to prevent formation of incorrect intramolecular disulfide bridges upon renaturation. Optionally, the peptide epitopes shown in Table 1, 2 or 3 above are glycosylated.

While it is possible to have non-conservative amino acid substitutions, it is preferred that, except for the substitutions that are made to replace cysteine, the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g., alanine, valine, leucine and isoleucine, with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, methionine, and glycine, with another.

Preferably, the deletions and additions are located at the amino terminus, the carboxy terminus, or both, of one of the sequences shown in Table 1, 2 or 3 above. As a result of the alterations, the HER-1, HER-3 and/or IGF-R1 B cell epitope equivalent has an amino acid sequence which is at least 70% identical, preferably at least 80% identical, more preferably at least 90% identical, most preferably, at least 95% identical to the corresponding sequences shown in Table 1, 2 or 3. Sequences which are at least 90% identical have no more than 1 alteration, i.e., any combination of deletions, additions or substitutions, per 10 amino acids of the reference sequence. Percent identity is determined by comparing the amino acid sequence of the variant with the reference sequence using MEGALIGN project in the DNA STAR program.

For functional equivalents that are longer than a corresponding sequence shown in Table 1, 2 or 3, it is preferred that the functional equivalent have a sequence which is at least 90% identical to the reference sequence and the sequences which flank the reference sequence in the wild-type HER-1, HER-3 and/or IGF-R1 protein.

HER-1, HER-3 and IGF-1R Chimeric and Multivalent Peptides

The present invention also provides chimeric peptides, referred to hereinafter as "chimeric HER-1 B cell peptides," "chimeric HER-3 B cell peptides," or "chimeric IGF-1R B cell peptides" which comprise at least one of the present HER-1, HER-3 or IGF-1R B cell epitopes, respectively, or a functional equivalent thereof. Preferably the chimeric HER-1, HER-3 or IGF-1R B cell peptides are from about 35 to about 150, more preferably from about 35 to about 70 amino acids in length. In some embodiments, the chimeric HER-1, HER-3 or IGF-1R B cell peptides comprise three units. The first unit comprises the HER-1, HER-3 and/or IGF-1R B cell epitope or a functional equivalent thereof. The second unit is a helper T (Th) cell epitope, preferably a promiscuous Th cell epitope. As used herein a "promiscuous" Th cell epitope is one which promotes release of cytokines that assist in bypassing MEW restriction. The second unit is from about 14 to about 22, more preferably about 15 to 21, most preferably 16 amino acids in length. Preferably, the Th cell epitope has one of the following amino acid sequences provided in Table 4.

TABLE 4

| Peptide Designation | Sequence | SEQ ID NO: |
|---|---|---|
| MVF | KLLSLIKGVIVHRLEGVE | 12 |
| TT | NSVDDALINSTIYSYFPSV | 13 |
| TT1 | PGINGKAIHLVNNQSSE | 14 |

TABLE 4-continued

| Peptide Designation | Sequence | SEQ ID NO: |
|---|---|---|
| P2 | QYIKANSKFIGITEL | 15 |
| P30 | FNNFTVSFWLRVPKVSASHLE | 16 |
| MVF (natural) | LSEIKGVIVHRLEGV | 17 |
| HBV | FFLLTRILTIPQSLN | 18 |
| CSP | TCGVGVRVRSRVNAANKKPE | 19 |

The third unit joins the first and second peptide units. The third unit is an amino acid or, preferably, a peptide of from about 2 to about 15 amino acids, more preferably from about 2 to about 10 amino acids, most preferably from about 2 to about 6 amino acids in length. The most preferred linker comprises the amino acid sequence Gly-Pro-Ser-Leu (SEQ ID NO: 20).

Accordingly, the present invention provides chimeric peptides which comprise a HER-1, HER-3 and/or IGF-1R B cell epitope, a helper T (Th) cell epitope, preferably a promiscuous Th cell epitope, and a linker. Depending upon the promiscuous Th cell epitope used, the HER-1, HER-3 and/or IGF-1R B cell epitope is linked to either the amino or the carboxy terminus of the Th cell epitope. The location and selection of the Th cell epitope depends on the structural characteristics of the B cell epitope (whether alpha helical or beta-turn or strand). Methods for selecting suitable Th cell epitopes are described in Kaumaya et al., "De Novo" Engineering of Peptide Immunogenic and Antigenic Determinants as Potential Vaccines, in Peptides, Design, Synthesis and Biological Activity (1994), pp. 133-164, which is specifically incorporated herein by reference. A summary of the immune responses elicited a variety of promiscuous T-helper cell epitope containing B-cell epitope chimeras was presented in a review titled "Synthetic Peptides: Dream or Reality" by Kaumaya et al., and published in Peptides in Immunology, Wiley and Sons, Ltd. (1996).

Further provided herein are chimeric peptides which comprise one or more HER-1, HER-3 and/or IGF-1R B cell epitopes, a helper T (Th) cell epitope, preferably a promiscuous Th cell epitope, and a linker. In some embodiments, the chimeric peptide comprises one or more HER-1 B cell epitopes, a Th cell epitope and a linker. In other embodiments, the chimeric peptide comprises one or more HER-3 B cell epitopes, a Th cell epitope and a linker. In still other embodiments, the chimeric peptide comprises one or more IGF-1R B cell epitopes, a Th cell epitope and a linker. Also included herein are chimeric peptides comprising a Th cell epitope, a linker and at least two of a HER-1 B cell epitope, a HER-3 B cell epitope, and an IGF-1R B cell epitope.

The present invention also provides multivalent HER-1, HER-3 and IGF-1R B cell peptides which comprise a plurality, i.e., at least two of the present HER-1, HER-3 and/or IGF-1R B cell epitopes or functional equivalents thereof and a Th cell epitope, wherein the HER-1, HER-3 and/or IGF-1R B cell epitopes and Th cell epitope are connected to a core template. Preferably, the template comprises two strands of alternating leucine and lysine residues, which are connected by a linker. The linker is an amino acid or, preferably, a peptide of from about 2 to about 15 amino acids, more preferably from about 2 to about 10 amino acids, most preferably from about 2 to about 6 amino acids in length. The most preferred linker comprises the amino acid sequence GPSL (SEQ ID NO: 20).

It should also be understood that any of the chimeric peptides or epitopes provided herein can be in the retro-inverso form. The retro-inverso modification comprises the reversal of all amide bonds within the peptide backbone. The reversal may be achieved by reversing the direction of the sequence and inverting the chirality of each amino acid residue using D-amino acids instead of L-amino acids. This retro-inverso form may retain planarity and conformation restriction of at least some of the peptide bonds.

The chimeric and multivalent peptides described herein can also be included in a pharmaceutical composition for administration to a subject. Pharmaceutical compositions which comprise the chimeric or multivalent HER-1, HER-3 and/or IGF-1R B cell peptides or the polynucleotides which encode the same are include herein. Such compositions generally comprise one or more of the chimeric or multivalent HER-1, HER-3 and/or IGF-1R B cell peptides or the polynucleotides which encode the same in combination with a pharmaceutically acceptable carrier, excipient or diluent. Such carriers will be nontoxic to the subject to which the pharmaceutical composition is administered at the dosages and concentrations employed. These pharmaceutical compositions may be formulated as a vaccine composition.

In some embodiments, the pharmaceutical composition comprises chimeric or multivalent HER-1, HER-3 and/or IGF-1R B cell peptides and one or more HER-2 epitopes or HER-2 chimeric or multivalent peptides. The HER-2 chimeric or multivalent peptides comprise a HER-2 epitope, a Th cell epitope and a linker. The HER-2 epitopes and HER-2 chimeric peptides can be any previously described in U.S. Pat. Nos. 7,060,284; 7,666,430; 7,691,396; 8,110,657; and 8,470,333 and U.S. Patent Application Publication Nos. 2010/0234283, 2012/0201841, and 2014/0010831. Each of these references is hereby incorporated by reference in its entirety. HER-2 B cell epitopes are also provided below in Table 5.

TABLE 5

| Peptide Designation | Sequence | SEQ ID NO: |
|---|---|---|
| HER-2 (563-598) | CHPECQPQNGSVTCFGPEADQCVACAHYKDPPFCVA | 21 |
| HER-2 (585-598) | VACAHYKDPPFCVA | 22 |
| HER-2 (597-626) | VARCPSGVKPDLSYMPIWKFPDEEGACQPL | 23 |
| HER-2 (613-626) | IWKFPDEEGACQPL | 24 |
| HER-2 (315-333) | LHCPALVTYNTDTFESMPNPEGRYTFGASCV | 25 |
| HER-2 (298-333) | ACPYNYLSTDVGSCTLVCPLHNQEVTAEDGTQRCEK | 26 |
| HER-2 (266-296) | CPLHNQEVTAEDGTQRCEK | 27 |
| HER-2 (626-649) | CPINCTHSCVDLDDKGCPAEQRAS | 28 |
| HER-2 (27-45) | TGTDMKLRLPASPETHLDM | 29 |
| HER-2 (115-136) | AVLDNGDPLNNTTPVTGASPGG | 30 |
| HER-2 (168-189) | LWKDIFHKNNQLALTLIDTNRS | 31 |
| HER-2 (182-216) | TLIDTNRSRACHPCSPMCKGSRCWGESSEDCQSLT | 32 |
| HER-2 (270-290) | ALVTYNTDTFESMPNPEGRYT | 33 |

TABLE 5-continued

| Peptide Designation | Sequence | SEQ ID NO: |
|---|---|---|
| HER-2 (316-339) | PLHNQEVTAEDGTQRAEKCSKPCA | 34 |
| HER-2 (376-395) | PESFDGDPASNTAPLQPE | 35 |
| HER-2 (410-429) | LYISAWPDSLPDLSVFQNLQ | 36 |
| HER-2 (485-503) | LFRNPHQALLHTANRPEDE | 37 |
| HER-2 (560-593) | CLPCHPECQPQNGSVTCFGPEADQCVACAHYKDP | 38 |
| HER-2 (605-622) | KPDLSYMPIWKFPDEEGA | 39 |
| HER-2 (628-647) | INGTHSCVDLDDKGCPAEQR | 40 |

The HER-2 B epitope identified by SEQ ID NO: 21 represents positions 563-598 of the HER-2 protein. The HER-2 B epitope identified by SEQ ID NO: 21 may be cyclized by the formation of a disulfide bonds between Cys-563 and Cys-576, Cys-567 and Cys-584, and/or Cys-587 and Cys-596. The HER-2 B epitope identified by SEQ ID NO: 22 represents positions 585-598. The HER-2 B epitope identified by SEQ ID NO: 22 may be cyclized by the formation of a disulfide bond between Cys-587 and Cys-596. The HER-2 B epitope identified by SEQ ID NO: 23 represents positions 597-626, and the underlined leucine (Leu) amino acid was mutated from Cys to Leu in order not to interfere with disulfide bond formation. The HER-2 B epitope identified by SEQ ID NO: 23 may be cyclized by the formation of a disulfide bond between Cys-600 and Cys-623. The HER-2 B epitope identified by SEQ ID NO: 24 represents positions 613-626, and the bold Leu amino acid was mutated from Cys to Leu in order not to interfere with disulfide bond formation as will be discussed further herein. It will be understood that the indicated Leu amino acids in SEQ ID NOs: 23 and 24 may alternatively be Cys.

The HER-2 B epitopes identified by SEQ ID NOs: 25-27 represent sequences designed to elicit antibody similar to the pertuzmab binding site of HER-2. The HER-2 B epitope identified by SEQ ID NO: 25 represents positions 315-333 of the HER-2 protein. The HER-2 B epitope identified by SEQ ID NO: 25 may be cyclized by the formation of a disulfide bond between Cys-315 and Cys-331. The HER-2 B epitope identified by SEQ ID NO: 26 represents positions 298-333. The HER-2 B epitope identified by SEQ ID NO: 26 may be cyclized by the formation of disulfide bonds between Cys-299 and Cys-311 and/or Cys-315 and Cys-331. The HER-2 B epitope identified by SEQ ID NO: 27 represents positions 266-296. The HER-2 B epitope identified by SEQ ID NO: 27 may be cyclized by the formation of a disulfide bond between Cys-268 and Cys-295.

The HER-2 B epitope identified by SEQ ID NO: 28 represents positions 626-649. This sequence may have disulfide bonds between Cys-626 and Cys-634 and/or Cys-630 and Cys-634. It will be understood that each of epitopes having more than one Cys may be cyclized or linear.

In other embodiments, the pharmaceutical composition comprises chimeric HER-1, HER-3 and/or IGF-1R B cell peptides and one or more VEGF epitopes or VEGF chimeric or multivalent peptides. The VEGF peptides or chimerics can be any previously described in U.S. Pat. No. 8,080,253 and U.S. Patent Application Publication Nos. 2013/0216564 and 2013/0230546. Each of these references is hereby incorporated by reference in its entirety. VEGF peptides are also provided in Table 6. In some embodiments, the VEGF peptide is in retro-inverso form. In some embodiments, the two cysteine residues of the retro-inverso VEGF peptide may be linked by a disulfide bond to form a cyclized retro-inverso VEGF peptide. It should be noted that the amino acid numbering indicated in Table 6 is based upon the inclusion of the VEGF leader sequence.

TABLE 6

| Peptide Designation | Sequence | SEQ ID NO: |
|---|---|---|
| VEGF (4-21) | LLSWVHWSLALLLYLHHA | 41 |
| VEGF (24-38) | SQAAPMAEGGGQNHH | 42 |
| VEGF (76-96) | SCVPLMRCGGCSNDEGLECVP | 43 |
| VEGF (102-122) | ITMQIMRIKPHQGQHIGEMSF | 44 |
| VEGF (102-122) D-amino acid modified | ITMQCGIHQGQHPKIMICEMSF | 45 |
| VEGF (122-102) L-amino acid modified | FSMECIMRIKPHQGQHIGCQMTI | 46 |
| VEGF (126-143) | NKCECRPKKDRARQENPC | 47 |
| VEGF (127-144) | KCECRPKKDRARQENPCG | 48 |
| VEGF (162-175) | KCSCKNTHSRCKAR | 49 |
| EG-VEGF (5-15) | TRVSIMLLLVT | 50 |
| EG-VEGF (24-34) | GACERDVQCGA | 51 |
| EG-VEGF (50-67) | CTPLGREGEECHPGSHKV | 52 |
| EG-VEGF (50-75) | CTPLGREGEECHPGSHKVPFFRKRKH | 53 |
| EG-VEGF (86-102) | CSRFPDGRYRCSMDLKN | 54 |

A pharmaceutical composition comprising any combination of the HER-1 epitopes or peptide chimerics, HER-3 epitopes or peptide chimerics, IGF-1R epitopes or peptide chimerics, HER-2 epitopes or peptide chimerics, and VEGF epitopes or peptide chimerics is also considered. In particular, included herein is a pharmaceutical composition comprising: two or more different HER-1 epitopes or chimeric peptides; two or more different HER-3 epitopes or chimeric peptides; two or more different IGF-1R epitopes or chimeric peptides; one or more HER-1 epitopes or chimeric peptides and one or more HER-2 epitopes or chimeric peptides; one or more HER-3 epitopes or chimeric peptides and one or more HER-2 epitopes or chimeric peptides; one or more IGF-1R epitopes or chimeric peptides and one or more HER-2 epitopes or chimeric peptides; one or more HER-1 epitopes or chimeric peptides and one or more VEGF epitopes or chimeric peptides; one or more HER-3 epitopes or chimeric peptides and one or more VEGF epitopes or chimeric peptides; one or more IGF-1R epitopes or chimeric peptides and one or more VEGF epitopes or chimeric peptides; one or more HER-1 epitopes or chimeric peptides and one or more HER-3 epitopes or chimeric peptides; one or more HER-1 epitopes or chimeric peptides and one or more IGF-1R epitopes or chimeric peptides; or one or more HER-3 epitopes or chimeric peptides and one or more IGF-1R epitopes or chimeric peptides.

In addition to the epitopes, multivalent peptides, and chimeric peptides (which may function as antigens) or the polynucleotide which encodes the same, other components, such as a vehicle for antigen delivery and immunostimulatory substances designed to enhance the peptide's immunogenicity, are, preferably, included in the pharmaceutical composition. Examples of pharmaceutically acceptable vehicles for antigen delivery include aluminum salts, water-in-oil emulsions, biodegradable oil vehicles, oil-in-water emulsions, biodegradable microcapsules, and liposomes. For the vaccines which comprise the chimeric peptide, the preferred vehicle for antigen delivery is a biodegradable microsphere, which preferably is comprised of poly (D, L-lactide-co-glycolide) (PLGA).

While any suitable carrier known to those of ordinary skill in the art may be employed in the pharmaceutical compositions of this invention, the type of carrier will vary depending on the mode of administration and whether a substantial release is desired. For parenteral administration, such as subcutaneous injection, the carrier preferably comprises water, saline, alcohol, a fat, a wax, or a buffer. Biodegradable microspheres (e.g., polylactic galactide) may also be employed as carriers for the pharmaceutical compositions of this invention. Optionally, the pharmaceutical composition comprises an adjuvant.

The chimeric HER-1, HER-3 and IGF-1R B cell peptides are useful immunogens for inducing production of antibodies that interact with and bind to the extracellular domain of the HER-1, HER-3 and IGF-1R protein, respectively. The chimeric HER-1, HER-3 and IGF-1R B cell peptides are also useful as laboratory tools for detecting antibodies to HER-1, HER-3 and IGF-1R protein, respectively, in patient's sera. In accordance with the present invention it has been determined that the chimeric HER-1, HER-3 and IGF-1R B cell peptides invoked an antibody response in rabbits and that such antibodies (a) immunoprecipitate HER-1, HER-3 and IGF-1R protein, respectively, (b) bind to intact HER-1, HER-3 and IGF-1R receptor on HER-1, HER-3 and IGF-1R overexpressing cells, respectively, in culture, and (c) reduce proliferation of HER-1, HER-3 and IGF-1R overexpressing cells, respectively, in vitro and in a xenograft mouse model. It has also been determined that immunization of transgenic mice with one or more of the chimeric peptides MVF-HER-1 (382-410), MVF-HER-1 (418-435), MVF HER-3 (461-479), MVF IGF-1R (56-81) and MVF IGF-1R (234-252) resulted in a significant delay of tumor growth.
Preparation of HER-1, HER-3 and IGF-1R Epitopes, Mimics and Chimeric Peptides The HER-1, HER-3 and IGF-1R epitopes, mimics, and chimeric peptides, preferably, are synthesized using commercially available peptide synthesizers. Preferably, the chemical methods described in Kaumaya et al., "De Novo" Engineering of Peptide Immunogenic and Antigenic Determinants as Potential Vaccines, in Peptides, Design, Synthesis and Biological Activity (1994), pp 133-164, which is specifically incorporated herein by reference, are used.

The HER-1, HER-3 and IGF-1R epitopes, mimics and chimeric peptides may also be produced using cell-free translation systems and RNA molecules derived from DNA constructs that encode the epitope or peptide. Alternatively, the epitopes, mimics, or chimeric peptides are made by transfecting host cells with expression vectors that comprise a DNA sequence that encodes the respective epitope or chimeric peptide and then inducing expression of the polypeptide in the host cells. For recombinant production, recombinant constructs comprising one or more of the sequences which encode the epitope, mimic, chimeric peptide, or a variant thereof are introduced into host cells by conventional methods such as calcium phosphate transfection, DEAE-dextran mediated transfection, transvection, microinjection, cationic lipid-mediated transfection, electroporation, transduction, scrape lading, bollistic introduction or infection.

The HER-1, HER-3 and IGF-1R epitopes, mimics, and chimeric peptides may be expressed in suitable host cells, such as for example, mammalian cells, yeast, bacteria, insect cells or other cells under the control of appropriate promoters using conventional techniques. Suitable hosts include, but are not limited to, *E. coli, P. pastoris*, Cos cells and 293 HEK cells. Following transformation of the suitable host strain and growth of the host strain to an appropriate cell density, the cells are harvested by centrifugation, disrupted by physical or chemical means, and the resulting crude extract retained for further purification of the epitope, mimic or chimeric peptide.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, and high performance liquid chromatography (HPLC), and affinity chromatography may be used to isolate the recombinant polypeptide. To produce glycosylated epitopes, mimics, and chimeric peptides, it is preferred that recombinant techniques be used. To produce glycosylated epitopes, mimics, and chimeric peptides which contain the same, it is preferred that mammalian cells such as, Cos-7 and Hep-G2 cells be employed in the recombinant techniques. Naturally occurring variants of the HER-1, HER-3 and IGF-1R epitopes shown in Tables 1, 2 and 3 above may also be isolated by, for example, screening an appropriate cDNA or genomic library with a DNA sequence encoding the polypeptide.

Multivalent HER-1, HER-3 and IGF-1R peptides can be prepared using a combinatorial Fmoc/t-butyl, Fmoc/benzyl and Boc benzyl strategy as well as a fourth level of differential protecting group (Npys) strategy. Details of such approach are presented in Larimore et al. (1995) Journal of Virology 69:6077-6089, which is specifically incorporated herein by reference.

Identifying Functional Equivalents of the HER-1, HER-3 or IGF-1R B Cell Epitopes Shown in Table 1, 2 and 3

Functional equivalents of the HER-2 HER-1, HER-3 or IGF-1R B cell epitopes shown in Tables 1, 2 or 3 may generally be identified by modifying the sequence of the epitope and then assaying the resulting polypeptide for the ability to stimulate an immune response, e.g., production of antibodies. For example, such assays may generally be performed by preparing a chimeric peptide which comprises the modified polypeptide and a promiscuous Th cell epitope, injecting the chimeric peptide into a test animal and assaying for antibodies. Such antibodies may be found in a variety of body fluids including sera and ascites. Briefly, a body fluid sample is isolated from a warm-blooded animal, such as a human, for whom it is desired to determine whether antibodies specific for HER-1, HER-3 or IGF-1R peptide are present. The body fluid is incubated with HER-1, HER-3 or IGF-1R peptide under conditions and for a time sufficient to permit immunocomplexes to form between the peptide and antibodies specific for the protein and then assayed, preferably using an ELISA technique. In such technique, the colorimetric change is measured at 490 nm. Epitopes which induce production of antibodies that exhibit a titer equal to 10,000 or greater for HER-1, HER-3 or IGF-1R protein, are preferred. As used herein a titer of 10,000 refers to an absorbance value of 0.2 above background.

Polynucleotides

The present invention also provides isolated polynucleotides which encode the HER-1, HER-3 or IGF-1R B cell epitopes, and the chimeric peptides of the present invention. The present polynucleotides also encompass polynucleotides having sequences that are capable of hybridizing to the nucleotide sequences of under stringent conditions, preferably highly stringent conditions. Hybridization conditions are based on the melting temperature of the nucleic acid binding complex or probe, as described in Berger and Kimmel (1987) Guide to Molecular Cloning Techniques, Methods in Enzymology, vol. 152, Academic Press. The term "stringent conditions," as used herein, is the "stringency" which occurs within a range from about $T_{m-5}$ (5° below the melting temperature of the probe) to about 20° C. below $T_m$. As used herein "highly stringent" conditions employ at least 0.2×SSC buffer and at least 65° C. As recognized in the art, stringency conditions can be attained by varying a number of factors such as the length and nature, i.e., DNA or RNA, of the probe; the length and nature of the target sequence, the concentration of the salts and other components, such as formamide, dextran sulfate, and polyethylene glycol, of the hybridization solution. All of these factors may be varied to generate conditions of stringency which are equivalent to the conditions listed above.

Polynucleotides comprising sequences encoding a HER-1, HER-3 and/or an IGF-1R B cell epitope or a HER-1, HER-3 and/or an IGF-1R chimeric peptide of the present invention can be synthesized in whole or in part using chemical methods or, preferably, recombinant methods which are known in the art. Polynucleotides which encode a HER-1, HER-3 and/or an IGF-1R B cell epitope can be obtained by screening a genomic library or cDNA library with antibodies immunospecific for the HER-1, HER-3 or IGF-1R protein, respectively, to identify clones containing such polynucleotide.

The polynucleotides are useful for producing a HER-1, HER-3 and/or an IGF-1R cell epitope or a HER-1, HER-3 and/or an IGF-1R chimeric peptide. For example, an RNA molecule encoding a multivalent chimeric peptide is used in a cell-free translation systems to prepare such polypeptide. Alternatively, a DNA molecule encoding a HER-1, HER-3 and/or an IGF-1R B cell epitope or a HER-1, HER-3 and/or an IGF-1R chimeric peptide is introduced into an expression vector and used to transform cells. Suitable expression vectors include for example chromosomal, non-chromosomal and synthetic DNA sequences, e.g., derivatives of SV40, bacterial plasmids, phage DNAs; yeast plasmids, vectors derived from combinations of plasmids and phage DNAs, viral DNA such as vaccinia, adenovirus, fowl pox virus, pseudorabies, baculovirus, and retrovirus. The DNA sequence is introduced into the expression vector by conventional procedures.

Accordingly, the present invention also relates to recombinant constructs comprising one or more of the present HER-1, HER-3 and IGF-1R polynucleotide sequences. Suitable constructs include, for example, vectors, such as a plasmid, phagemid, or viral vector, into which a sequence that encodes the HER-1, HER-3 and/or an IGF-1R B cell epitope or the HER-1, HER-3 and/or IGF-1R chimeric peptide has been inserted. In the expression vector, the DNA sequence which encodes the epitope or chimeric peptide is operatively linked to an expression control sequence, i.e., a promoter, which directs mRNA synthesis. Representative examples of such promoters, include the LTR or SV40 promoter, the *E. coli* lac or trp, the phage lambda PL promoter and other promoters known to control expression of genes in prokaryotic or eukaryotic cells or in viruses. The expression vector, preferably, also contains a ribosome binding site for translation initiation and a transcription terminator. Preferably, the recombinant expression vectors also include an origin of replication and a selectable marker, such as for example, the ampicillin resistance gene of *E. coli* to permit selection of transformed cells, i.e., cells that are expressing the heterologous DNA sequences. The polynucleotide sequence encoding the HER-1, HER-3 and/or an IGF-1R B cell epitope or the HER-1, HER-3 and/or IGF-1R chimeric peptide is incorporated into the vector in frame with translation initiation and termination sequences. Preferably, the polynucleotide further encodes a signal sequence which is operatively linked to the amino terminus of the HER-1, HER-3 and/or an IGF-1R B cell epitope or HER-1, HER-3 and/or IGF-1R chimeric peptide.

The polynucleotides encoding the HER-1, HER-3 and/or IGF-1R B cell epitope or the HER-1, HER-3 and/or IGF-1R chimeric peptide comprising such epitopes are used to express a recombinant peptide using techniques well known in the art. Such techniques are described in Sambrook, J. et al (1989) Molecular Cloning A Laboratory Manual, Cold Spring Harbor Press, Plainview, N.Y. and Ausubel, F. M. et al. (1989) Current Protocols in Molecular Biology, John Wile & Sons, New York, N.Y. Polynucleotides encoding the HER-1, HER-3 and/or an IGF-1R B cell epitope or the HER-1, HER-3 and/or IGF-1R chimeric peptide comprising such epitopes are also used to immunize animals.

The HER-1, HER-3 and/or an IGF-1R chimeric and multivalent peptides and the polynucleotides which encode the same are useful for enhancing or eliciting, in a subject or a cell line, a humoral response. As used herein, the term "subject" refers to any warm-blooded animal, preferably a human. A subject may be afflicted with cancer, such as breast cancer, or may be normal (i.e., free of detectable disease and infection). The pharmaceutical composition is particularly useful for treating women who have a family history of breast cancer or who have had breast tumors removed.

Antibodies

Also provided herein are isolated antibodies and antibody fragments that specifically bind to the HER-1, HER-3 or IGF-1R epitopes or peptide chimerics. In some embodiments, the antibody may be monoclonal, humanized, or both. As used herein, the term "antibody" is used in the broadest sense, and specifically covers monoclonal antibodies (including full length monoclonal antibodies), polyclonal antibodies, and multispecific antibodies (e.g., bispecific antibodies). Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end.

The term "antibody fragment" refers to a portion of a full-length antibody, generally the target binding or variable region. Examples of antibody fragments include Fab, Fab', F(ab')$_2$ and Fv fragments. The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such molecule from having the ability to bind to the high affinity receptor, FcεRI. As used herein, "functional fragment" with respect to antibodies, refers to Fv, F(ab) and F(ab')$_2$ fragments. An "Fv" fragment is the minimum antibody fragment which contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Collectively, the six CDRs confer target binding specificity to the antibody. However, even a single variable domain (or half of an Fv comprising only three CDRs specific for a target) has the ability to recognize and bind target, although at a lower affinity than the entire binding site. "Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for target binding.

II. Methods of Treatment

The present invention also provides methods of stimulating an immune response and/or treating a cancer which is associated with over-expression or over-activation of the HER-2, HER-1, HER-3, IGF-1R and/or VEGF. Such cancers include breast, lung, ovarian, bladder, esophageal, gastric, and prostate. The method comprises administering a pharmaceutical composition comprising one or more of the chimeric peptides or multivalent peptides of the present invention to a subject in need of such treatment. Preferably multiple intramuscular injections, at three week intervals are used to administer the pharmaceutical composition.

Preferred peptide mimics, chimeric peptides or multivalent peptides for administration are those which comprise one or more of the following epitopes: HER-1 (347-374), HER-1 (382-410), HER-1 (418-435), HER-3 (237-269), HER-3 (461-479), HER-3 (99-122), HER-3 (140-162), IGF-1R (6-26), IGF-1R (26-42), IGF-1R (56-81), and IGF-1R (234-252). In some embodiments, a pharmaceutical composition is administered to a subject that comprises one or more of the following epitopes: HER-1 (347-374), HER-1 (382-410), HER-1 (418-435), HER-3 (237-269), HER-3 (461-479), HER-3 (99-122), HER-3 (140-162), IGF-1R (6-26), IGF-1R (26-42), IGF-1R (56-81), and IGF-1R (234-252) or a functional equivalent thereof; and one or more HER-2 epitopes selected from the group provided in Table 5 herein and those previously described in U.S. Pat. Nos. 7,060,284; 7,666,430; 7,691,396; 8,110,657; and 8,470,333 and U.S. Patent Application Publication Nos. 2010/0234283, 2012/0201841, and 2014/0010831. In still other or further embodiments, a pharmaceutical composition is administered to a subject that comprises one or more of the following epitopes: HER-1 (347-374), HER-1 (382-410), HER-1 (418-435), HER-3 (237-269), HER-3 (461-479), HER-3 (99-122), HER-3 (140-162), IGF-1R (6-26), IGF-1R (26-42), IGF-1R (56-81), and IGF-1R (234-252) or a functional equivalent thereof; and one or more VEGF peptides or chimerics selected from the group provided in Table 6 herein and those previously described in U.S. Pat. No. 8,080,253, and U.S. Patent Application Publication Nos. 2013/0216564 and 2013/0230546.

In other embodiments, multiple pharmaceutical compositions are administered to a subject in need of a cancer treatment, wherein the multiple pharmaceutical compositions are different in their composition and comprise one or more HER-1 epitopes, one or more HER-3 epitopes, one or more IGF-1R epitopes, one or more HER-2 epitopes, and/or one or more VEGF epitopes, wherein the one or more HER-1, HER-3 and IGF-1R epitopes are selected from HER-1 (347-374), HER-1 (382-410), HER-1 (418-435), HER-3 (237-269), HER-3 (461-479), HER-3 (99-122), HER-3 (140-162), IGF-1R (6-26), IGF-1R (26-42), IGF-1R (56-81), and IGF-1R (234-252), or a functional equivalent thereof; the one or more HER-2 epitopes are selected from the group provided in Table 5 herein and those previously described in U.S. Pat. Nos. 7,060,284; 7,666,430; 7,691,396; 8,110,657; and 8,470,333 and U.S. Patent Application Publication Nos. 2010/0234283, 2012/0201841, and 2014/0010831; and the one or more VEGF epitopes are selected from the group provided in Table 6 herein and those previously described in U.S. Pat. No. 8,080,253, and U.S. Patent Application Publication Nos. 2013/0216564 and 2013/0230546. The Examples below demonstrate that methods of treating a cancer with more than one HER-1, HER-3, HER-2, IGF-1R, and/or VEGF epitope or chimeric peptide provide surprising and synergistic results.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes.

EXAMPLES

Example 1

Materials and Methods Related to HER-1 Peptide Vaccines and Chimeric Peptides

Peptide Synthesis and Characterization:
Peptide synthesis was performed using 9600 Milligen/Biosearch solidphase peptide synthesizer (Millipore, Bedford, Mass.) using Fmoc/t-But chemistry. Clear amide resin (0.32 mmol/gm) (Peptide International, Louisville, Ky.) was used for synthesis of all of the peptides. In the case of the peptide vaccines, the B cell epitopes were colinearly synthesized with the promiscuous Th MVF epitope using regioselective side chain protections. After synthesis, the peptides were cleaved from the resin as previously described [Garrett, J. T., et al. 2007. J. Immunol. 178: 7120-7131]. The crude peptides were purified by reverse phase HPLC in a gradient system using a C-4 vydac column in water/acetonitrile (0.1% trifluoroacetic acid) on a Waters system. At the end of purification, the pure fractions were then analyzed in analytical HPLC, and fractions of interest were pooled together and lyophilized in 1% acetic acid solution. The final purified peptides were then identified using electrospray ionization mass spectrometry (Campus Chemical Instrumentation Center, The Ohio State University, Columbus, Ohio).

Animals:
FVB/n wild-type inbred mice and BALB/c SCID mice were purchased from Charles River Laboratories, whereas female New Zealand White outbred rabbits were purchased from Harlan Breeders. Animal care and use was in accordance with the International Animal Care and Use Committee institutional guidelines.

Cell Lines and Abs:
All cell-culture medium, FBS, and supplements were purchased from Invitrogen Life Technologies. The human TNBC cell line MDA-MB-468 and lung cancer cell line A549 were purchased from American Type Culture Collection and maintained according to the supplier's guidelines. Met-1 cells are a mouse mammary cell line established in vitro from PyMT-transgenic mice with an FVB/n background, in which tumor growth and development are dependent on high expression of the HER family members [Borowsky, A. D. et al. 2005. Clin. Exp. Metastasis 22: 47-59; Pei, X. F., et al. 2004. In Vitro Cell. Dev. Biol. Anim. 40: 14-21]. Cetuximab was purchased from The James Cancer Hospital pharmacy of The Ohio State University Wexner Medical Center.

Immunoassays:
To determine the Ab response to the peptide vaccine in both mice and rabbits, experimental procedures were performed as previously described [Dakappagari, N. K., et al., 2000. Cancer Res. 60: 3782-3789]. ELISA was performed to evaluate the binding of the vaccine Abs to rhEGFR (R&D Systems). The 96-well plates were coated with 100 ml 2 mg/ml peptide Ag in PBS and refrigerated overnight. The plates were then washed with PBT/human serum, and non-specific binding was blocked by adding 200 ml PBS/1% BSA with 0.02% sodium azide. After washing, 200 ml serum dilution starting at 1/500 for mice and 1/4000 for rabbits was added to the peptide-coated plates in duplicate wells, serially diluted 1:2 in phosphate buffer with Tween 20/human serum wash buffer, and incubated for 2 hours at room temperature. The plates were washed, and 100 ml HRP-conjugated secondary Ab at a dilution of 1/500 was added and incubated for 1 hour. After incubation, the plates were washed, and 50 ml substrate solution was added to each well for bound Ab detection and incubated for 10 minutes in the dark before stopping the reaction with 25 ml 1% SDS and reading the absorbance at 415 nm using a Bio-Rad microplate reader (Bio-Rad). Titers were considered as the highest dilution of sera with an absorbance of 0.2 after subtracting the blank.

Rabbit Immunization and Ab Purification:
Female New Zealand White rabbits were used for immunization. Groups of rabbits (two per each vaccine epitope) were immunized as previously described [Garrett, J. T., et al. 2007. J. Immunol. 178: 7120-7131]. For each rabbit, 1 mg peptide vaccine was dissolved in water with 100 mg nor-MDP, and the total volume was mixed with an equal volume of ISA 720 by plunging back and forth at least 50 times. The mixture was injected into the bicep muscle of the rabbit. The rabbits were immunized three times at 3-week intervals, and 4 weeks after the third immunization (3Y+4W), large volumes of blood were collected and used for Ab purification. The purification was done using IgG agarose beads that bind to the IgG Abs present in the rabbit sera.

Flow Cytometry:
The experiment was performed as previously described [Vicari, D., K. et al. 2011. J. Biol. Chem. 286: 13612-13625] using $5 \times 10^5$ MDA-MB-468 breast cancer cells or A549 lung cancer cells. Cells were trypsinized, resuspended in approximately 10 ml appropriate growth media, and then counted by trypan blue staining. The cells were then resuspended such that a single solution of 100 ml will contain $1 \times 10^6$ cells in 5-ml polystyrene culture tubes. The primary Ab was then added to each tube, gently vortexed, and then incubated for 2 hours at 4° C. The tubes were then washed twice in 1 ml ice-cold PBS, spun at 1700 rpm for 5 minutes, and then decanted. The secondary Ab (anti-rabbit IgG-FITC conjugate) made up at 1:50 in a final volume of 100 ml was then added to each tube and incubated in the dark for 30 minutes after vortexing. The tubes were then washed twice in 1 ml ice cold PBS and spun at 1700 rpm for 5 minutes after each wash before resuspending in 500 ml 1% formaldehyde made in PBS. Samples were then analyzed by a Coulter ELITE flow cytometer (Beckman Coulter), and 10,000 events were counted per treatment. Single-parameter histograms were drawn after gating selection of healthy cells through light scattered assessment.

MTT Proliferation Assay:

The proliferation assay was performed as previously described (Foy, K. C., et al. 2011. J. Biol. Chem. 286: 13626-13637]. Briefly, MDA-MB-468 ($1 \times 10^4$ cells/well) and A549 cells ($5 \times 10^3$ cells/well) were incubated overnight before changing media to low FBS and then incubated for another day. The following day, the inhibitors were added at different concentrations in low FBS media and incubated for 1 hour before stimulating with 50 ng/ml EGF and then incubated for 3 days. The MTT reagent was then added and incubated for 2 hours followed by addition of extraction buffer and then incubating overnight. The following day, the plate was read at 570 nm using a spectrophotometer.

EGFR-Specific Phosphorylation:

A549 and MDA-MB-468 cells ($1 \times 10^6$) were seeded on six-well plates in growth media supplemented with 10% FBS and incubated overnight at 37° C. Culture media was then removed, and the cells were washed with 1 ml PBS before adding low serum media (1% FBS) and incubating for another day. Culture media was then removed and the cell layer washed with PBS before adding different 100 mg inhibitors in binding buffer (0.2% w/v BSA and RPMI 1640 medium with 10 mM HEPES [pH 7.2]) to the wells and incubating at room temperature for 1 hour. The cells were then stimulated by adding 50 ng/ml EGF per well and then incubated for another 10 minutes at room temperature. Binding buffer was removed and the cell layer washed with PBS before adding 1 ml RIPA lysis buffer. Plates were then rocked at 4° C. for 1 hour, lysates were removed from wells and spun at 13,000 3 g for 10 minutes, and supernatants were transferred into clean tubes and stored at 280° C. until usage. Protein lysates were used to measure phosphorylated EGFR using the Duoset IC human phosphor-ErbB1 ELISA kit (R&D Systems), and inhibition of phosphorylation was calculated using the formula using the formula: (ODUNTREATED−ODTREATED)/ODUNTREATED×100.

Caspase Assay:

The caspase assay was performed exactly like the proliferation assay, except that after treatment, the cells were incubated for just 24 hours. After incubation, the Caspase Glo reagent substrate (Promega) was prepared according to the manufacturer's instructions and then added to the wells, mixed, and incubated for 2 hours before measuring luminescence using a luminometer.

ADCC:

ADCC was performed as previously described [Kaumaya, P. T., et al. 2009. J. Clin. Oncol. 27: 5270-5277], in which target cells (A549 and MDA-MB-468 cells) were placed on 96-well translucent plates, and the vaccine Abs were added to the cells and equilibrated for 25 minutes before adding effector cells (human PBMCs) at different E:T ratios. The plate was then incubated for at least 2 hours before adding the ADCC reagent mixture and luminescence was measured in a luminometer.

Antitumor effects of immunization with HER-1 peptide vaccines and chimeric peptides in Fvb/n breast cancer model The Fvb/n transplantable model of HER-family dependent breast cancer represents a good model for human breast cancer. The peptide vaccines were dissolved in water and emulsified in Montanide ISA 720 (1:1) and 100 mg nor-MDP (N-acetylglucosamine-3yl-acetyl-1-alanyl-D-isoglutamine). Female wild-type FVB/n mice (Charles River Laboratories) at the age of 5 to 6 weeks were immunized three times at 3-week intervals with 100 mg peptide vaccine, and 14 days after the third immunization, the mice were challenged s.c. with Met-1 cells (200,000 per mouse). Met-1 cells were derived from the PyMT-transgenic mouse model with FVB/n background. Tumor growth was monitored for up to 6 weeks after challenge. During immunization, blood was drawn biweekly and used in ELISA to monitor Ab titers. In the case of treatment with the chimeric peptides, the mice were simply challenged with Met-1 cells and treated weekly i.v. with 200 mg chimeric peptides for up to 6 weeks beginning at day 0. The mice were euthanized at the end of treatment and tumors extracted and weighed.

BALB/c Transplantable Lung Tumor Model:

BALB/c SCID mice 5 to 6 weeks old were s.c. injected with 33106 A549 lung cancer cells, and starting from day of tumor injection, mice were treated i.v. with 200 mg each chimeric peptide or cetuximab. In the case of the Abs, the mice were treated i.p. with 500 mg starting from day 0, and all treatments were repeated weekly right up to week 6. Tumor growth was measured twice weekly using vernier calipers, and at the end of the experiment, the tumors were extracted and weighed.

Immunohistochemical Analysis:

Tumor tissues were formalin fixed, embedded in paraffin, and stained immunohistochemically for CD31 and Ki-67. The tissue blocks were cut into 4-mm sections, deparaffinized in xylol, and then rehydrated with different grades of alcohol. The rehydrated sections were then washed with distilled water and placed in a microwave oven for 15 minutes. The slides were then blocked and incubated for 40 minutes at 20° C. with primary Abs specific for Ki-67 and CD31. After incubation, the slides were washed and incubated with secondary Abs for 30 minutes before revealing Ab binding with peroxide substrate and counterstaining with hematoxylin.

Example 2

Synthesis and Characterization of HER-1 Peptide Vaccines and Chimeric Peptides

Synthesis:

The crystal structure of the extracellular domain of EGFR bound to its ligand EGF reveals the specific key residues that are important in binding [Burgess, A. W., et al. 2003. Mol. Cell 12: 541-552]. Three peptide epitopes, HER-1 (347-374), HER-1 (382-410) and HER-1 (418-435), were selected that contain at least one region of the binding sequences that make contact with EGF ligand. One of the epitopes HER-1 (382-410) overlaps with the binding site of cetuximab, which is known to inhibit EGFR ligand binding [Li, S. et al. 2005. Cancer Cell 7: 301-311]. Chimeric peptides comprising the HER-1 B cell epitopes were created by synthesizing a HER-1 B cell epitope colinearly with a promiscuous Th epitope. The Th epitope was derived from a modified MVF (288-302) (SEQ ID NO:12) and was linked to the B cell epitope via a four-residue flexible linker for independent folding [Lairmore, M. D., et al. 1995. J. Virol. 69: 6077-6089]. The chimeric peptides are also referred to herein as "peptide vaccines." Peptide mimics were also created wherein the HER-1 B cell epitopes were acetylated and amidated (i.e., Acetyl-XXX-COHN2).

Immunogenicity of HER-1 Peptide Vaccines in Rabbit and Binding of Vaccine Abs to rhEGFR:

The immune response to each of the three HER-1 peptide vaccines was analyzed in outbred rabbits. The three constructs elicited high amounts of Abs with titers greater than 250,000 (FIG. 1A-C), and high levels were still detected 3 weeks after the third immunization. This illustrates that the vaccine constructs were highly immunogenic and able to establish immunological memory in the rabbits. The binding of the Abs to rhEGFR was tested in an ELISA assay using different dilutions, and these Abs were able to bind specifically to the protein in a concentration-dependent manner (FIG. 1D). This suggests that the peptide epitopes were able to mimic the structure of the rEGFR.

Figure 1E:
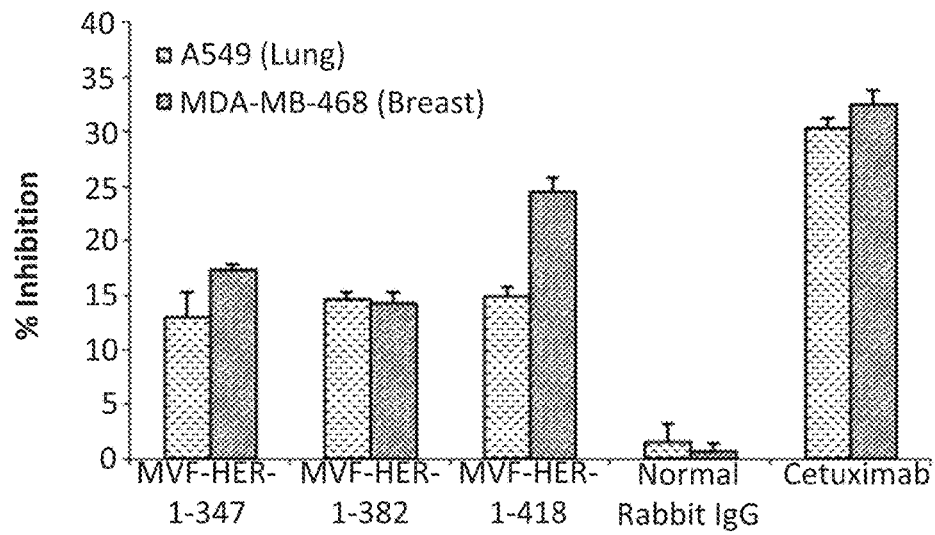
Figure 1F:
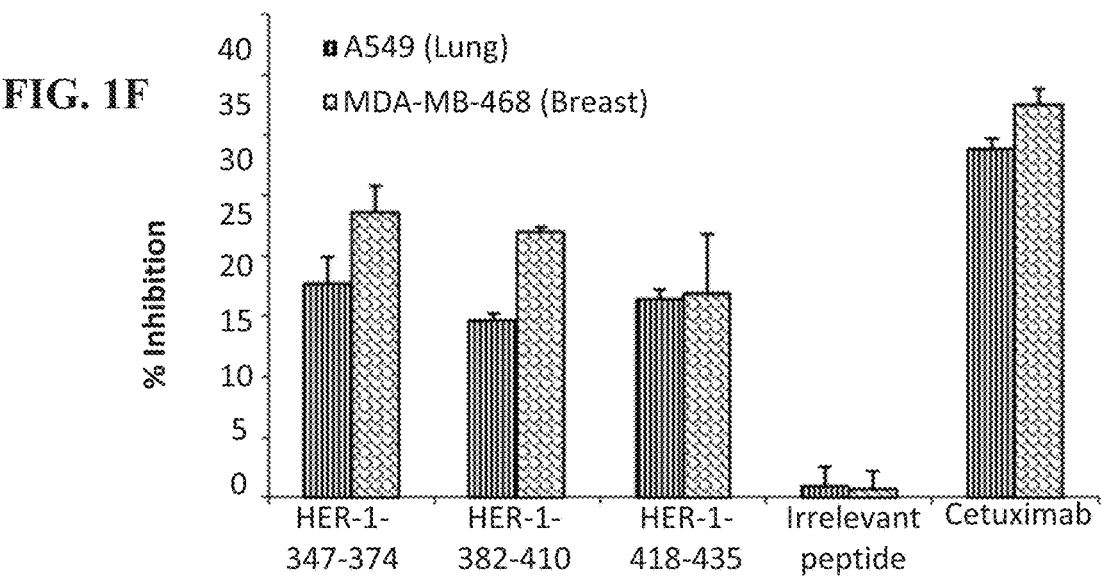

Antiproliferative effects of HER-1 peptide mimics and peptide vaccine Abs: Ligand binding to EGFR results in activation of the receptor that causes formation of dimers with itself and heterodimers with other HER family members. This triggers increase proliferation of the receptor and intracellular signaling. Therefore, the effects of inhibiting ligand binding with the chimeric peptides and peptide vaccine Abs on proliferation were tested using lung and breast cancer cell lines. To measure proliferation, the MTT assay was used, in which the cells were treated with the inhibitors and incubated for 3 days before adding MTT. FIGS. 1E and 1F show the effect of the vaccine Abs (1E) and peptide mimics (1F) on the rate of proliferation of breast and lung cancer cells. The results show an increase in the rate of inhibition after treatment, suggesting that the inhibitors are able to block ligand binding and prevent proliferation of EGFR-expressing cancer cells.

Figure 2A:
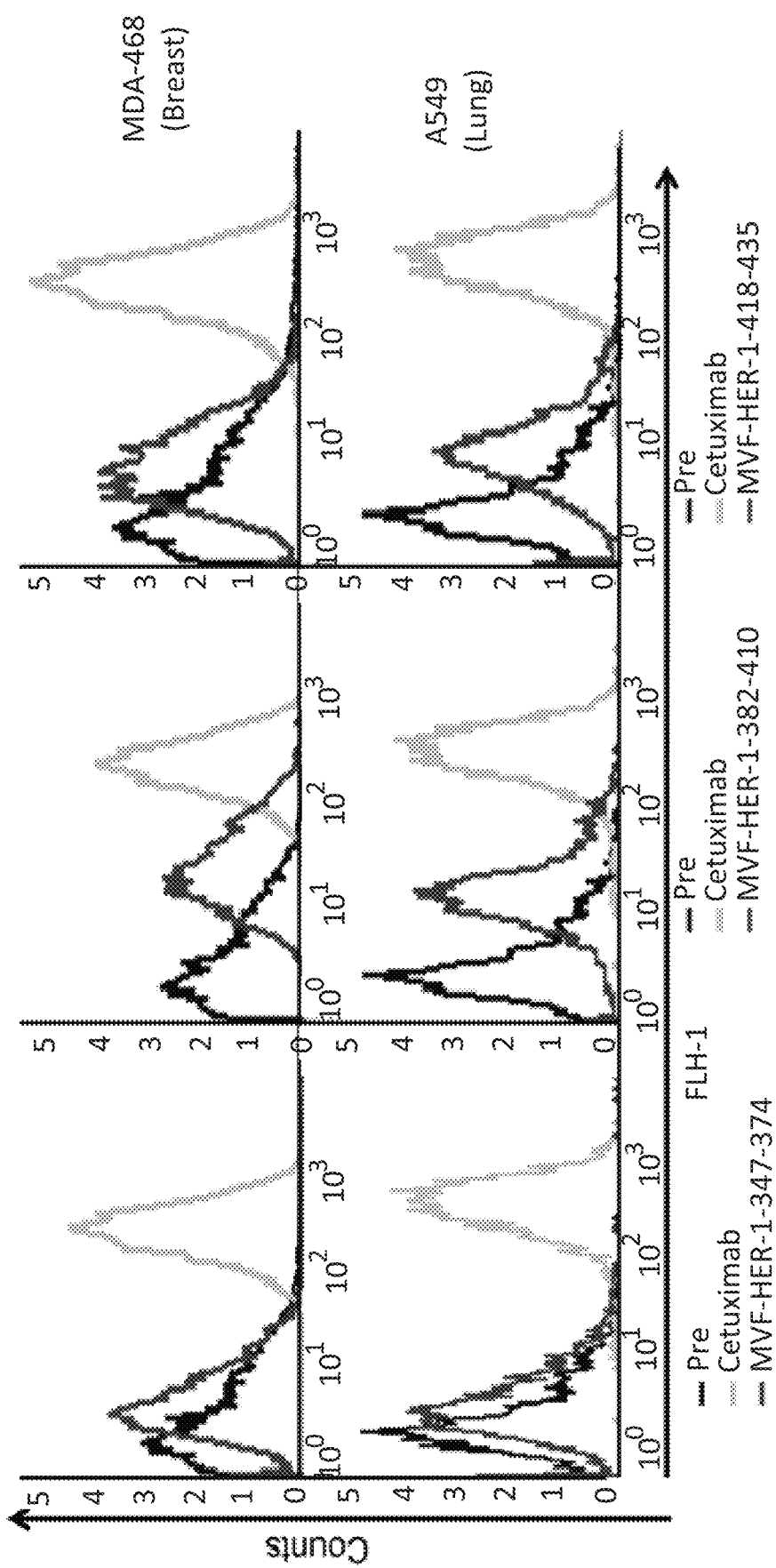
FIG. 2 (A-C) contains graphs showing that HER-1 vaccine antibodies (Abs) specifically bind EGFR-expressing cells and induce ADCC. (A) Human cancer cell lines A549 and MDA-MB-468 were incubated with peptide vaccine-induced Abs, and the extent of cell binding was evaluated by immunofluorescence flow cytometry. A shift of the histogram to the right indicates increase in binding. Pre-Abs were used as a negative control, whereas cetuximab was used as a positive control. Vaccine Abs induce ADCC of cancer cells. Target cells A549 lung cancer cells (B) and MDA-MB-468 breast cancer cells (C) were incubated with 100 mg/ml of peptide Abs and assayed in the presence of normal human PBMCs at E:T ratios of 100:1, 20:1, and 4:1 in triplicates. Lysis was measured using the aCella-TOX kit, and results represent average of three different experiments with each experiment performed in triplicates.
Figure 2B:
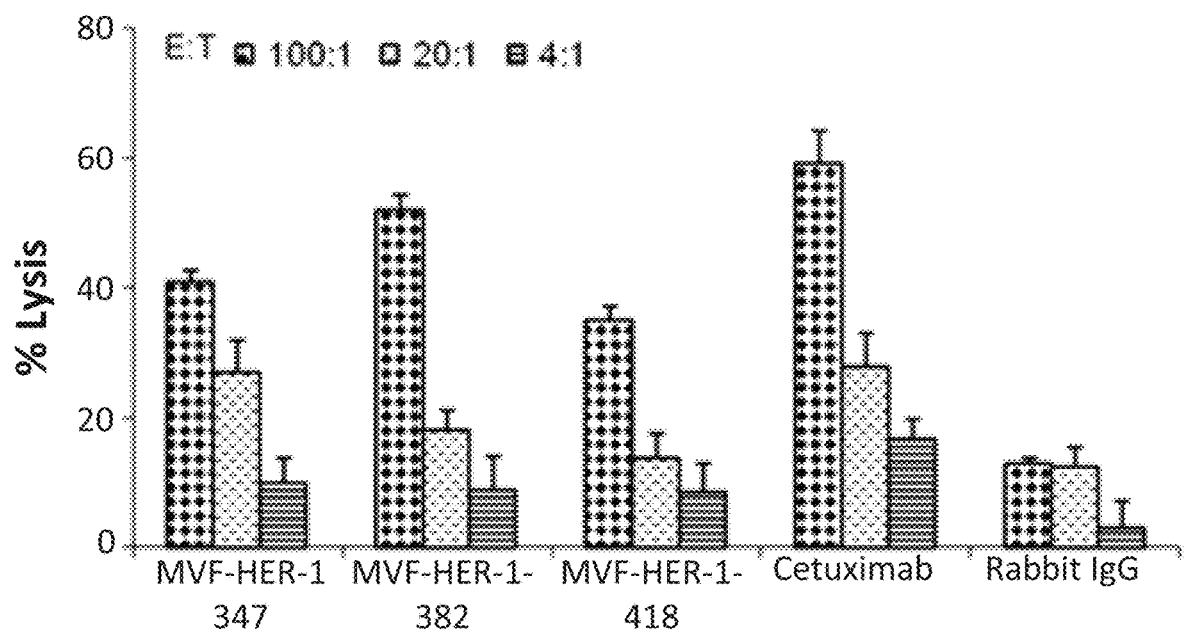
Figure 2C:
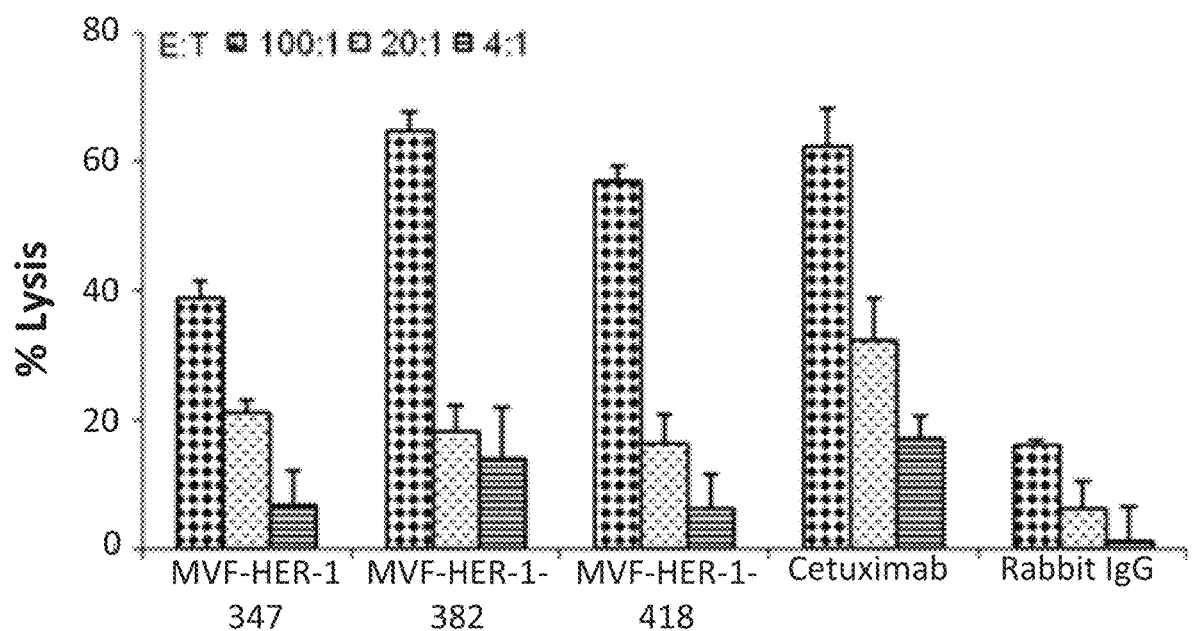

Cross-Reactivity of HER-1 Vaccine Abs to EGFR-Expressing Cells and their Ability to Cause ADCC:

In the case of assessing binding to human breast (MDA-MB-468) and lung (A549) cancer cells, immunofluorescence staining techniques were used to study the binding affinities. Polyclonal Abs generated to all three peptide constructs showed binding capabilities to both cell lines, with the HER-1 (382-410) and HER-1 (418-435) vaccine constructs having the greatest binding affinity compared with preserum (FIG. 2A) and HER-1 epitope 347-374 showing minimal binding. The vaccine polyclonal Abs did not show any binding to MCF-7 (EGFR-negative) breast cancer cells (results not shown). One of the main mechanisms of action of humanized Abs is to induce ADCC by stimulating the PBMCs and traffic them to the cancer cells, eventually causing their killing. The effects of the vaccine Abs were tested on breast and lung cancer cells as target cells and using PBMCs as effector cells. Three different effectors were used to target ratios, and the results showed that the peptide Abs were able to cause ADCC by inducing lysis of the target cells in concentration-dependent manner. The effects were greater when an E:T ratio of 100:1 was used (FIG. 2B, 2C). These results indicate that the vaccine Abs are able to specifically stimulate human PBMCs to kill cancer cells.

Figure 3A:
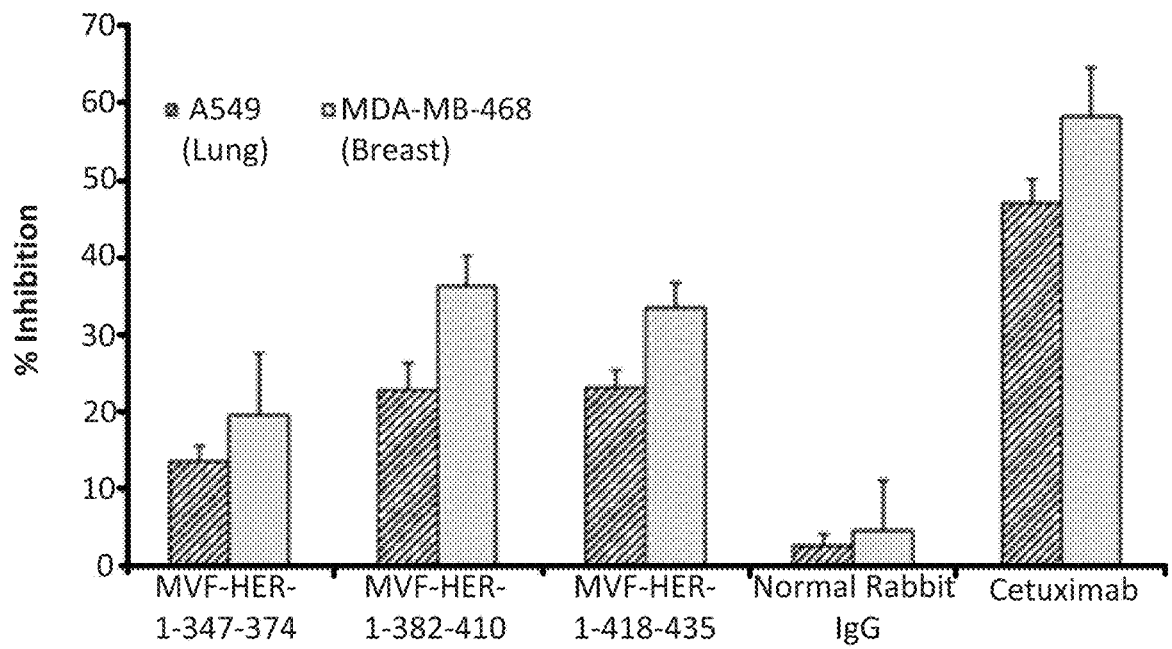
FIGS. 3 (A & B) contains graphs showing HER-1 vaccine Abs and peptide mimics decrease EGFR-specific phosphorylation. EGFR specific phosphorylation was determined using recombinant human phospho-ELISA kit after treatment with vaccine Abs (A) and peptide mimics (B), and percentage inhibition was calculated using the formula (ODUNTREATED ODTREATED)/ODUNTREATED×100. Results shown represent the average of three different experiments with each treatment performed in triplicates, and error bars represent SDs from the mean.
Figure 3B:
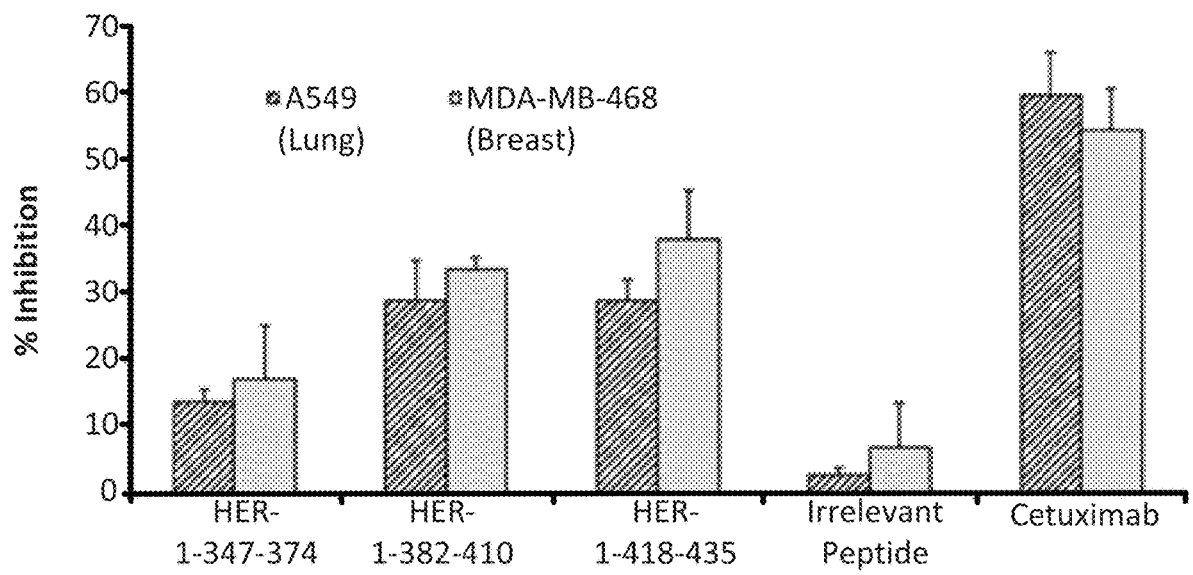

HER-1 Peptide Mimics and Peptide Vaccine Abs Inhibit EGFR Receptor Phosphorylation:

The effects of treatment with both types of inhibitors (antipeptide Abs versus chimeric peptides) on EGFR receptor phosphorylation were evaluated. EGFR activation is promoted by ligand binding, which leads to dimerization, triggering phosphorylation and increasing metastasis [Hirsch, F. R., et al. 2003. J. Clin. Oncol. 21: 3798-3807]. The levels of phosphorylated EGFR were measured using a very sensitive ELISA kit, and the results showed a similar increase in the levels of inhibition by vaccine Abs and peptide mimics in lung and breast cancer cells (FIG. 3A, 3B). FIG. 3A shows treatment with anti peptide antibodies; and FIG. 3B shows treatment with peptide mimics. These results indicate that the vaccine Abs and chimeric peptides are able to block ligand-induced phosphorylation of the EGFR receptor.

Figure 4A:
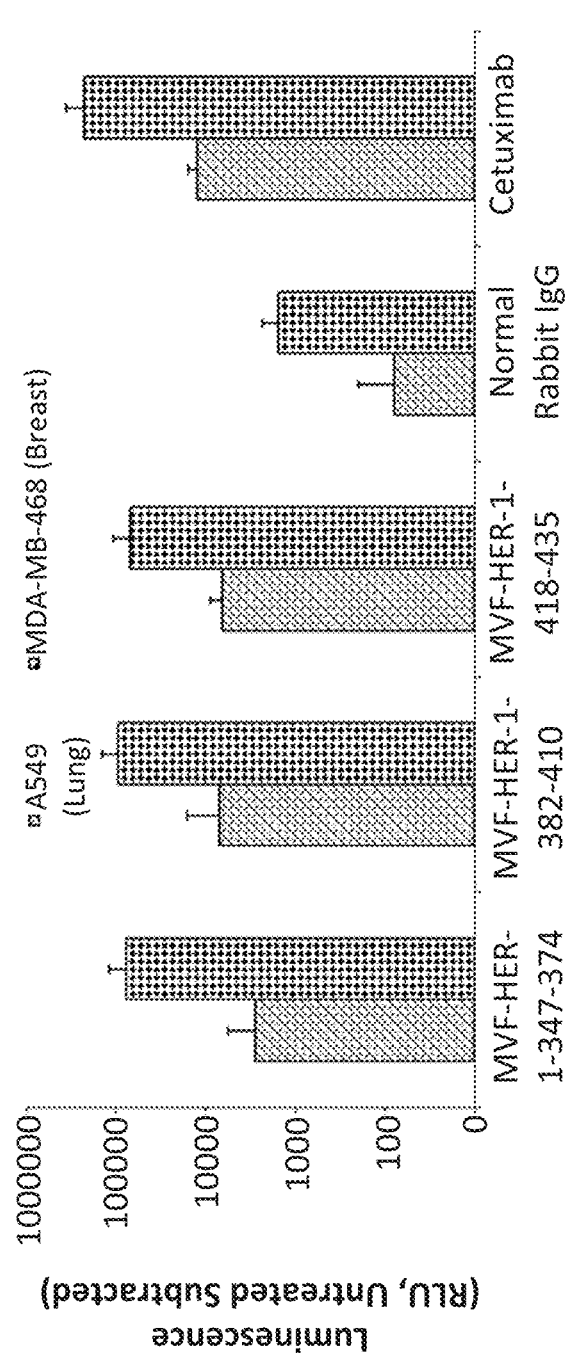
FIGS. 4 (A & B) contains graphs showing induction of apoptosis by HER-1 peptide mimics and vaccine Abs. Apoptosis was evaluated by measuring caspase activity after treatment with peptide vaccine Abs (A) and peptide mimics (B). Cells were plated in 96-well plates, treated with inhibitors for 24 hours before adding caspase reagent, and read in a luminometer. Normal rabbit IgG and irrelevant peptide were used as negative controls, whereas cetuximab was used as a positive control. Results represent average of three different experiments performed in triplicates, and error bars represent SDs from the mean.
Figure 4B:
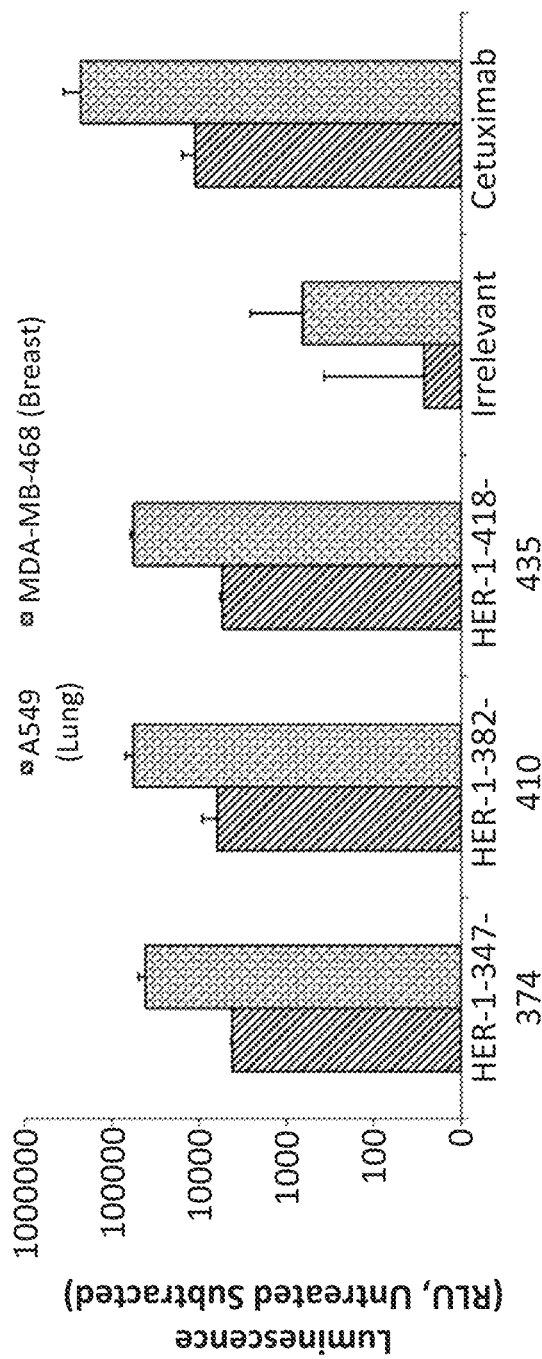

Apoptosis Determination by Measuring Caspase Activity:

Cells (A549 and MDA-MB468) in exponential growing phase were seeded in 96-well plates, and the following day, the cells were treated with peptide mimics and peptide vaccine Abs as inhibitors and incubated for a day. After treatment, apoptosis was evaluated by measuring caspase-3/7 activity using the Caspase-Glo reagent kit (Promega). Results obtained showed a significant increase in the amount of caspase activity in the treated cases when compared with the irrelevant peptide and normal rabbit IgG. Treatment caused a greater than 10-fold increased in caspase activity (FIGS. 4 A & B), which is indicative of increased apoptosis. FIG. 4A shows treatment with anti peptide or vaccine antibodies; FIG. 4 B shows treatment with peptide mimics. These results indicate that the peptide Abs as well as the peptide mimics were able to induce apoptosis in breast and lung cancer cells in vitro.

Figure 5A:
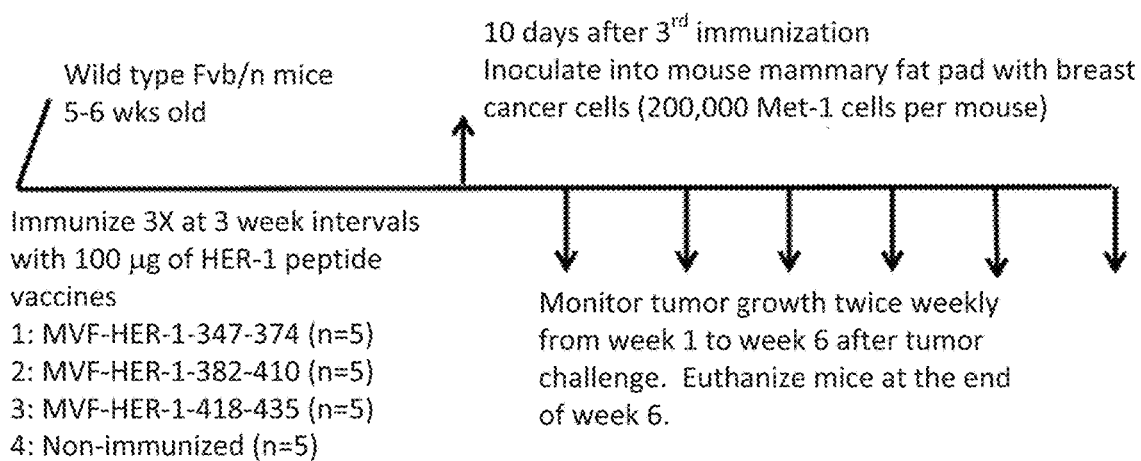
FIGS. 5 (A & B) contains a schematic and graph showing immunogenicity of HER-1 peptide vaccines in FVB/n mice. (A) The immunization scheme for FVB/n mice was mice (n=5) were immunized i.m. with 100 mg of EGFR peptide vaccines three times at 3-week intervals, and 10 days after the third immunization, mice were challenged with Met-1 cells, and tumor growth was monitored for up to 6 weeks. (B) Results show relatively high levels of Ab titers (approximately 40,000) before and after tumor injection.
Figure 5B:
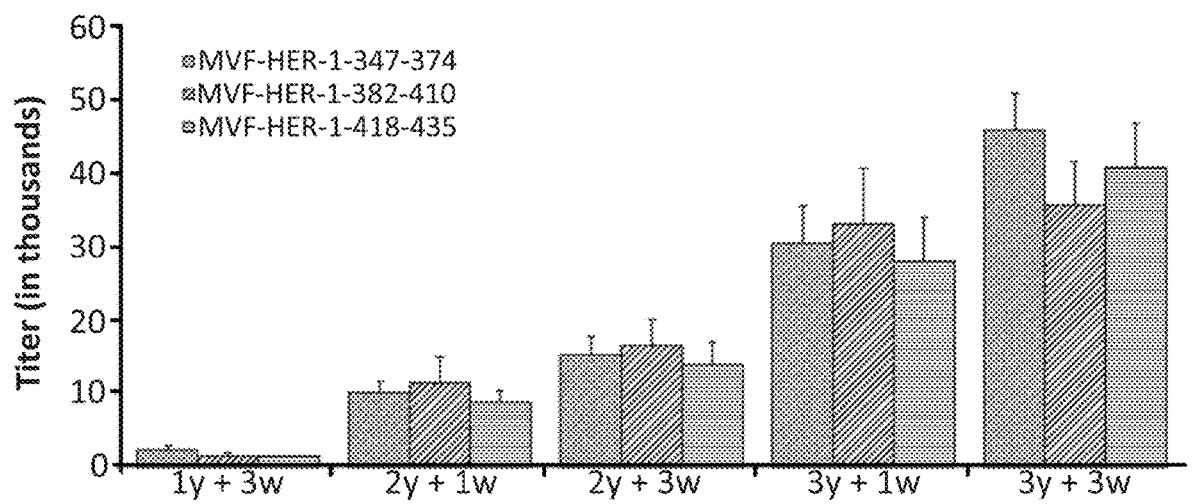
Figure 6A:
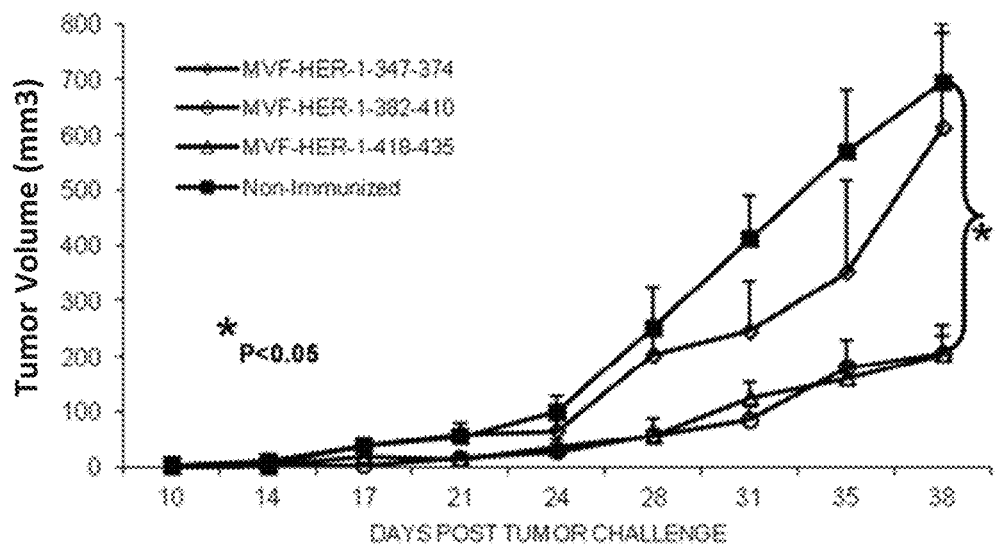
FIG. 6 (A-F) contains graphs and pictures that show the effects of HER-1 peptide vaccine immunization in the FVB/n Met-1 transplantable tumor model. (A) Peptide vaccination caused a delay in onset of tumor growth and development, with the 382-410 and 418-435 vaccine constructs significantly reducing tumor growth (*p, 0.05). (B) Peptide vaccine treatment significantly reduces percentage tumor weight per body mass (*p=0.027 for 382-410; *p=0.023 for 418-435 construct). Tumor sections were stained for dividing cells using ki-67 (C) and blood vessels using CD31 (D). Abs and slides were observed under a microscope, and representative photos in each treatment group are shown. Staining was quantified using the Image J software (National Institutes of Health), and results shown in (E) and (F) represent mean values from three different fields. Error bars represent SD from the mean.
Figure 6B:
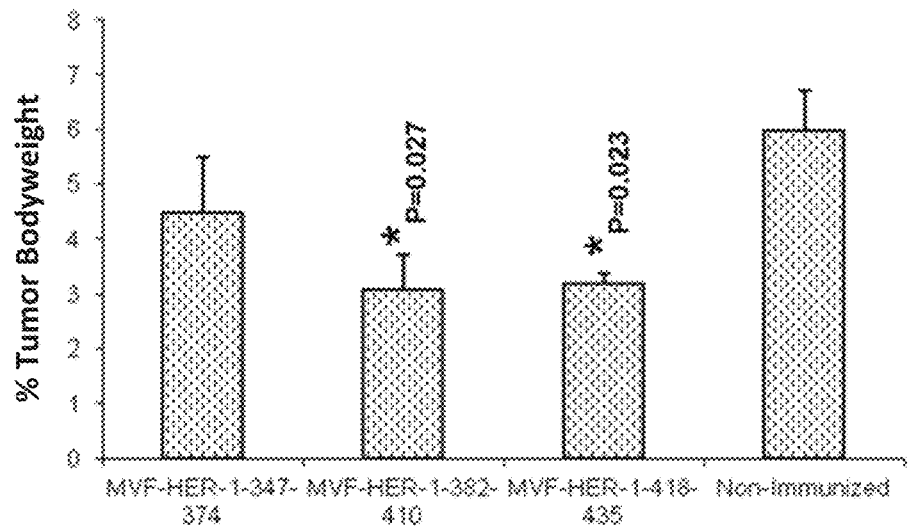

Antitumor Effects of HER-1 Peptide Vaccine Immunization in FVB/n Transplantable Mouse Model:

To evaluate the inhibitory effects of the peptide vaccines in vivo, the FVB/n transplantable mouse model was used in which Met-1 cells from FVB/n background were injected in the mammary fat pad of wild-type FVB/n mice after immunization with the chimeric MVF HER-1 peptides as shown in the immunization schedule (data not shown). Tumor development in this model is dependent on the HER family receptor overexpression. All mice were immunized at 5 to 6 weeks of age and received two boosters at 3-week intervals. As depicted in FIG. 5, the vaccine constructs were immunogenic in the mice, and all of the mice had relatively high titers of the Abs (greater than 40,000). Mice were challenged with Met-1 cells and monitored weekly for 6 weeks. Results showed that two of the vaccine constructs (382-410 and 418-435) were able to significantly (*p, 0.05; FIG. 6A) delay onset of tumor growth and development (FIG. 6A). Tumors in these two groups had a significant delay in onset of tumor development, and the tumors were smaller than the untreated groups. The percentage tumor weight in these two cases was also significantly smaller (*p, 0.028, FIG. 6B).

Figure 6C:
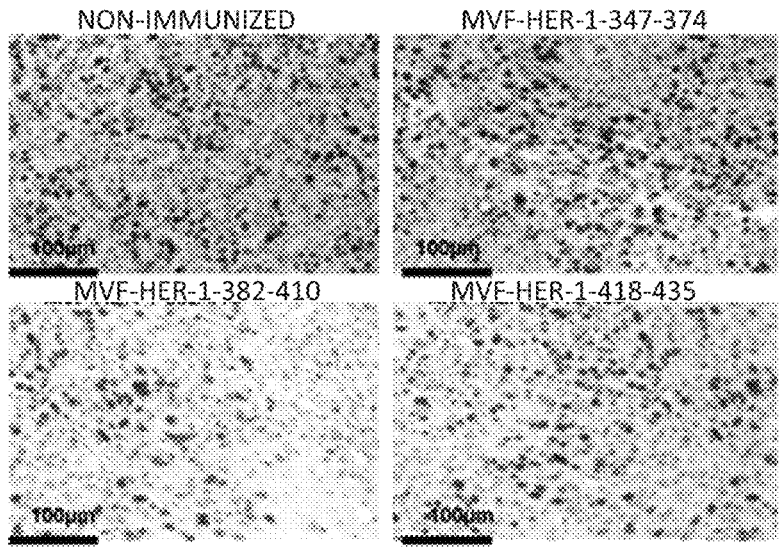
Figure 6D:
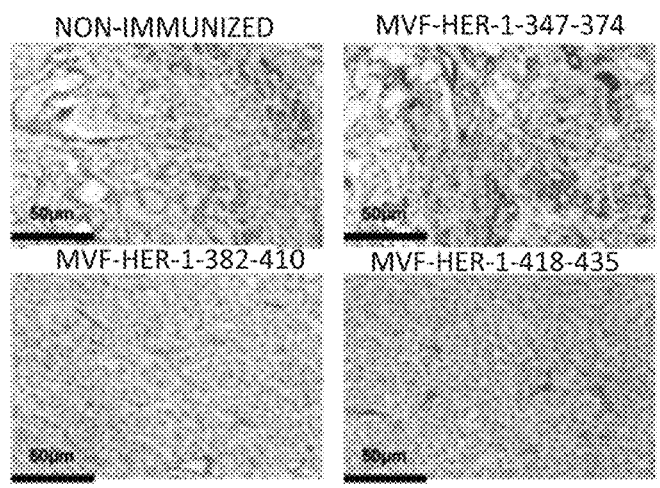
Figure 6E:
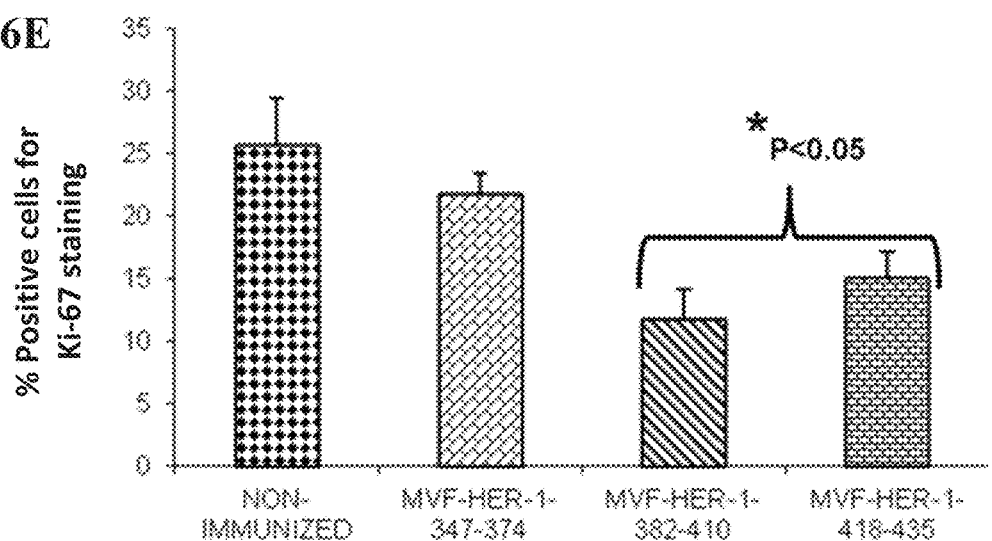
Figure 6F:
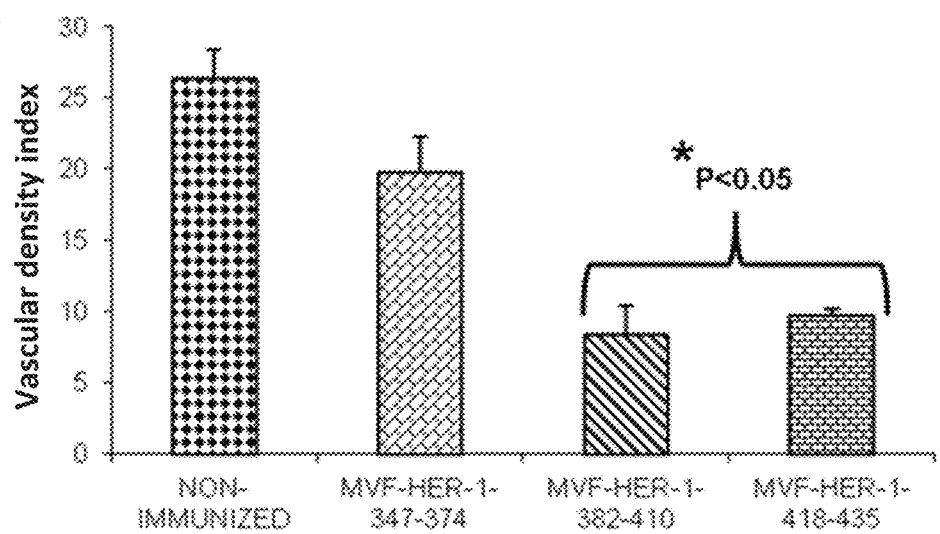

Using immunohistochemical analysis, the effects of vaccine immunization on tumor sections were evaluated by staining for actively dividing cells (Ki-67) and blood vessels (CD31). The number of actively dividing cells was significantly reduced in the case of immunization with the 382-410 and 418-435 vaccine constructs as compared with nonimmunized and the 347 epitope. The staining to show the relative number of positive cells was quantified using Image J software (National Institutes of Health), and indicated a great reduction in the amount of dividing cells (*p, 0.05; FIG. 6C). The blood vessel staining also showed a significant decrease in microvascular density after treatment with the two vaccine constructs, and quantification also indicated a significant reduction in the vascular density index (*p, 0.005; FIG. 6D).

Figure 7A:
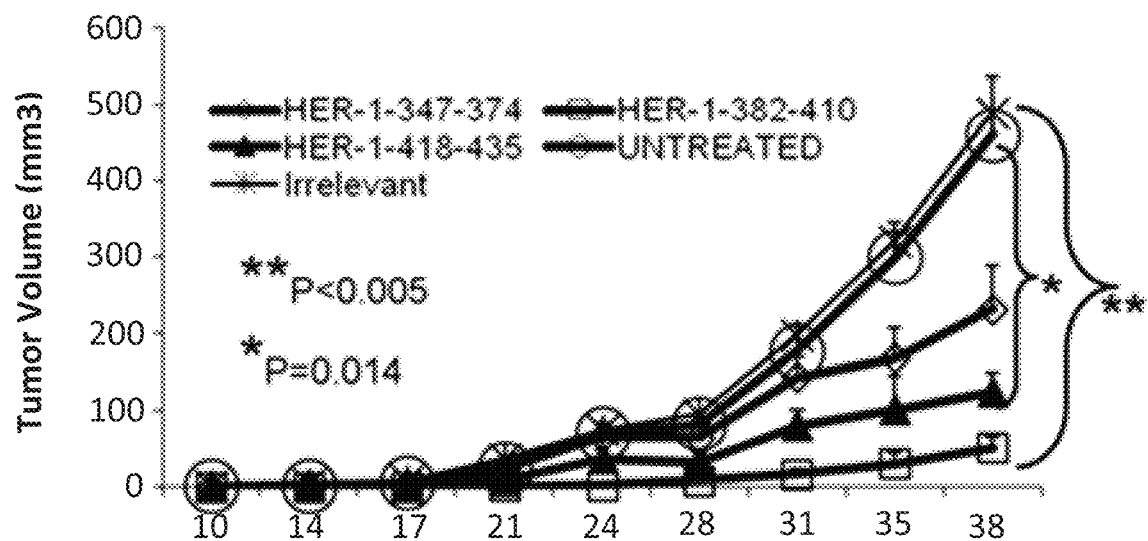
FIG. 7 (A-F) contains graphs and pictures that show the effects of treatment with EGFR (HER-1) peptide mimics in the FVB/n Met-1 transplantable mouse model. (A) Peptide treatment caused a delay in tumor growth, with the 382-410 (**p, 0.005) and 418-435 (*p=0.014) constructs causing a delay in tumor onset of approximately 2 weeks, and the effects were also seen in the percentage tumor weight per body mass as shown in (B) with a significant value of *p, 0.005 for the 382-410 peptide and *p=0.011 for the 418-435 construct. Tumor sections after treatment with peptides were stained for dividing cells using ki-67 (C) and blood vessel density using CD31 (D). Abs and slides were observed under a microscope, and representative photos in each treatment group are shown in (C) and (D). Staining of sections was quantified using the Image J software (National Institutes of Health), and results shown in (E) and (F) represent mean values from three different fields. Error bars represents SD from the mean. The irrelevant peptide (KIEFMYPPPYLD-NERSNGTI) had no inhibitory effects, and the tumor growth results and immunohistochemistry of tumors for Ki-67 and CD31 were almost the same as that of the untreated (results not shown for IHC).
Figure 7B:
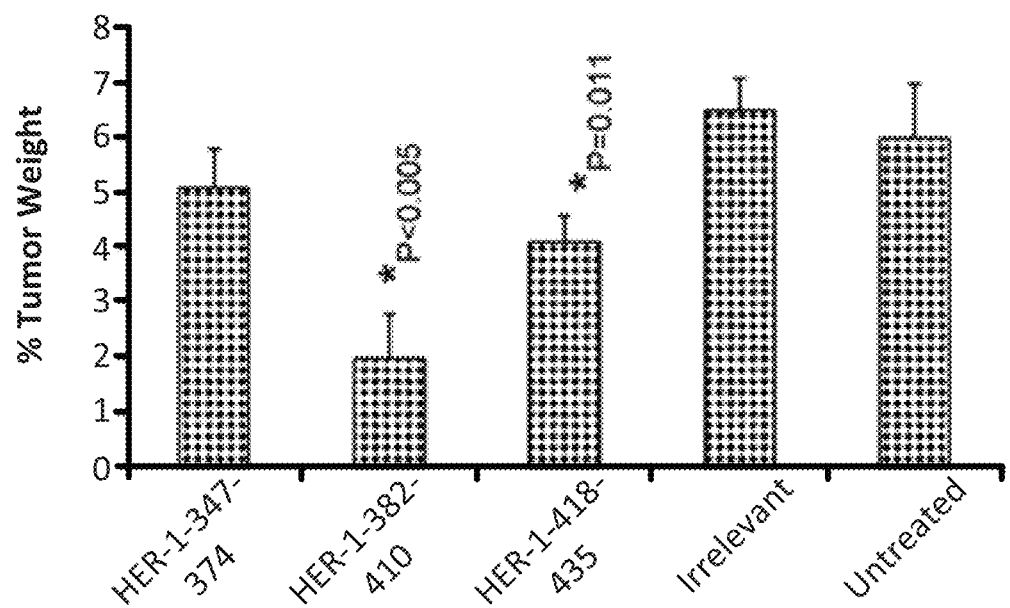
Figure 7C:
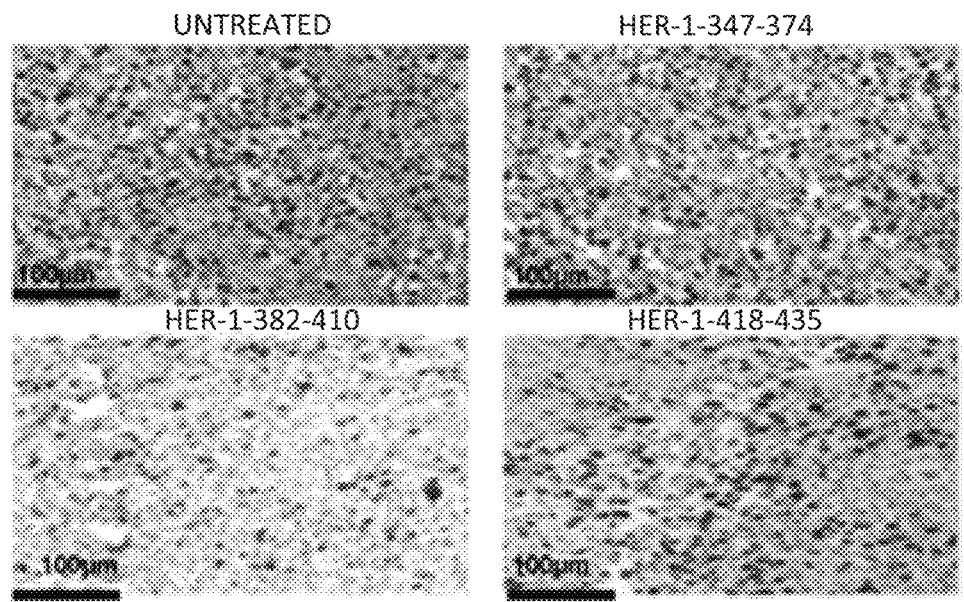
Figure 7D:
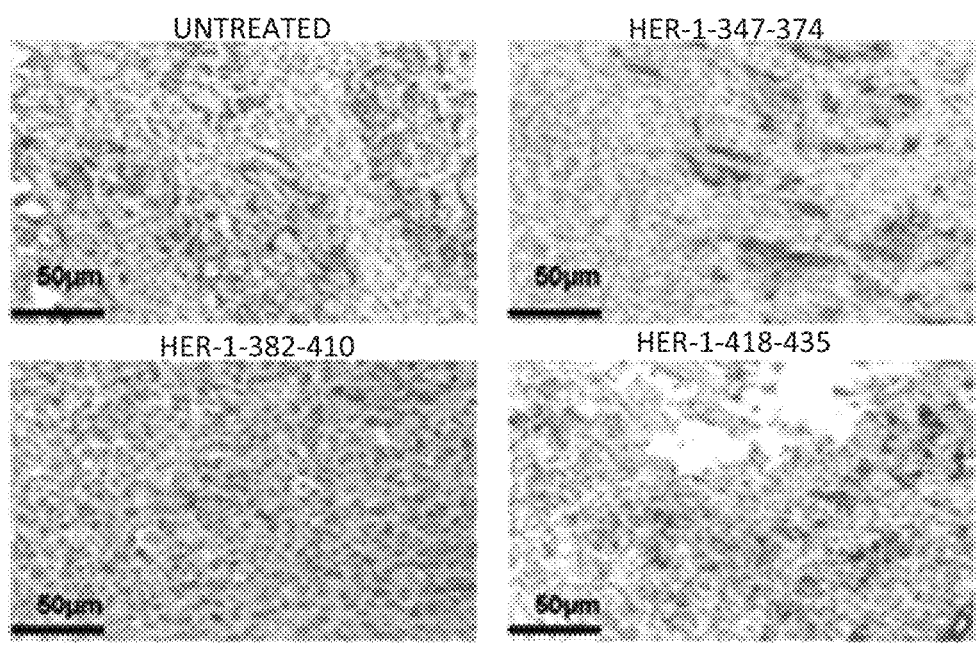
Figure 7E:
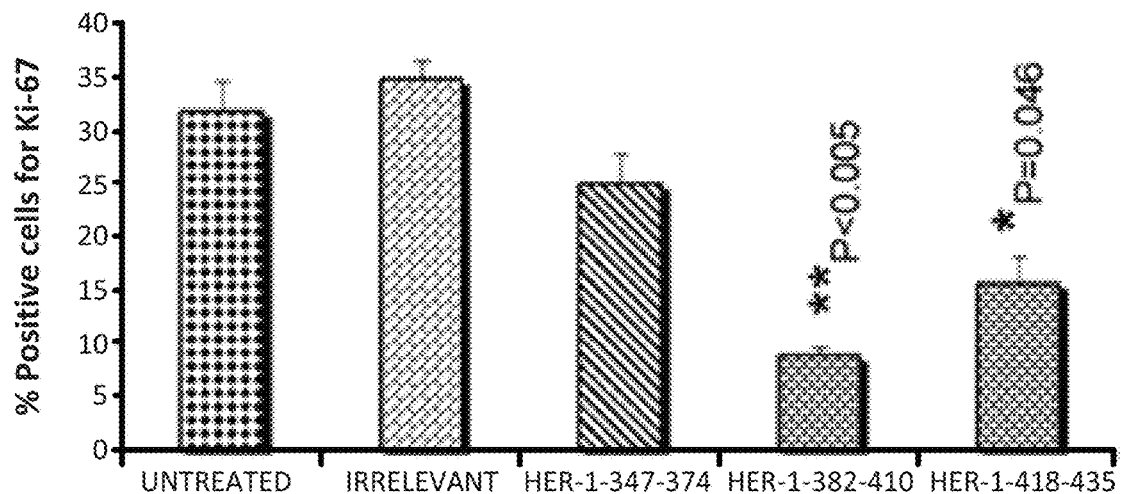
Figure 7F:
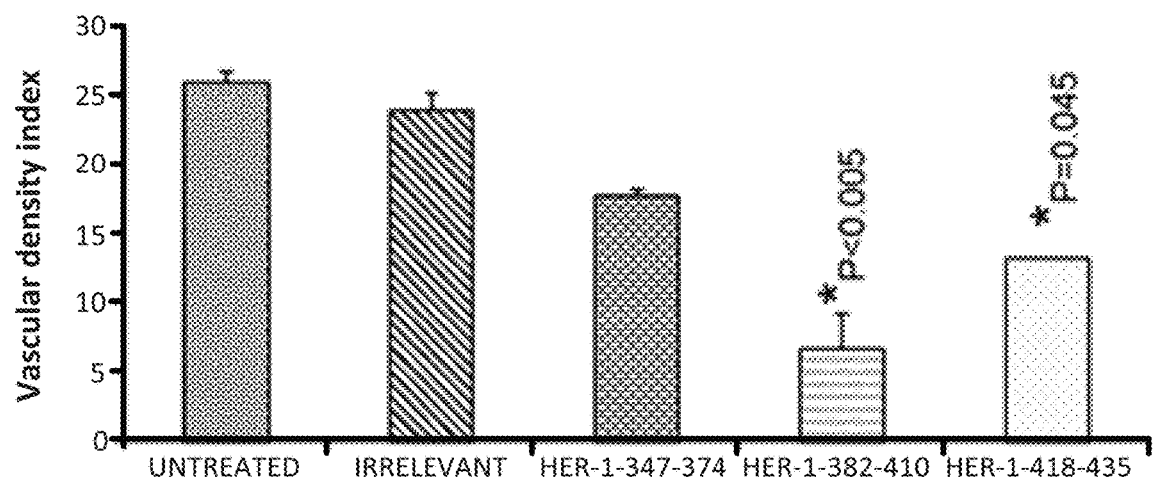

Therapy with HER-1 Peptide Mimics Prevents Tumor Growth In Vivo:

To test the in vivo effects of the peptide mimics, the same FVB/n model was used as in the case of immunization, but in this experiment, wild-type mice were challenged with Met-1 cells and treated i.v. with the peptide mimics. Results obtained showed a decrease in tumor growth and development with both the 382-410 peptide (**p, 0.005, FIG. 7A) and 418-435 peptide (*p=0.014; FIG. 7A) as compared with untreated and irrelevant peptide. The effects on percentage tumor weight also correlated with that of tumor growth, with the 382-410 and 418-435 peptides showing greater inhibitory effects (FIG. 7B). In assessing how the peptide inhibitors exert their effects in vivo, the tumor sections were analyzed after treatment with the peptide mimics for blood vessel density and actively proliferating cells. Tissue sections were stained for Ki-67 and CD31 markers, and results obtained showed a significant reduction in positive cells and vascular density. The effect on proliferating cells was most evident in the case of treatment with the 382-410 and the 418-435 constructs (FIG. 7C). There was also a significant reduction in microvascular density with the same two constructs (FIG. 7D).

Figure 8A:
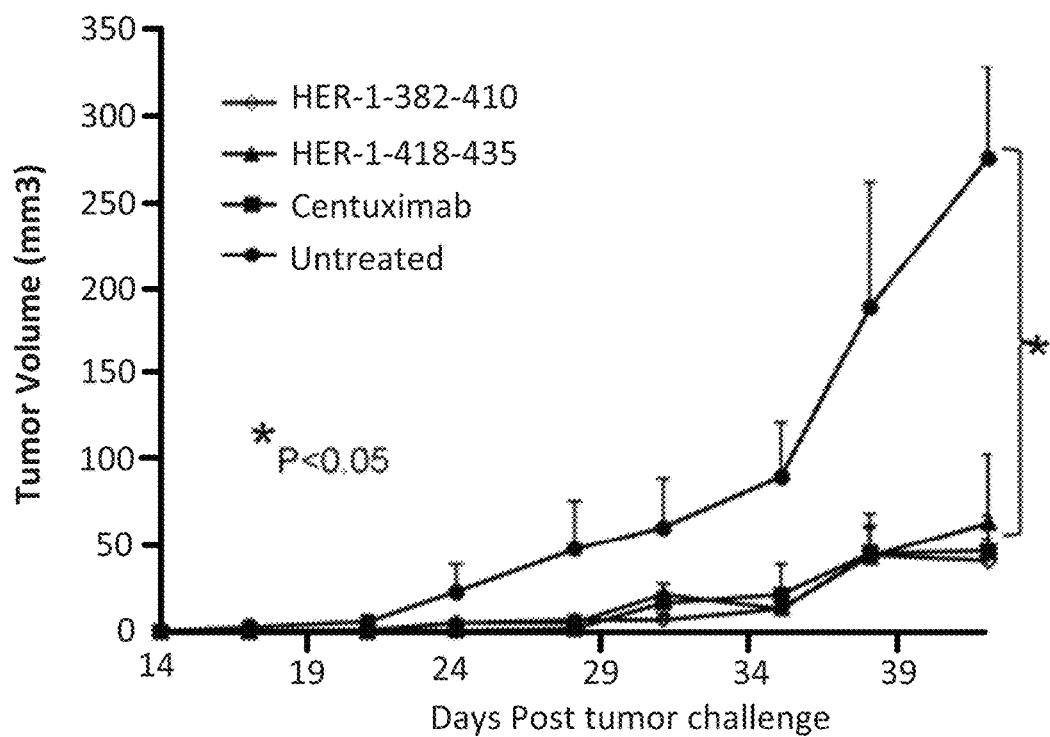
FIG. 8 (A-C) provides graphs showing the effects of treatment with EGFR (HER-1) peptide mimics and vaccine Abs in the transplantable mouse model of lung cancer. (A) Peptide treatment caused a delay in tumor growth, and the two peptides showed significant effects (*p, 0.05) that were comparable to that of cetuximab. (B) The vaccine Abs also showed inhibitory effects that caused a delay in onset of tumor development, but the effects with the 418-435 vaccine epitope (*p=0.004) were even better than that of cetuximab. (C) The effects on percentage tumor weight per body mass were also evaluated, and all of the inhibitors did decrease tumor weight, which was significant in the case of cetuximab (*p=0.015) and vaccine Abs to the 418-435 epitope (*p=0.003).
Figure 8B:
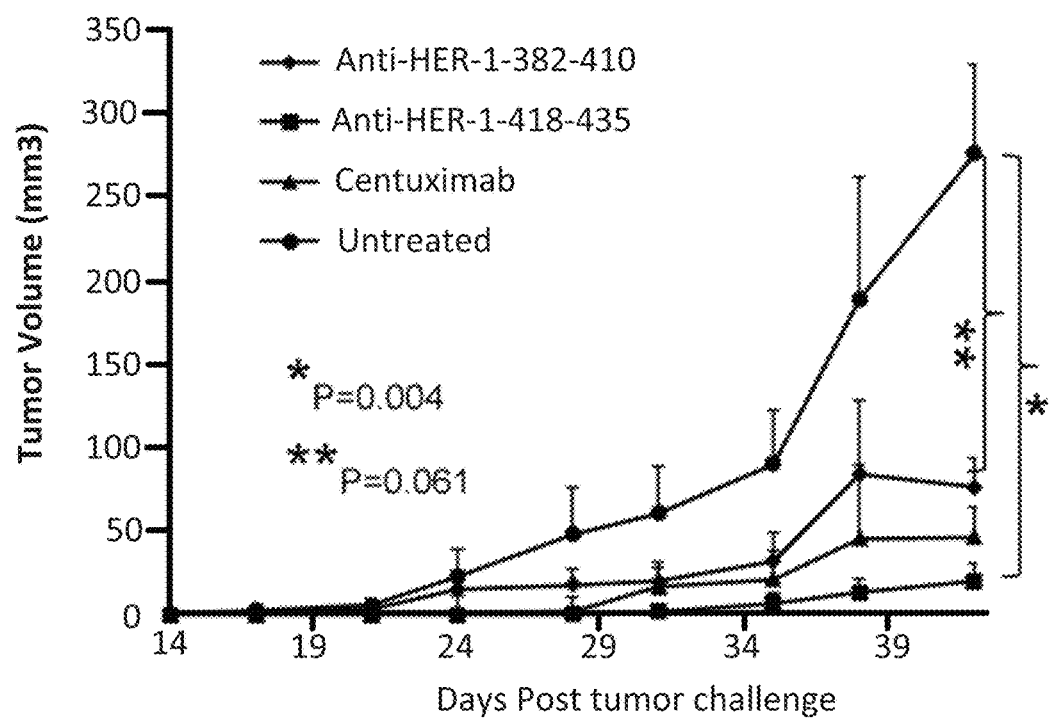
Figure 8C:
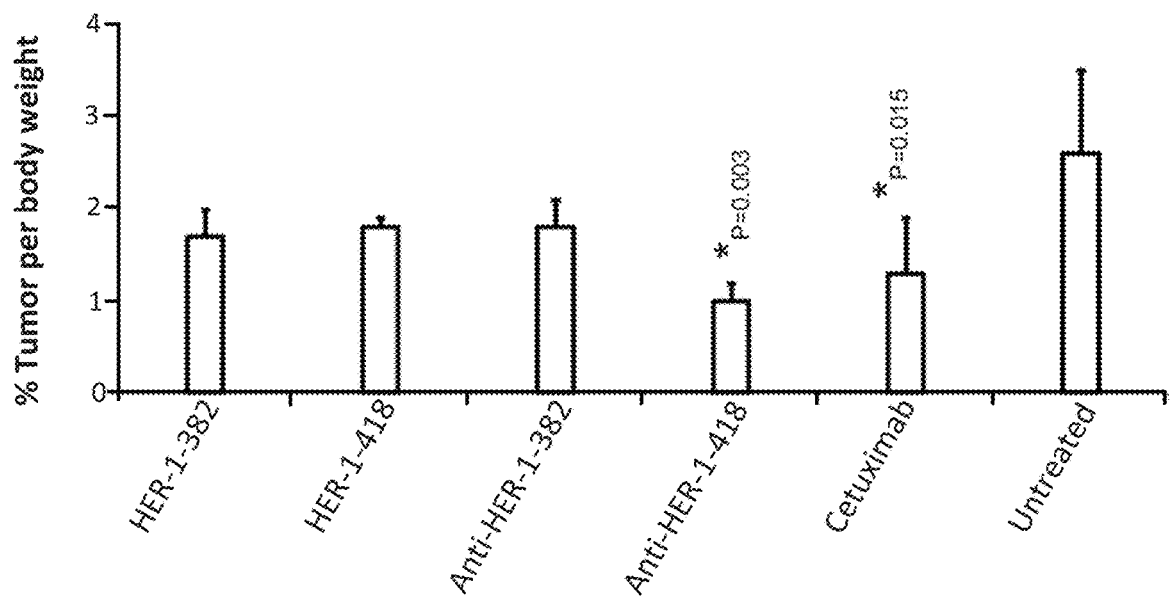

Antitumor Effects of Therapy with HER-1 Peptide Mimics and Peptide Vaccine Abs in Lung Cancer Transplantable SCID Mouse Model:

the inhibitory effects of the HER-1 peptide mimics and peptide vaccine Abs raised in rabbits were further analyzed in a lung cancer transplantable model using BALB/c SCID mice. In this case, only the peptide mimics that showed reasonable inhibition in the breast cancer model (382-410 and 418-435 constructs) were used, and results obtained indicated that both peptide mimics just like cetuximab significantly delayed tumor growth and development (FIG. 8A treatment with peptide mimics); even more striking was the effects of the Abs to the 418-435 epitope that were better than that of cetuximab (FIG. 8B treatment with antipeptide antibodies). Abs to the 382-410 epitope did delay tumor growth, although the effect was not statistically significant. Analysis of the percentage tumor weight per body mass also showed that the Abs to the 418-435 construct was the best inhibitor in this mouse model (FIG. 8C).

Example 3

Synthesis and Characterization of HER-3 Peptide Vaccines and Chimeric Peptides

Synthesis:

In 2002, the crystal structure of the unliganded HER-3 extracellular domain was published by Cho et al [2002. Science 297, 1330-1333]. A ribbon diagram showed that Domains I and III exhibit the expected B-helical structure, and domains II and IV are extended repeats of seven small disulfide-containing modules. Since then, several other crystal structures of the HER-3 extracellular domain have been solved in complex with therapeutic monoclonal antibodies. In 2011, the crystal structure of the HER-3 extracellular domain was published in complex with the Fab portion of a monoclonal antibody, MEDHD7945A (DL11) [Schaefer, G., et al. 2011. Cancer Cell 20, 472-486]. The residues critical for DL11 binding are all found in Domain III of HER3, and these residues are also important for HRG binding. As a result, D11 has the ability to block the HRG: HER-3 interaction and inhibit downstream signaling of HER-3. Several residues are important for DL11 binding, and one peptide was selected that includes these key residues. HER-3 (461-479) directly overlaps with the DL11:HER-3 binding site, and may play a role in signaling of the HER-3 protein. The HER-3 (461-479) epitope includes part of β-strand and α-helix in domain III of HER-3.

In 2013, two other crystal structure complexes were solved for HER3 binding to a monoclonal antibody. The monoclonal antibodies described were RG7116 and LJM716 (Garner, A. P., et al. 2013. Cancer research 73, 6024-6035; Mirschberger, C., et al. 2013. Cancer Res 73, 5183-5194]. The RG7116 monoclonal antibody: HER3 complex demonstrates that this antibody binds to domain I of the HER-3 extracellular region. RG7116 inhibits ligand binding and subsequent phosphorylation of HER-3. As a result, two HER-3 peptides overlapping this binding region were synthesized: HER-3 (99-122) and HER-3 (140-162). In the native HER-3 protein, the HER-3 (99-122) residues fold into an alpha-helix followed by a random coil, while the HER-3 (140-162) peptide contains two anti-parallel β-sheets separated by a random coil. The complex of HER-3 binding to LJM716 demonstrated that the antibody binds to domain 2 and 4 of the HER-3 extracellular region. LMJ716 was shown to lock HER-3 into an inactive conformation and inhibit downstream signaling of the receptor. The residues encompassing the HER-3 (237-269) sequence overlap with the LJM716:HER-3 binding site. These residues encompassing HER-3 (237-269) fold into two anti-parallel β-sheets separated by a random coil in domain II of the HER-3 extracellular region.

Peptide synthesis was carried out on a Milligen/Biosearch 9600 peptide solid phase synthesizer (Bedford, Mass.) using Fmoc/t-butyl chemistry. CLEAR acid resin (0.39 mmol/g) was used for the HER-3 (237-269) and CLEAR amide resin (0.37 mmol/g) was used for the remaining peptides. After synthesis, a fraction of the peptides were cleaved from the resin using cleavage reagent B (trifluoroacetic acid/phenol/water/TIS 90:4:4:2), and crude peptides were purified by semi-preparative reversed-phase HPLC. For the HER-3 chimeric peptides, the remaining peptide resin was linked to a promiscuous T-helper cell epitope derived from the measles virus fusion protein (MVF residues 288-302). Table 2 shows the HER-3 B cell epitope sequences. Peptide mimics were also created wherein the HER-3 B cell epitopes were acetylated and amidated (i.e., Acetyl-XXX-COHN2).

The peptides were synthesized collinearly with the modified MVF epitope (SEQ ID NO:12) and a flexible residue linker (GPSL) to allow independent folding of each epitope (referred to herein as "MVF HER-3 peptides" and "HER-3 chimeric peptides"). After synthesis, cleavage and purification, the MVF HER-3 peptides were characterized by analytical HPLC and MALDI (matrix-assisted laser desorption ionization mass spectroscopy) at Chemical Instrumentation Center (The Ohio State University, Columbus, Ohio). Peptides were then lyophilized and dissolved prior to use in subsequent assays.

Figure 9A:
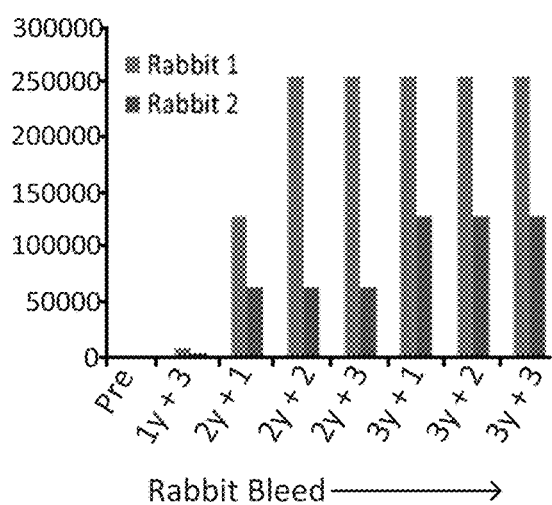
FIGS. 9 (A & B) provides graphs showing the immunogenicity of the MVF HER-3 chimeric peptides. Two rabbits were immunized with either MVF HER-3 (237-269) or MVF HER-3 (461-479) every three weeks for a total of three immunizations. Anti-peptide antibody titers were determined by ELISA. Titer is shown on the y-axis and was defined as the reciprocal of the highest dilution of sera that gave an absorbance reading over 0.2.
Figure 9B:
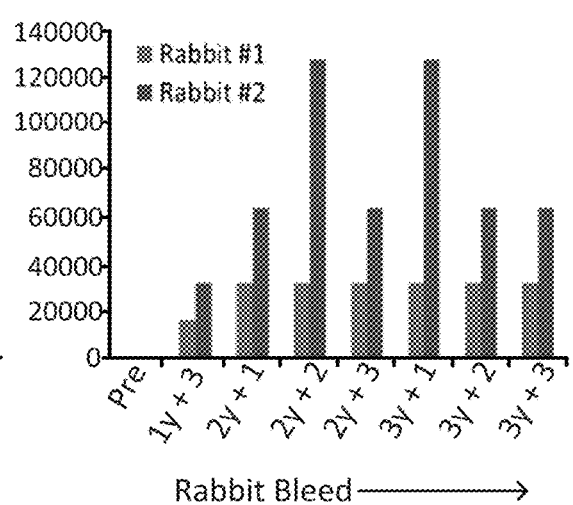

Immunogenicity of the MVF HER-3 Peptide Constructs and Antibody Purification:

Two female New Zealand white outbred rabbits (Harlan) were immunized intramuscularly with 1 mg of MVF HER-3 (237-269) or MVF HER-3 (461-479) peptide dissolved in 500 μL PBS and emulsified in 500 μL of Montanide ISA720 vehicle with 100 μg muramyl dipeptide adjuvant, nor-MDP (N-acetylglucosamine-3yl-acetyl-L-alanyl-D-isoglutamine). Subsequent booster injections were given every three weeks after primary immunization. Sera of rabbits immunized with either MVF peptide were collected weekly, and complement was inactivated by heating to 56° C. for 30 minutes. The titer of anti-HER-3 peptide antibodies were quantified by ELISA. The MVF HER-3 (237-269) and MVF HER-3 (461-479) peptides were highly immunogenic by three weeks after the third immunization. Antibody titers against MVF HER-3 (461-479) and MVF HER-3 (237-269) were ≥32,000 and ≥128,000, respectively (FIGS. 9 A & B). High antibody titers were also generated against B cell epitope constructs. HER-3 (461-479) and HER-3 (237-269) antibody titers were ≥16,000 and ≥128,000, respectively (Data not shown). Total IgG was purified from high-titered sera on a protein A/G column (Pierce, Rockford, Ill.) and eluted antibodies were concentrated and exchanged in PBS using 100 kDa cutoff centrifuge filter units (Millipore). Antibody concentrations were determined by Coomassie plus protein assay reagent kit (Pierce).

Figure 10:
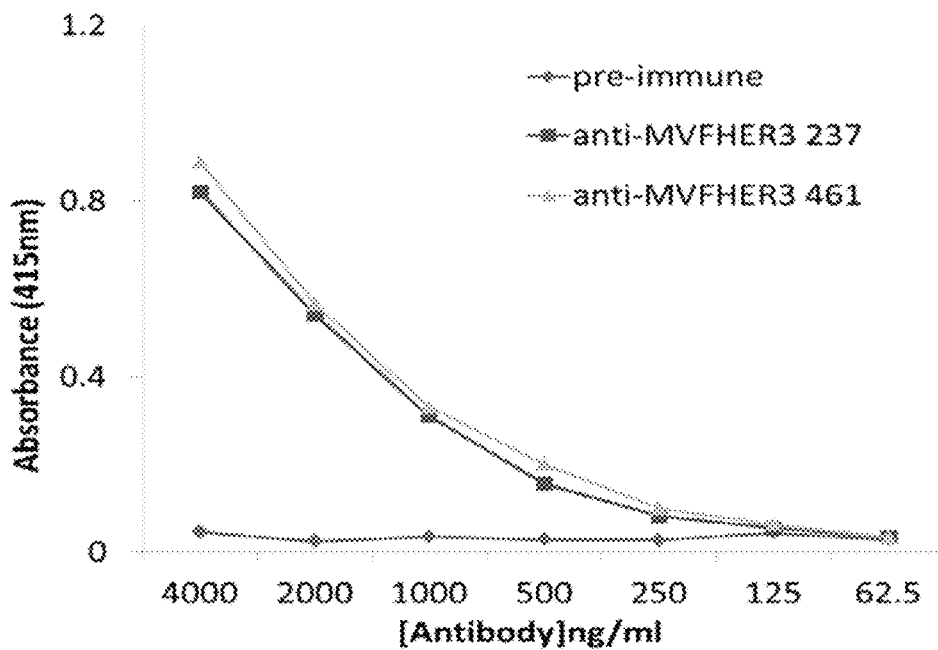
FIG. 10 is a graph showing that anti-HER-3 peptide antibodies recognize rh HER-3. Anti-HER-3 peptide antibodies were purified from high tittered rabbit anti-serum on a protein A/G column. The ability of the peptide specific antibodies to recognize rh HER-3 was determined by ELISA. The results of the anti-HER-3 antibodies were compared to preimmune antibodies.

Direct Binding of Anti-HER3 Peptide Antibodies to the Native HER-3 Receptor:

The ability of the MVF HER-3 peptides to stimulate the production of antibodies that can specifically bind to the native HER-3 receptor was explored. The ability of HER-3 anti-peptide antibodies to recognize and bind to recombinant human HER-3 protein was tested in an ELISA (FIG. 10). Ninety-six well plates were coated with 100 µL of recombinant human HER-3 at 2 ug/ml in PBS overnight at 4° C. Nonspecific binding sites were blocked for 1 hour with 200 µL PBS-1% BSA, and plates were washed with PB ST. Anti-HER-3 (237-269) antibodies in PBT were added to antigen-coated plates in duplicate wells, serially diluted 1:2 in PBT, and incubated for 2 hours at room temperature. After washing the plates, 100 µL of 1:500 goat anti-rabbit IgG conjugated to horseradish peroxidase (Pierce) were added to each well and incubated for 1 hour. After washing, the antibody was detected using 50 µL of 0.15% H2O2 in 24 mM citric acid and 5 mM sodium phosphate buffer (pH 5.2) with 0.5 mg/ml 2,2'-aminobis(3ethylbenzthiazole-6-sulfonic acid) as the chromophore. Color development proceeded for 10 minutes, and the reaction was stopped with 25 µL of 1% SDS. Absorbance was read at 415 nm using a BioRad Benchmark ELISA plate reader (Hercules, Calif.). FIG. 10 shows that the MVF HER-3 anti-peptide antibodies were able to specifically recognize their respective epitopes when the rh HER-3 was used as an antigen in the ELISA assay.

Figure 11:
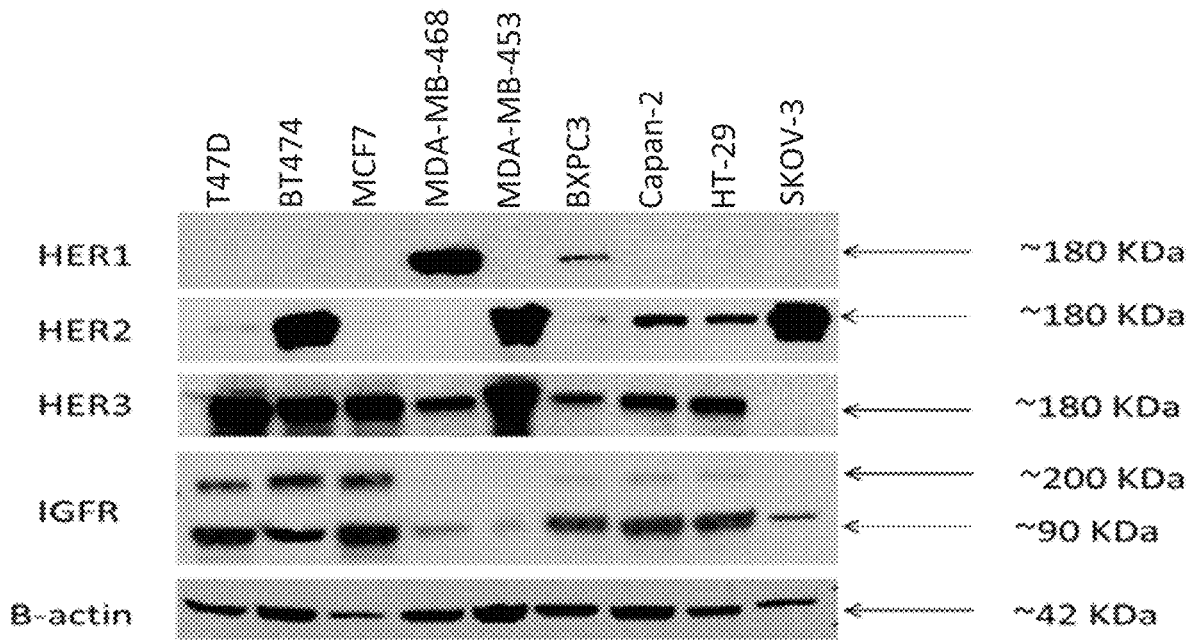
FIG. 11 is a Western blot analysis of HER-1, HER-2, HER-3 and IGF-1R expression in various cancer cell lines. Cells were grown to 70-80% confluency prior to cell lysis. Commercial antibodies were used to probe for expression of the different receptors.

HER-3 Expression in Cancer Cell Lines:

Western blotting for total Erbb3, Erbb1, Erbb2 and IGFR (R & D Systems) was performed to determine total protein expression in cancer cell lines. One million cells/well were plated in 6 well plates and incubated at 37° C. until cells were 70-80% confluent. Culture media was then removed from the wells, and cells were washed with PBS. Cells were lysed with 1×RIPA Lysis Buffer (R+D systems) for 2.5 hours at 4° C. Cell lysates were spun at 13000×g and debris-free supernatants were transferred into clean tubes. Protein concentration of each sample was measured by Coomassie plus protein assay reagent kit (Pierce). Lysates were frozen at −80° C. Protein expression was measured using western blotting with rabbit polyclonal antibodies for HER-1 (Cell Signaling #4405), HER2 (Cell Signaling #4290), HER-3 (Santa Cruz sc-285) and IGFR (Cell Signaling #9750). A β-actin antibody (Abcam Ab8227) was used to control for loading. Detection was accomplished using goat anti-rabbit HRP secondary antibody (Bio-rad 170-5046) and Immun-Star™ HRP Chemiluminescent Kit (Bio-Rad). All procedures were performed according to the manufacturer's instructions. HER-3 expression was detected in all cell lines except SKOV-3 cells (FIG. 11).

Figure 12A:
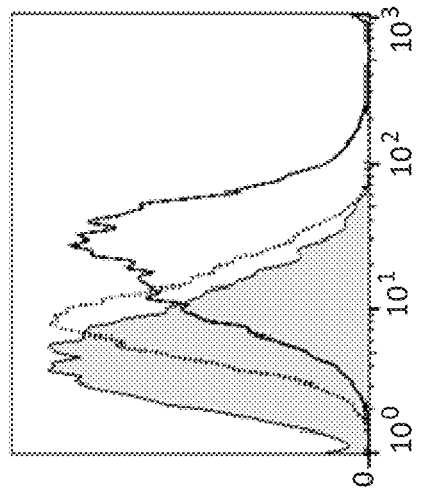
FIG. 12 (A-C) contains histograms showing the direct binding of anti-peptide antibodies to the native HER-3 receptor. The figure shows flow cytometric analysis of BXPC3 (A), HT-29 (B) and Capan-2 (C) cells. Preimmune is shown with gray fill, anti-MVF HER-3 461 is shown in solid line, and anti-MVF HER-237 is shown in dotted line. The y-axis shows count and the x-axis shows FLH-1.
Figure 12B:
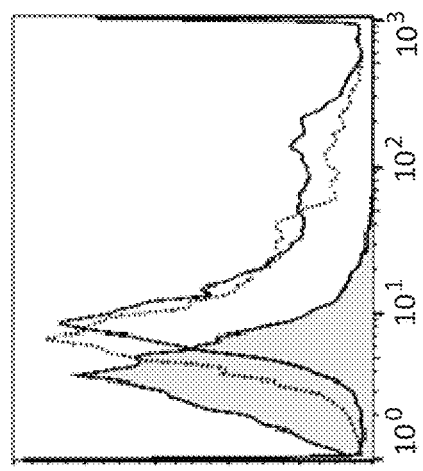
Figure 12C:
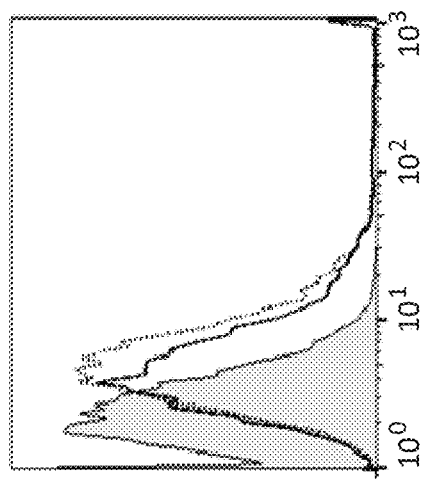

Direct Binding of Anti-HER-3 Peptide Antibodies to Native HER-3:

The ability of the HER-3 vaccine antibodies to bind to the surface of HER-3 positive cancer cells was also determined. Flow cytometric analysis was conducted with HER-3 expressing BXPC3, Capan-2 and HT-29 cells (FIG. 12). Five×$10^5$ cells were washed twice in 1 mL of staining buffer (PBS, 1% BSA, 0.02% sodium azide). After washing, cells were treated with 5 µg of an anti-HER-3 peptide antibody in 100 µL staining buffer for 60 minutes. Following incubation, cells were washed twice with 1 mL staining buffer and treated for 30 minutes with 1:100 dilution of goat anti-rabbit IgG-Alexa Fluor 488 secondary antibody (Invitrogen) in 100 µL staining buffer. After washing, cells were fixed in 3.7% paraformaldehyde in PBS and analyzed on a BD FACSCalibur system (DHRLI Flow Cytometry Core Lab, OSU. Pre-immune antibodies were used as the negative control. The antibodies elicited by the MVF-HER-3 (237-269) and MVF-HER-3 (461-479) constructs bound to the HER-3 protein expressed by the cell lines (FIG. 12).

Figure 13A:
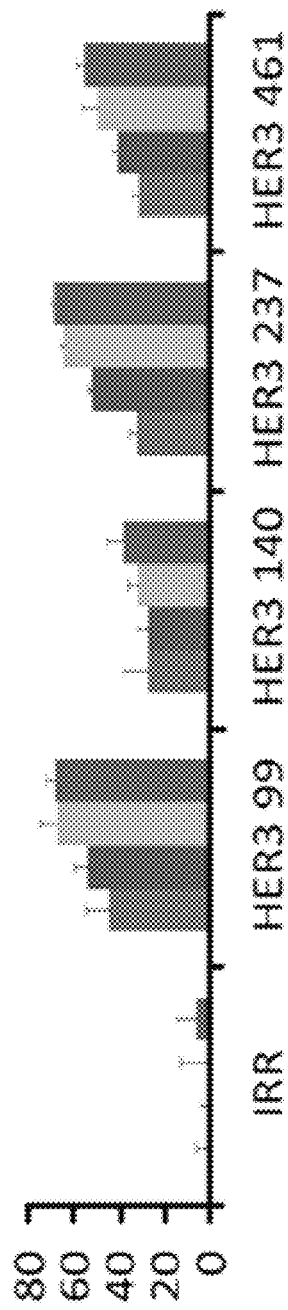
FIG. 13 (A-C) contains graphs showing that HER-3 peptide mimics inhibit proliferation of HER-3 positive cancer cell lines. Cells were treated with peptide mimics for 1 hour prior to ligand stimulation. After 72 hours of incubation in the presence of peptide mimics at using 25 µg/ml, 50 µg/ml, 100 µg/ml and 150 µg/ml (shown left to right), MTT was used to measure cell proliferation. Percent inhibition as shown on the y axis was calculated by taking absorbance readings at 570 nm and using the following equation: (untreated−treated)/untreated×100.
Figure 13B:
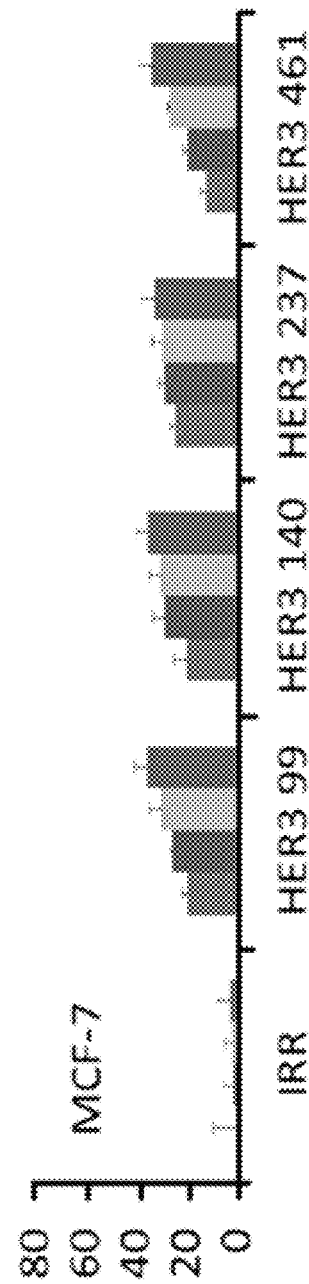
Figure 13C:
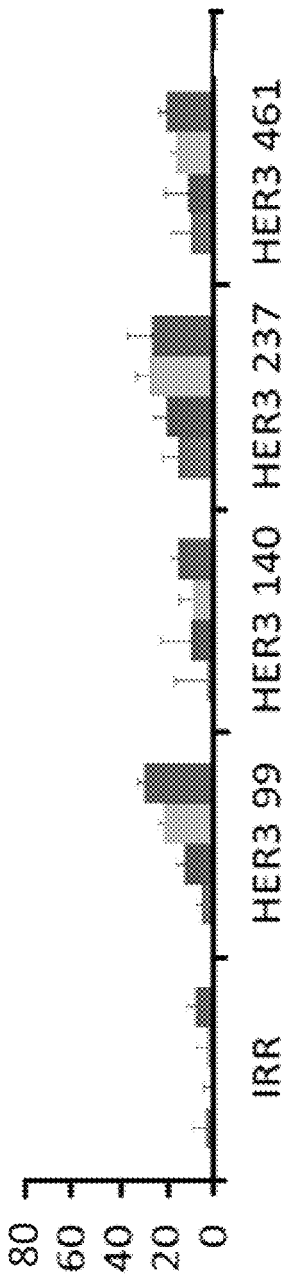

MTT Inhibition Assay with Peptide Mimic Constructs:

The HER-3 peptide mimics and peptide vaccine antibodies may provide anti-tumor activity by blocking dimerization or ligand binding of the HER-3 receptor. To test the ability of the chimeric peptides to elicit antitumor effects, HER-3 positive cells were examined in a MTT inhibition assay. The anti-proliferative effects of the peptide mimics were tested at various concentrations (FIG. 13). Taxol, an inhibitor of mitosis, was used as a positive control (data not shown). Cells were seeded in 96 well flat bottom plates at 1×$10^4$ cells/well in 100 µl growth media and allowed to adhere overnight at 37° C. Media was removed from the wells and replaced with HER3 peptides made up in 1% growth media. Plates were incubated for 1 hour at 37° C., and subsequently stimulated with either 50 ng/mL HRG. Plates were incubated an additional 72 hours at 37° C. before 25 µL of 5 mg/mL MTT was added to each well. Plates were incubated for 2 hours at 37° C., then 100 µL extraction buffer (20% SDA, 50% DMF, pH 4.7) was added. Plates were incubated overnight at 37° C. and read on an ELISA reader at 570 nm. Percent inhibition was calculated by the following equation: (untreated-treated)/untreated×100. Error bars represent SEM of three separate experiments. FIG. 13 shows various cancer cells treated with either the HER3 chimeric peptides. The HER-3 peptide mimics inhibited proliferation of BXPC3, MCF-7 and JIMT-1 cell lines in a dose-dependent manner. The most robust response was observed when BxPC3 cells were treated with the HER-3 99-122 peptide (almost 80% inhibition).

HER-3 Peptide Mimics and Vaccine Antibodies Elicit Apoptosis:

Cancer cells were assayed for apoptosis by using the Caspase 3/7 Glo kit (Promega). Briefly, cells were seeded in 96 well plates and incubated at 37° C. for 24 hours. Cells were then treated with the anti-peptide antibodies in low serum media and allowed to incubate for a day. After treatment, apoptosis was evaluated by using the caspase glo reagent, which measures total release of caspases 3 and 7. Results obtained showed a significant increase in the amount of caspase activity when compared to the negative control (normal rabbit IgG or IRR peptide), indicating that the HER-3 chimeric peptides and vaccine antibodies can induce apoptosis (FIG. 14 A-F).

Figure 15A:
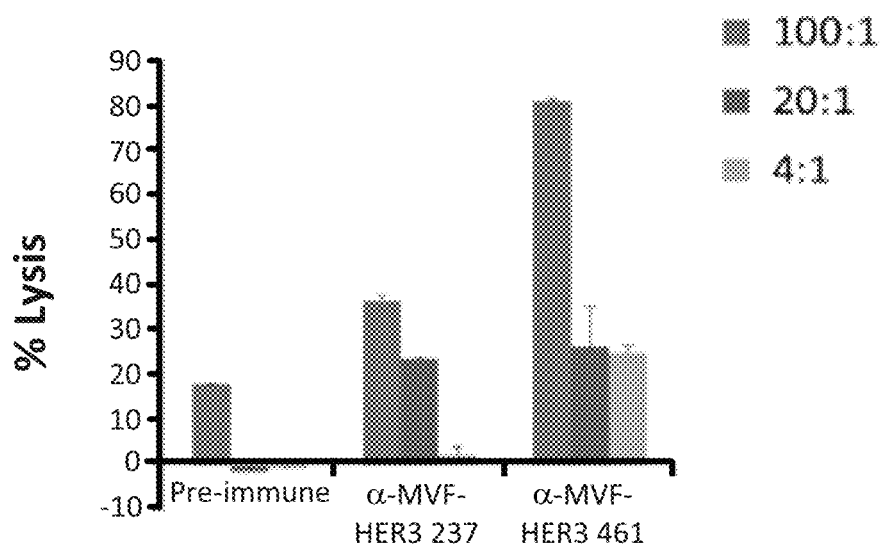
FIGS. 15 (A & B) contains graphs showing that MVF HER-3 antibodies have the ability to elicit ADCC in HER-3 positive cancer cells Bx-PC3 (A) and MCF7 (B). Target cells were seeded and incubated in the presence of human PBMCs at different effector:target cell ratios (11:1, 20:1, 4:1). Cells were then treated for one hour with MVF HER-3 antibodies prior to cell lysis. Results display the % lysis of treatment groups when compared to 100% target cell lysis.
Figure 15B:
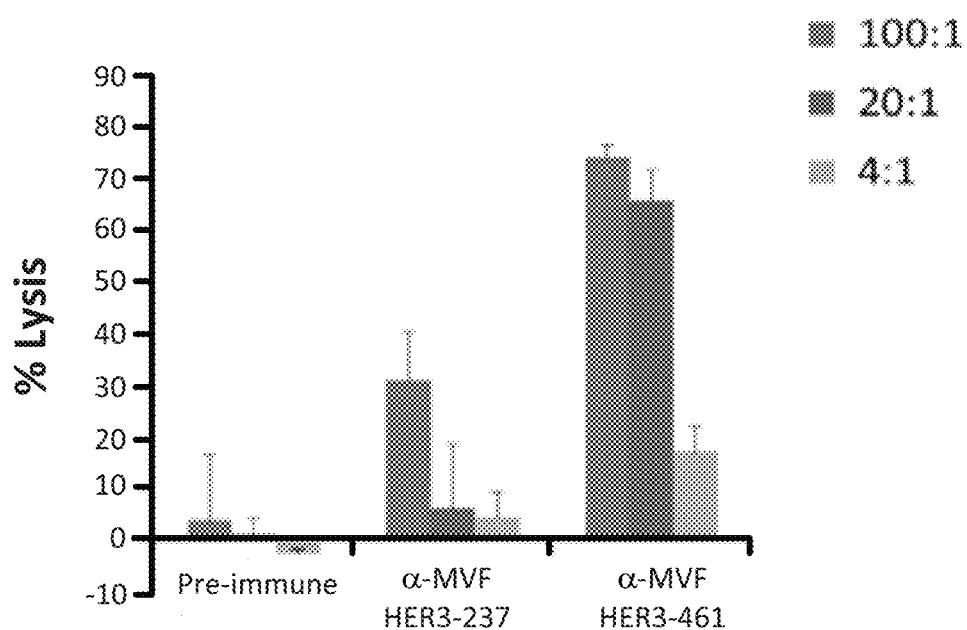
Figure 16A:
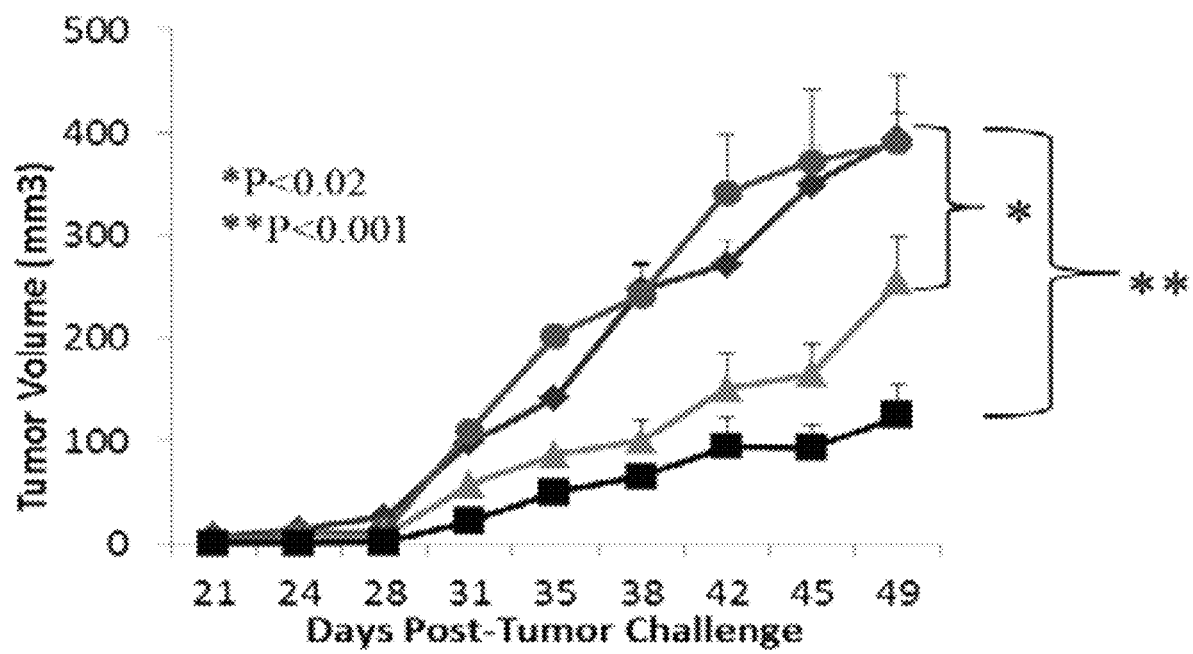
In FIG. 16(A), diamonds show untreated, circles show IRR treated, triangles show HER-3 (237-269) treated and squares show HER-3 (461-479) treated.
Figure 16B:
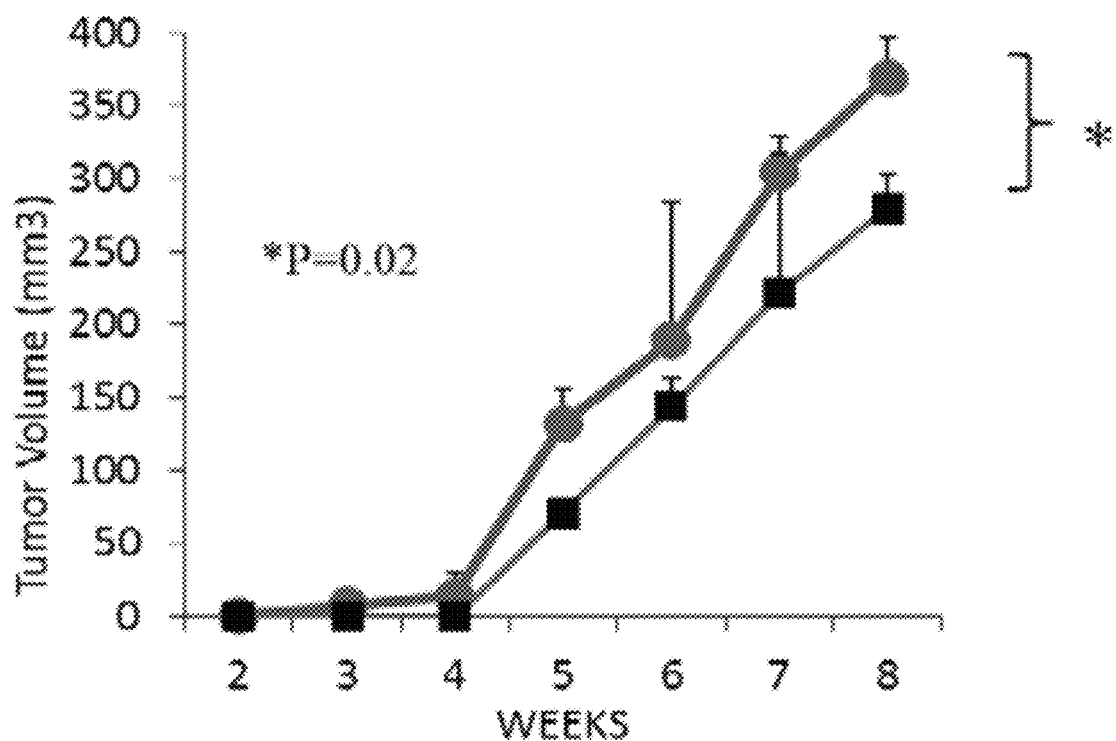
In FIG. 16(B), circles show IRR treated and squares show HER-3 (461-479) treated.
Figure 16C:
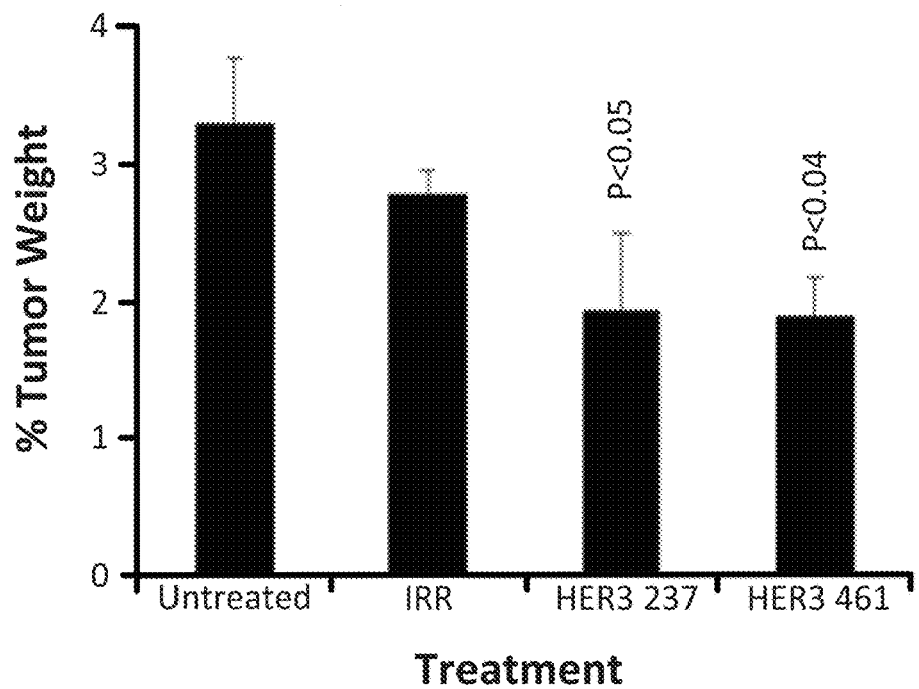
FIG. 16 (A-D) contains graphs showing that HER-3 peptide mimics delay tumor growth in two transplantable mouse models. Mice were challenged with either BXPC3 (A, C) or JIMT-1 (B, D) cells and treated weekly with peptide mimics. Results displayed include tumor volume over time (A & B) and % weight of tumors when compared to total mouse weight (C & D).
Figure 16D:
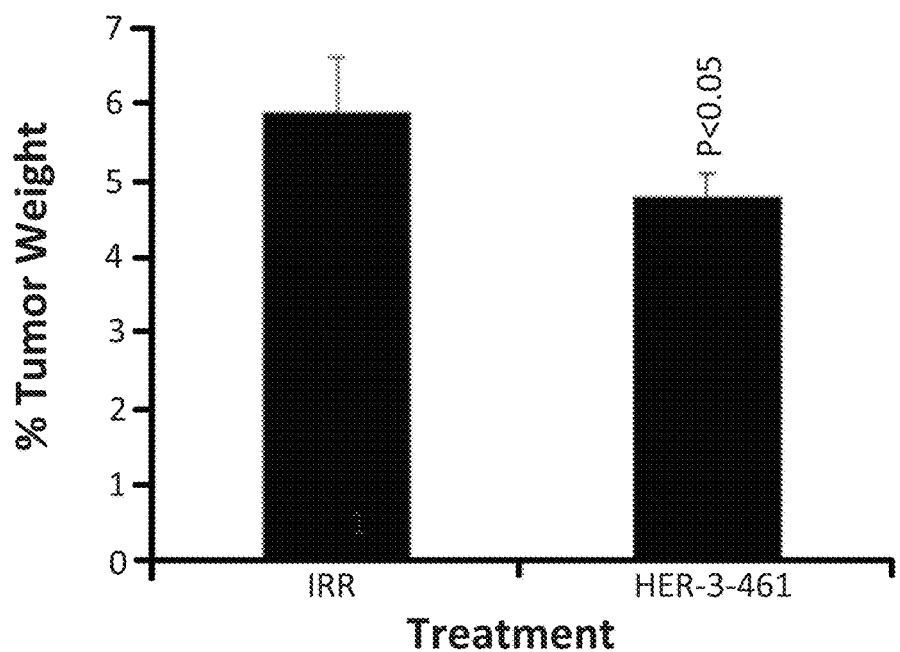

HER-3 Anti-Peptide Antibodies Mediate ADCC:

Antibodies can exert their anti-tumor effects via ADCC. As a result, the ability of the HER-3 vaccine antibodies to induce ADCC against various cancer cell lines was investigated (FIGS. 15 A & B). Briefly, target cells (BXPC3 or MCF-7 cells) were plated and treated for 30 minutes with the vaccine antibodies. Following treatment, human PBMCs were added as the effector cells at different concentrations (effector:target ratios included 100:1, 20:1 and 40:1). ADCC was then assayed by using the aCella-tox kit to measure the amount of target cell lysis (Cell signal). Results display the percent cell lysis when compared to maximum target cell lysis. The antibodies elicited by the HER-3 vaccines were capable of inducing ADCC. The HER-3 (461-479) antibodies demonstrated more ADCC than the HER-3 (237-269) antibodies.

HER-3 Peptide Mimics and Two Transplantable Mouse Models (BALB/c SCID Mice and BXPC3 Cells or JIMT-1 Cells):

To test the in vivo effects of the peptide mimics, two transplantable mouse models were used. Mice 4-5 weeks old were challenged with either BXPC3 or JIMT-1 cells subcutaneously into the flank. After tumor challenge, mice were treated intravenously with the peptide mimics starting at day zero (day of tumor challenge) and weekly for a total of 8-9 treatments. Tumor growth was monitored twice weekly and at the end of treatment. All mice were euthanized and weighed. Tumors were also extracted and weighed. Results display tumor volume and % tumor weight (FIG. 16 A-D). Both peptide constructs had the ability to attenuate tumor growth in mice challenged with BXPC3 cells. The HER-3 (461-479) peptide construct showed greater anti-tumor effects and significantly decreased the % tumor weight. As a result, only the HER-3 (461-479) peptide was used in JIMT-1 tumor model.

Figure 17A:
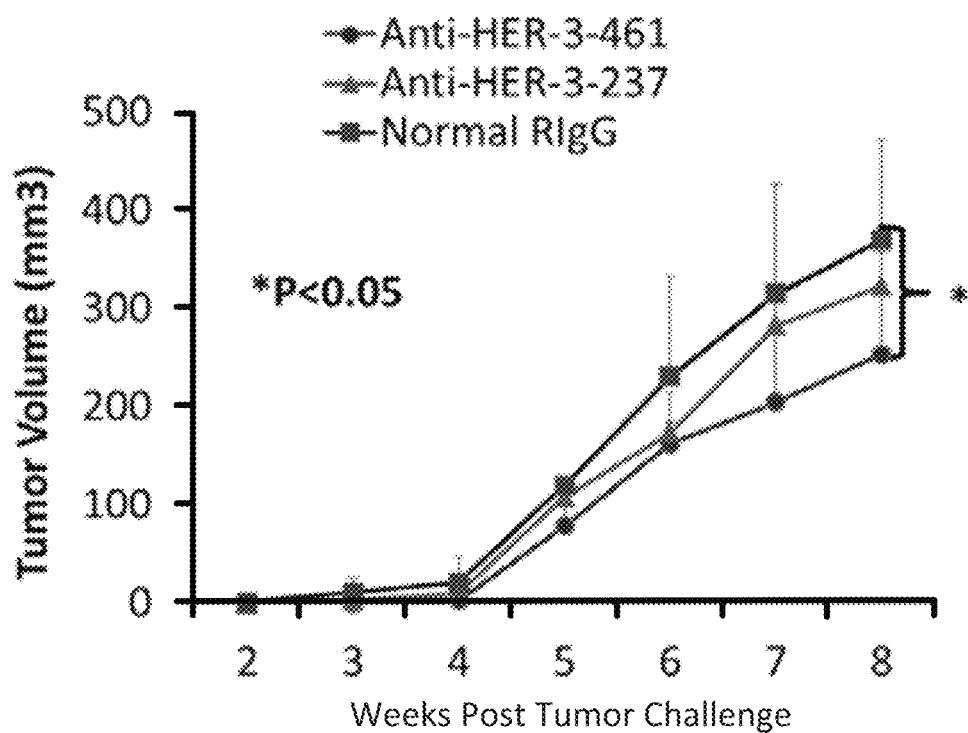
FIGS. 17 (A & B) contains graphs showing that MVF HER-3 antibodies delay tumor growth in a transplantable mouse model. Mice were challenged with JIMT-1 cells and treated weekly with MVF HER-3 antibodies. Results displayed include tumor volume over time (A) and % weight of tumors when compared to total mouse weight (B).
Figure 17B:
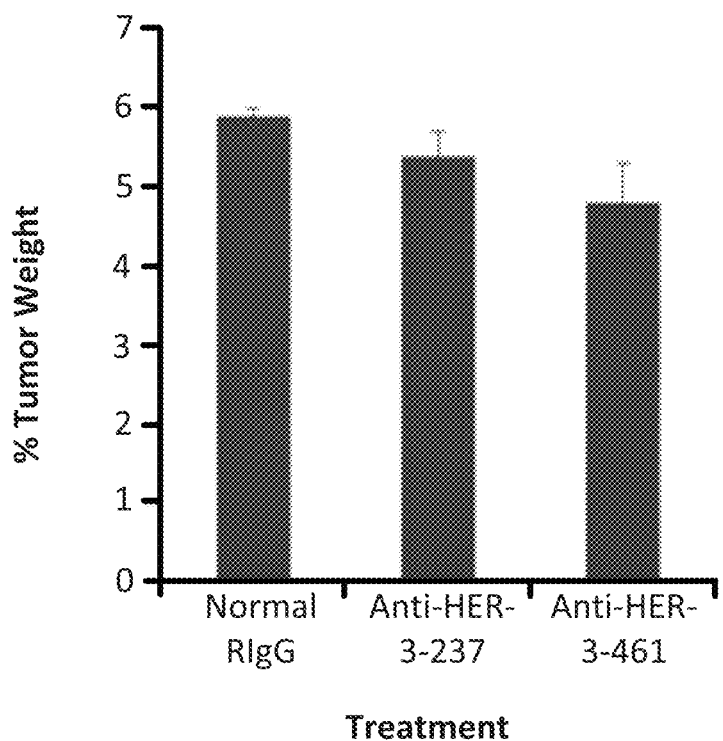

HER-3 Vaccine Antibodies and a Transplantable Mouse Model (BALB/c SCID Mice and JIMT-1 Cells):

To test the in vivo effects of the anti-peptide antibodies, a transplantable mouse model was used. Mice 4-5 weeks old were challenged with JIMT-1 cells subcutaneously into the flank. After tumor challenge, mice were treated intravenously with the anti-peptide antibodies starting at day zero (day of tumor challenge) and weekly for a total of 8 treatments. Tumor growth was monitored weekly and at the end of treatment. All mice were euthanized and weighed. Tumors were also extracted and weighed. Results display tumor volume and % tumor weight (FIGS. 17 A & B). Only mice treated with the MVF HER-3 (461-479) vaccine antibodies resulted in a significant delay of tumor growth.

Example 4

Synthesis and Characterization of IGF-1R Peptide Vaccines and Chimeric Peptides

Synthesis:

Peptide synthesis was performed using 9600 Milligen/Biosearch solidphase peptide synthesizer (Millipore, Bedford, Mass.) using Fmoc/t-But chemistry. Clear amide resin (0.32 mmol/gm) (Peptide International, Louisville, Ky.) was used for synthesis of all of the peptides. In the case of the peptide vaccines, the B cell epitopes were colinearly synthesized with the promiscuous Th MVF epitope using regioselective side chain protections. After synthesis, the peptides were cleaved from the resin as described above. The crude peptides were purified by reverse phase HPLC in a gradient system using a C-4 vydac column in water/acetonitrile (0.1% trifluoroacetic acid) on a Waters system. At the end of purification, the pure fractions were then analyzed in analytical HPLC, and fractions of interest were pooled together and lyophilized in 1% acetic acid solution. The final purified peptides were then identified using electrospray ionization mass spectrometry (Campus Chemical Instrumentation Center, The Ohio State University, Columbus, Ohio). Table 3 above shows the IGF-1R epitope sequences. Peptide mimics were also created wherein the IGF-1R B cell epitopes were acetylated and amidated (i.e., Acetyl-XXX-COHN2).

Figure 18A:
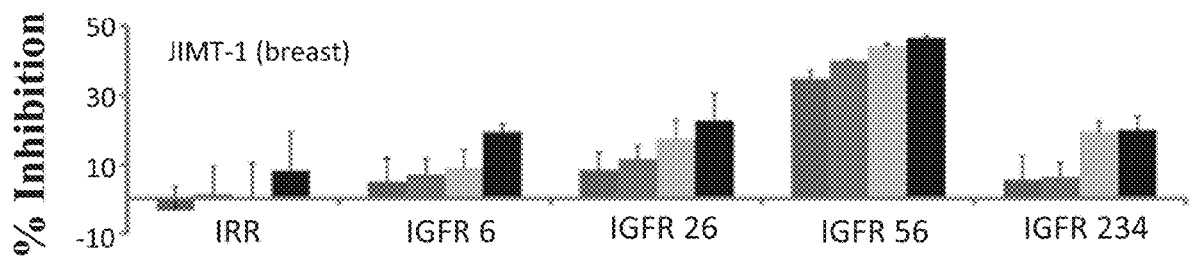
FIG. 18 (A-C) contains graphs showing that IGF-1R peptide mimics are able to prevent cancer cell proliferation in an MTT assay. Results from three different cancer cell lines (JIMT-1, MCF-7 and BxPC-3) show that IGF-1R (56-81) and IGF-1R (234-252) caused dose-dependent inhibition of proliferation using 25 µg/ml, 50 µg/ml, 100 µg/ml and 150 µg/ml (shown left to right).
Figure 18B:
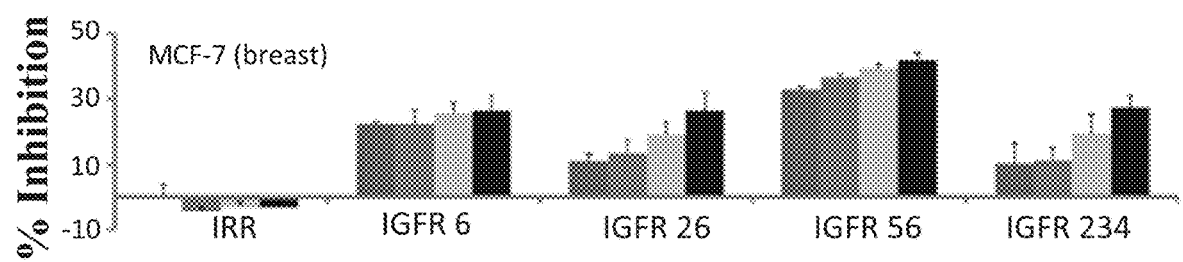
Figure 18C:
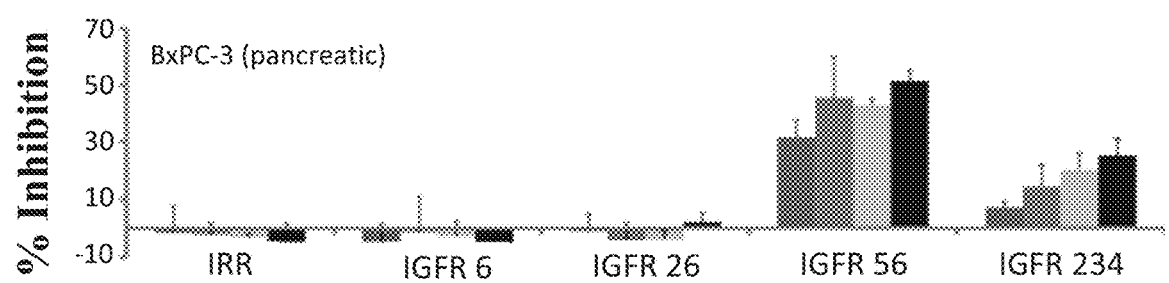

IGF-1R Peptide Mimics Inhibit Proliferation of Ovarian and Pancreatic Cancer Cells:

The effects of treatment with the IGF-1R peptide mimics were evaluated as inhibitors on proliferation of human pancreatic (BxPC-3) and breast (MCF-7 and JIMT-1) cancer cells. Ligand binding to the IGF-1 receptor results in activation that causes increase proliferation of the receptor and intracellular signaling. Accordingly, the effects of the IGF-1R peptide mimics on ligand binding inhibition and inhibition of cancer cell line proliferation were determined. To measure proliferation, the MTT assay was used where the cells were treated with the inhibitors at different concentrations and incubated for three days before adding MTT. The peptide mimics were able to prevent cancer cell proliferation as shown in FIG. 18 (A-C). Results from the three different cancer cell lines showed that the IGF-1R (56-81) and the IGF-1R (234-252) were the two best epitopes because both epitopes caused an inhibition of all three cell lines which was dose dependent.

Figure 19A:
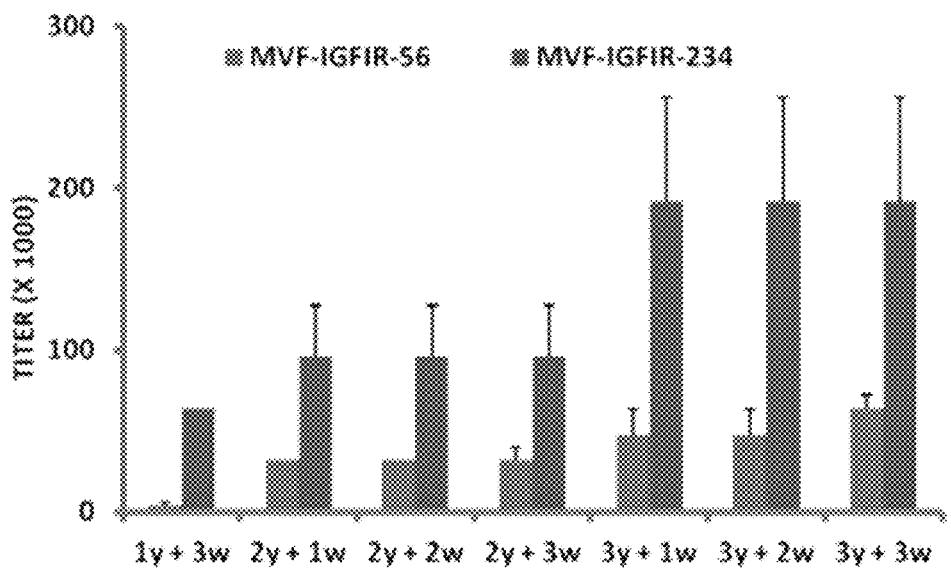
FIGS. 19 (A & B) contains graphs showing immunogenicity of MVF IGF-1R antibodies in rabbits. Antibody titers were defined as the reciprocal of the highest serum dilution that gives an absorbance of 0.2 after subtracting the preimmune data. 1y+3w represent blood drawn three weeks after the first immunization. 3y+3w represent blood drawn three weeks after the third immunization.
Figure 19B:
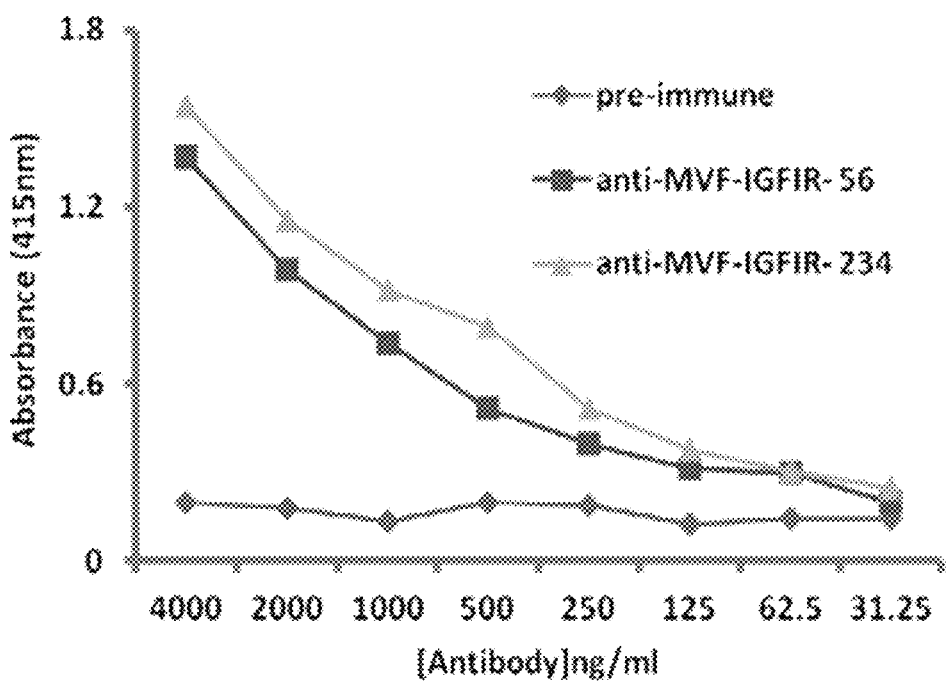

Immunogenicity of IGF-1R Peptide Vaccines in Rabbits and Cross-Reactivity of Vaccine Antibodies to Recombinant Human IGF-1R:

The immune response to each of the two chimeric peptide vaccines constructs were determined in outbred rabbits. The two B-cell epitopes that showed the best inhibitory effects in the proliferation assay (IGF-1R (56-81) and the IGF-1R (234-252)) were used for this assay and these epitopes were collinearly synthesized with the modified MVF-T helper epitope (SEQ ID NO:12) to produce the chimeric vaccine construct. The two vaccines construct elicited high amounts of antibodies with titers greater than 100,000 in most cases and the IGF-1R (234-252) epitope showed the best immunogenicity with very high antibody titers (FIGS. 19 A & B). Antibody titers increased after the booster immunization and were long lasting. This illustrates that the vaccine constructs were highly immunogenic and were able to establish immunological memory in the rabbits. The vaccine antibodies bound the rhIGF-1R as shown in the ELISA assay and the binding was very specific since dilution of antibodies caused a gradual decreased in binding and most importantly, the pre-immune sera antibodies showed no binding.

Figure 20A:
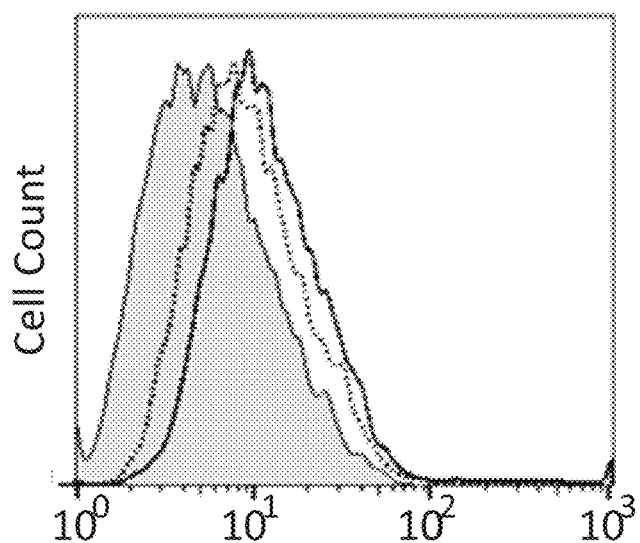
FIG. 20 (A-C) contains histograms showing the binding of MVF IGF-1R antibodies to cancer cells. Human cancer cell lines, SKOV-3 (A), Capan-2 (B) and HT-29 (C) were incubated with MVF IGF-1R antibodies and the extent of cell binding was evaluated by immunofluorescence flow cytometry. Preimmune is shown with gray fill, anti-MVF IGF-1R 56 is shown in solid line, and anti-MVF IGF-1R 234 is shown in dotted line. The x-axis shows FLH-1.
Figure 20B:
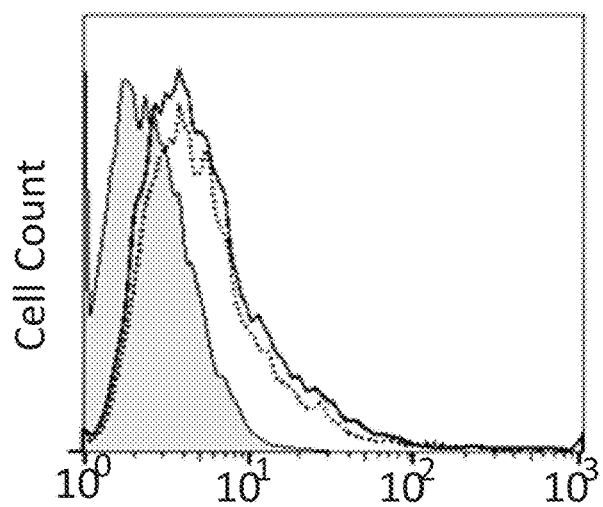
Figure 20C:
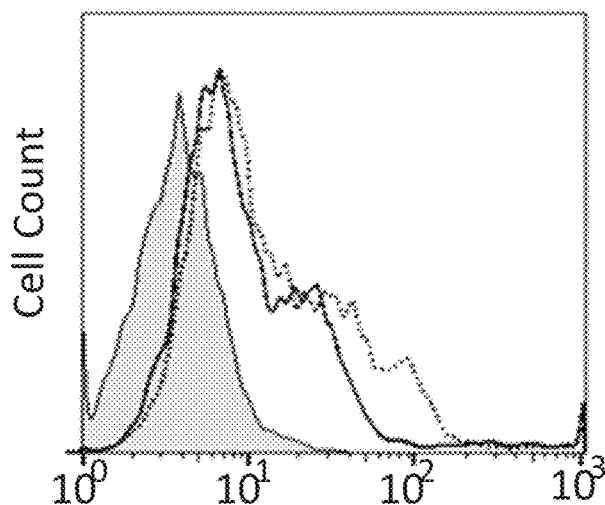
Figure 21A:
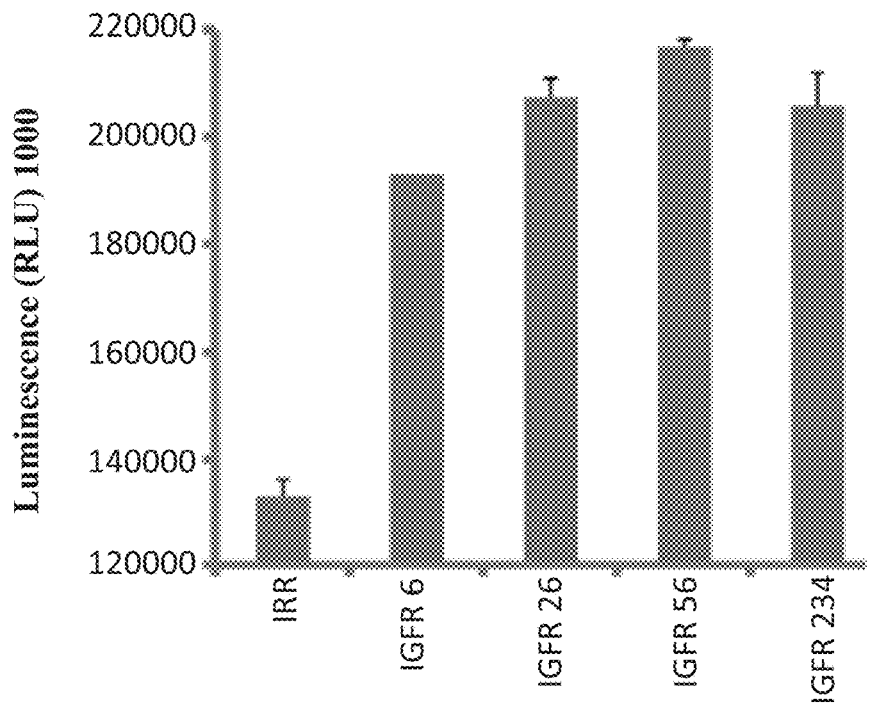
FIG. 21 (A-F) contains graphs showing induction of apoptosis by IGF-1R peptide mimics and MVF IGF-1R antibodies in three different cell lines: MCF-7 (A & D), JIMT-1 (B & E), Bx-PC3 (C & F). Apoptosis was evaluated by measuring caspase activity after treatment with IGF-1R chimeric peptides (A, B, C) and MVF IGF-1R antibodies (D, E, F) (150 µg/ml).
Figure 21B:
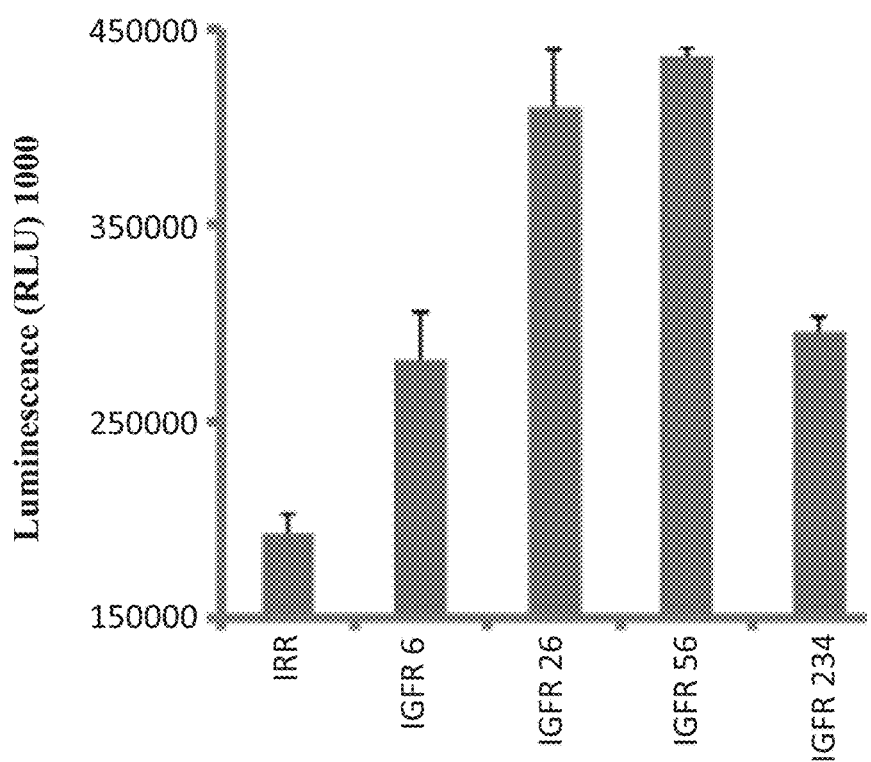
Figure 21C:
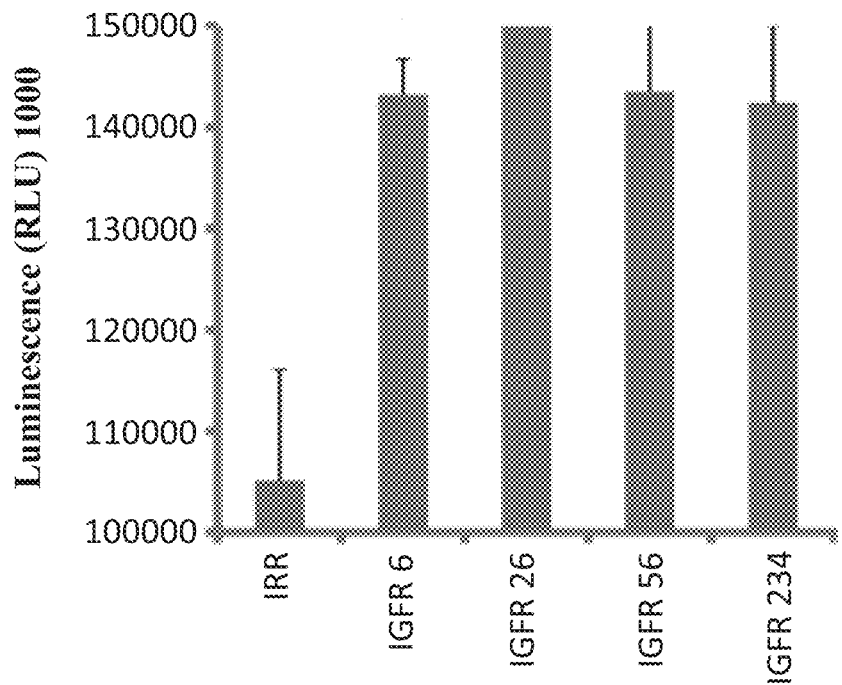
Figure 21D:
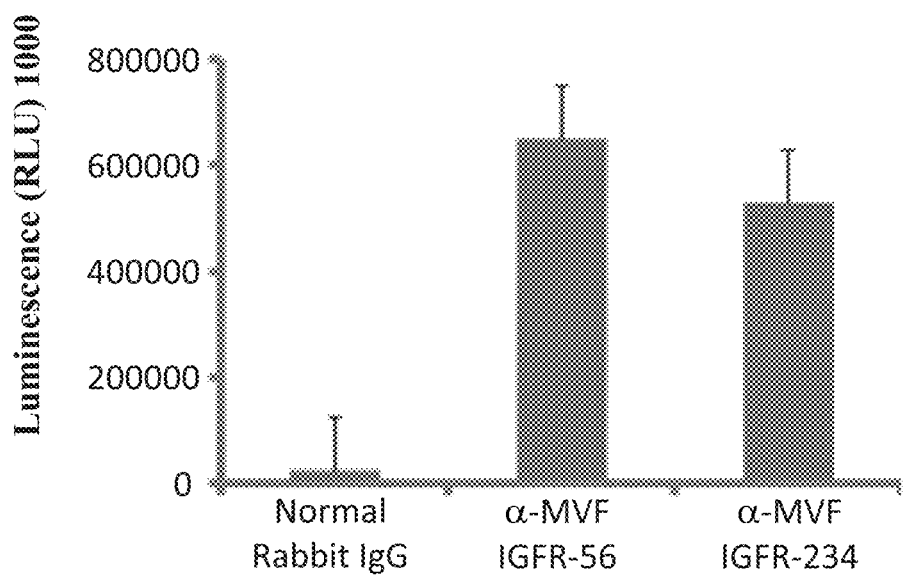
Figure 21E:
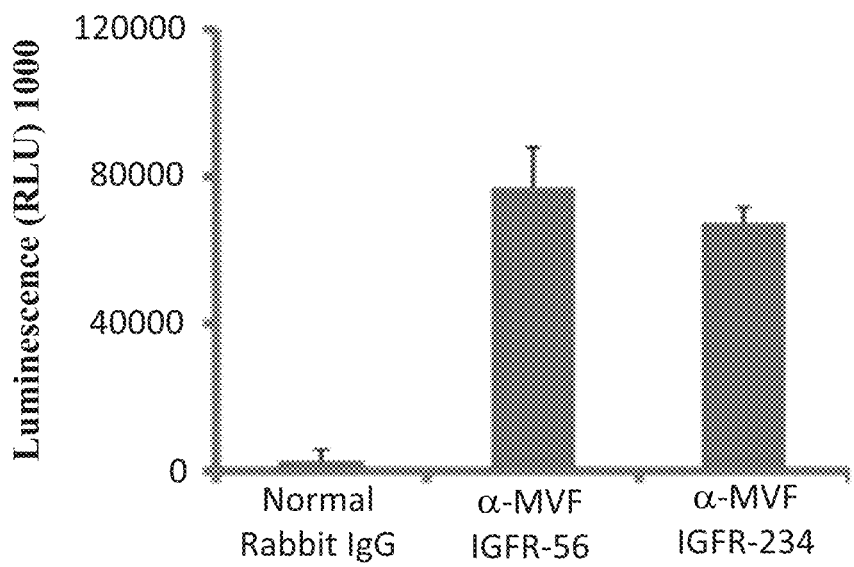
Figure 21F:
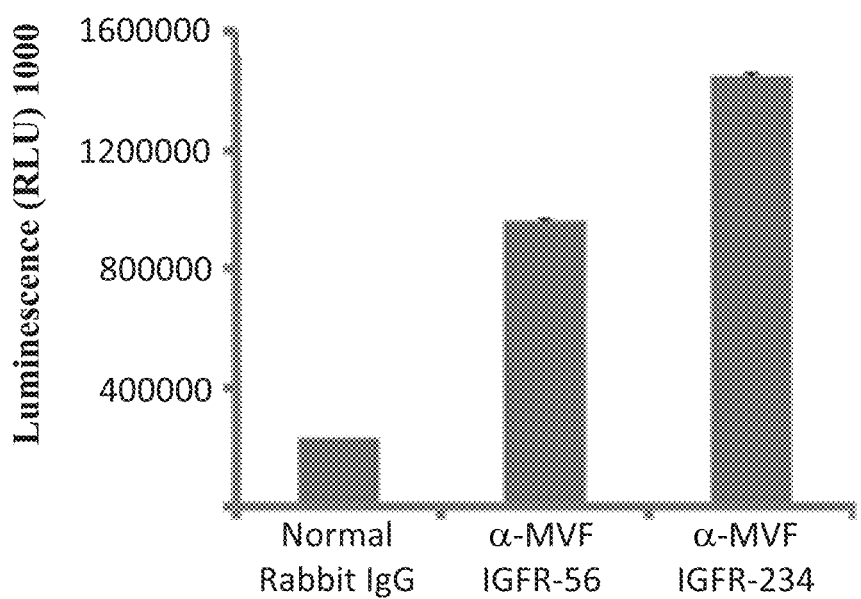
Figure 22A:
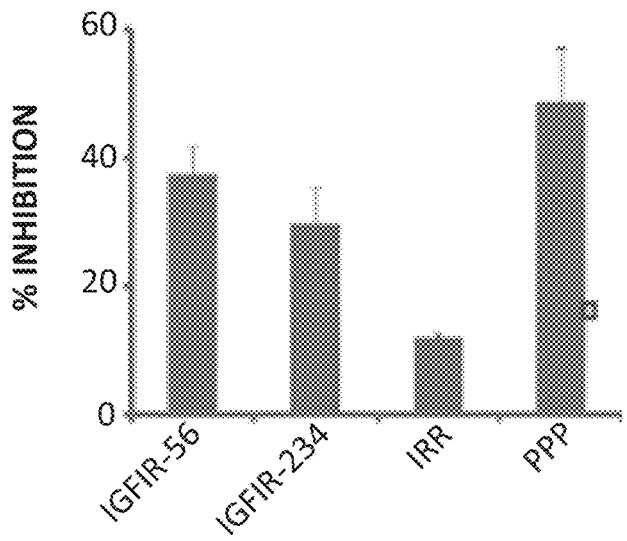
FIG. 22 (A-F) contains graphs showing inhibition of receptor phosphorylation in breast (MCF-7 (A & D) and JIMT-1 (B & E)) and pancreatic (BxPC-3 (C & F)) cancer cells following treatment with IGF-1R peptide mimics (A, B, C) and IGF-1R chimeric peptide antibodies (D, E, F). PPP is an IGF-1R TKI that was used as a positive control. NRIgG and IRR were used as negative controls.
Figure 22B:
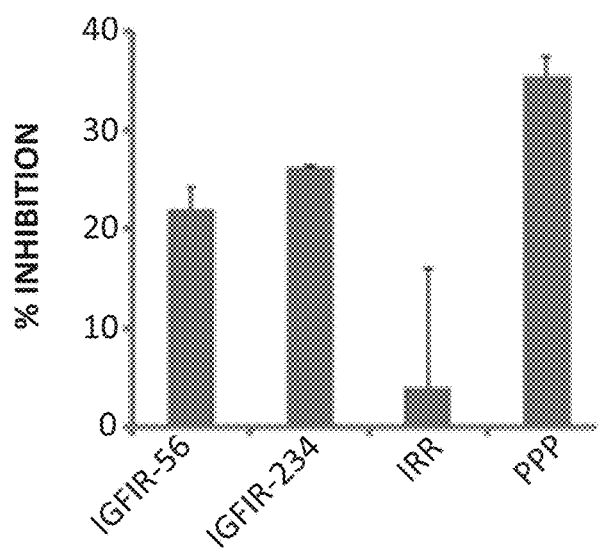
Figure 22C:
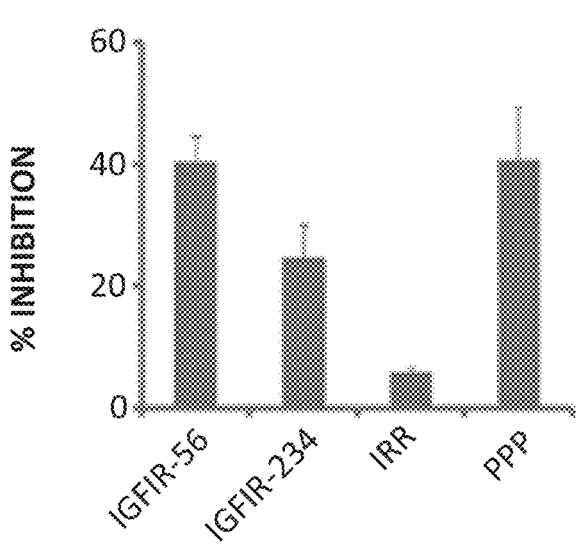
Figure 22D:
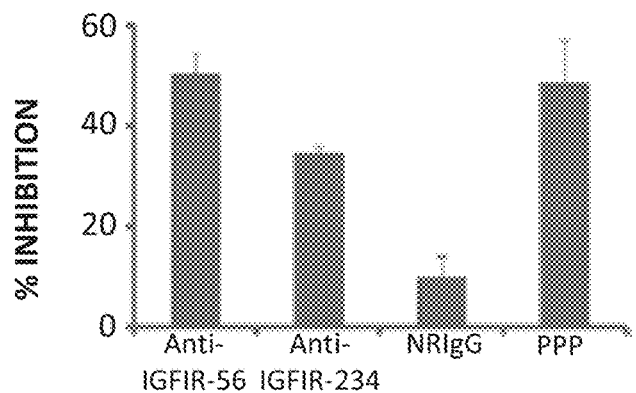
Figure 22E:
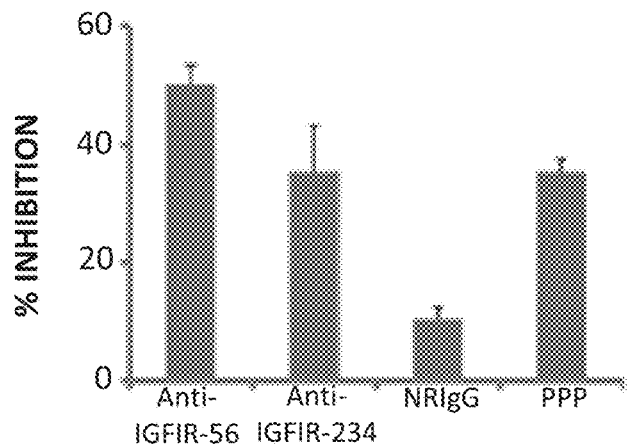
Figure 22F:
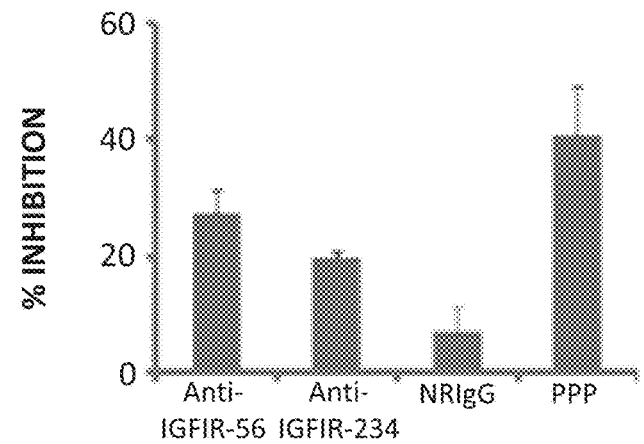

Cross-Reactivity of Vaccine Antibodies from the Rabbits to Bind and Recognize IGF-1R Expressing Cells in Flow Cytometry:

The ability of the vaccine antibodies to recognize the native IGF-1R receptor protein expressed on ovarian, pancreatic and colon cancer cells was evaluated. Immunofluorescence staining techniques were used to study the binding affinities. Antibodies generated to the IGF-1R (56-81) and the IGF-1R (234-252) vaccine constructs were evaluated and showed high binding capabilities to the cell lines while the pre immune antibodies showed no binding (FIG. 20 A-C).

Apoptosis Determination by Caspase Activity Assay:

Targeting key apoptotic regulatory mechanisms in cancer are a promising strategy for the development of improved therapeutic agents. It was demonstrated the IGF-1R chimeric peptides and vaccine antibodies will reduce signaling of IGF-1R which results in induction of apoptosis of cancer cells in vitro thereby causing cell death. This was accomplished using the caspase assay in breast and pancreatic cancer cells. Caspase activity after treatment was measured using the caspase Glo reagent and a luminometer. Increased levels of caspase 3 and 7 are indicative of apoptototic activity suggesting that the IGF-1R peptides/antibodies can function as inhibitors. Cancer cells (MCF-7, JIMT-1 and BxPC-3) in exponential growing phase were seeded in 96 well plates and the following day, the cells were treated with IGF-1R peptide mimics and peptide vaccine antibodies as inhibitors and incubated for a day. After treatment, apoptosis was evaluated by measuring caspase 3/7 release using the Caspase-Glo reagent kit (Promega). Results obtained showed a significant increase in the amount of caspase activity in the treated cases when compared to the negative controls (irrelevant peptide and normal rabbit IgG). Treatment caused more than a 10 fold increased in caspase release (FIG. 21 A-F), which is indicative of increased apoptosis. FIG. 21 A-C is treatment with peptide mimics whereas FIG. 21 D-F is treatment with peptide vaccine antibodies.

Downregulation of IGF-1R and Receptors Phosphorylation by IGF-IR Peptide Mimics and Anti-Peptide Antibodies:

Signaling through these receptors results in activation of downstream proteins like MAPK, pAKT and also increased expression and phosphorylation of the receptors. It was demonstrated that the chimeric peptides and vaccine antibodies (IGF-R1 (56-81) and IGF-1R (234-252)) were able to downregulate the expression of phosphorylated IGF-1R on the surface of cancer cells. The effects of chimeric peptides and antipeptide antibodies on IGF-1 signaling in MCF-7, JIMT-1 and BxPC-3 cells were analyzed using protein lysates after treatment and measurement of phosphorylated levels of the receptors in a sandwich ELISA method using Human-phospho-IGF-1R ELISA kit from R&D diagnostics. Treatment significantly inhibited receptor phosphorylation in all three cell lines indicating that the peptide mimics and peptide vaccine antibodies were able to prevent ligand binding and activation of the receptor thereby inhibiting intracellular phosphorylation (FIG. 22 A-F). FIG. 22 A-C is treatment with peptide mimics and FIG. 22-D-F is treatment with peptide vaccine antibodies.

Figure 23A:
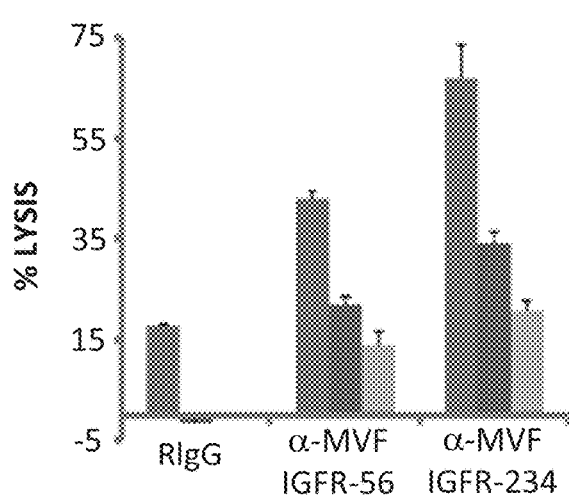
FIG. 23 (A-C) contains graphs showing that IGF-1R chimeric peptide antibodies induce ADCC of cancer cells. Target cells BxPC-3 (A), MCF-7 (B), and JIMT-1 (C) were incubated with 100 µg of the antibodies and assayed in the presence of human PBMCs at an effector to target ratio of 100:1, 20:1 and 4:1 (shown left to right).
Figure 23B:
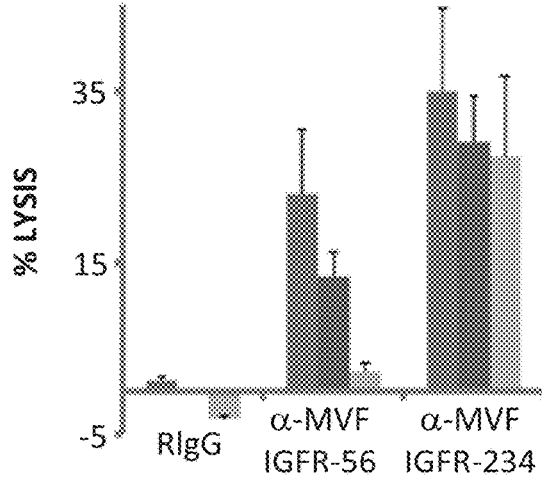
Figure 23C:
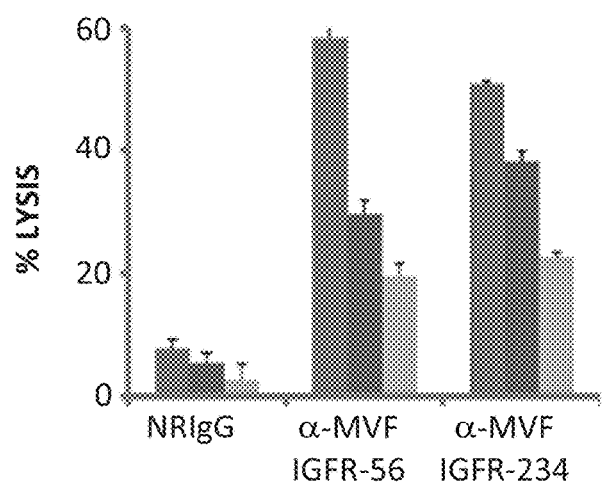
Figure 24A:
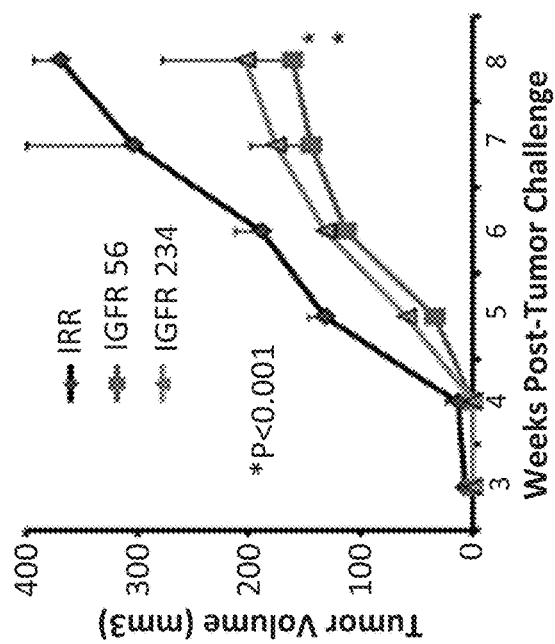
FIG. 24 (A-D) contains graphs showing the effects of IGF-1R chimeric peptides in Balb/c SCID transplantable mouse model of pancreatic (A & C) and breast (B & D) cancer. Mice at the age of 5-6 weeks were injected subcutaneously with BxPC-3 (A & C) and JIMT-1 (B & D) cells and treated with 200 μg of the chimeric peptides. Percentage tumor weight after treatment are shown and all treatments were statistically significant with P values <0.05.
Figure 24B:
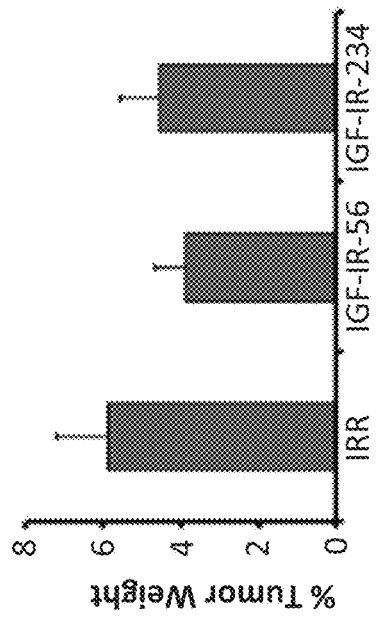
Figure 24C:
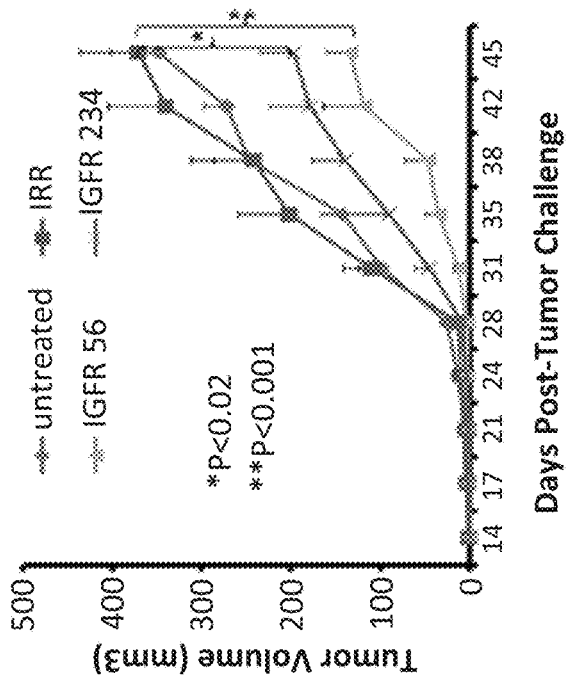
Figure 24D:
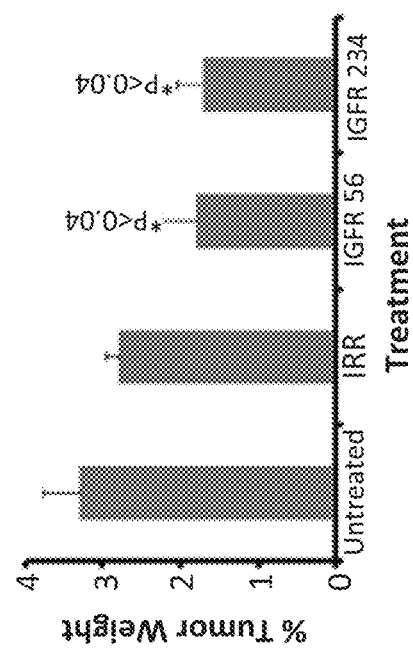

IGF-1R Anti-Peptide Antibody Causes ADCC of Cancer Cells:

One major mechanism of action of antibodies is to induce ADCC because the Fc regions are able to interact with PBMCs and attract them to specific targets. Accordingly, the ability of the IGF-1R antibodies to cause ADCC of cancer cells by inducing PBMCs to lyse target cancer cells was determined. IGF-1R peptide antibodies and effector PBMCs from normal human donors were used as previously described [Kaumaya P. T., et al. 2009. Journal of Clinical Oncology 27(31):5270-5277] with MCF-7, JIMT-1 and BxPC-3 cells as target cells. ADCC was measured using a biolouminescence cytotoxicity assay kit (aCella-TOX™). FIG. 23 A-C shows increased lysis following treatment with IGF-1R anti-peptide antibodies (IGF-1R (56-81) and IGF-1R (234-252)) and that the effects increased with greater effector to target ratio. These results indicate that the IGF-1R anti-peptide antibodies are able to stimulate human PBMCs to cause cancer cell death which is a major mode of action of antibodies. Three different effectors to target ratios were used and the results show that the antibodies were able to cause ADCC by inducing lysis of the target cells. The effects were greater when an effector to target ratio of 100:1 was used.

Therapy with IGF-1R Peptide Mimics Prevents Breast and Pancreatic Tumor Growth In Vivo in a Transplantable Cancer Mouse Model:

To test the in vivo effects of the chimeric peptides, a transplantable breast and pancreatic mouse model was used. BxPC-3 pancreatic and JIMT-1 breast cancer cells were injected subcutaneously into the flanks of SCID mice. After tumor challenge, the mice were treated intravenously with the IGF-1R peptide mimics starting at day zero (day of tumor challenge) and weekly for a total of 7 weeks. Tumor growth was monitored twice weekly and at the end of treatment, all mice were euthanized and the tumors extracted and weighed and the percentage tumor weight calculated. The results are shown in FIG. 24 (A-D) and demonstrate that both IGF-1R (56-81) and IGF-1R (234-252) peptides significantly decreased the percentage tumor weight.

Example 5

Figure 25A:
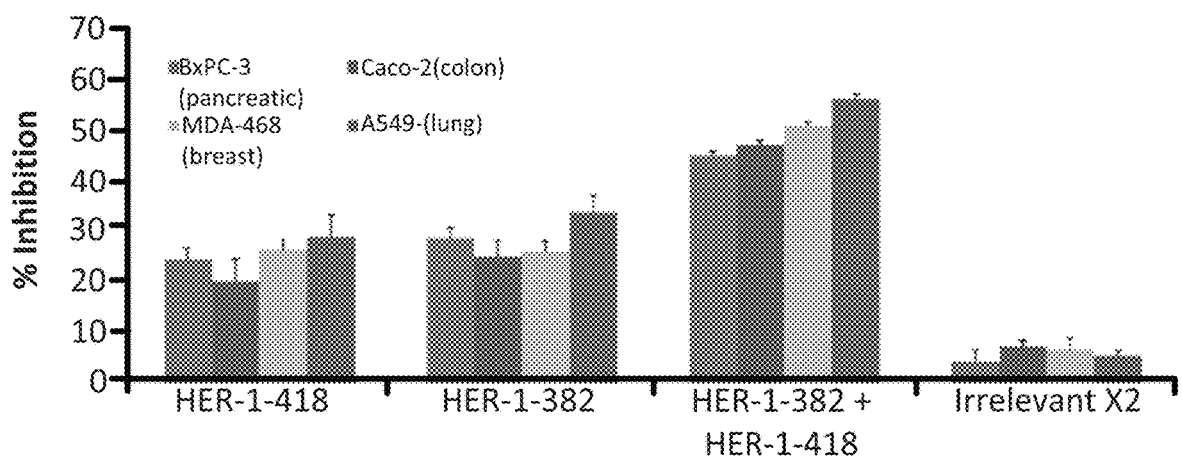
FIGS. 25 (A & B) contains graphs showing (A) the results of a MTT proliferation assay using combination treatment with HER-1 epitopes as inhibitors in colon (10,000/well), breast (5000/well), lung (4000/well) and pancreatic (4000/well) cancer cells in a 96-well plate; and (B) receptor phosphorylation as measured using human phosphor-EGFR ELISA kits. Each inhibitor was used at a concentration of 200 μg that was determined after a dose dependent titration from 12.5 μg-200 μg.
Figure 25B:
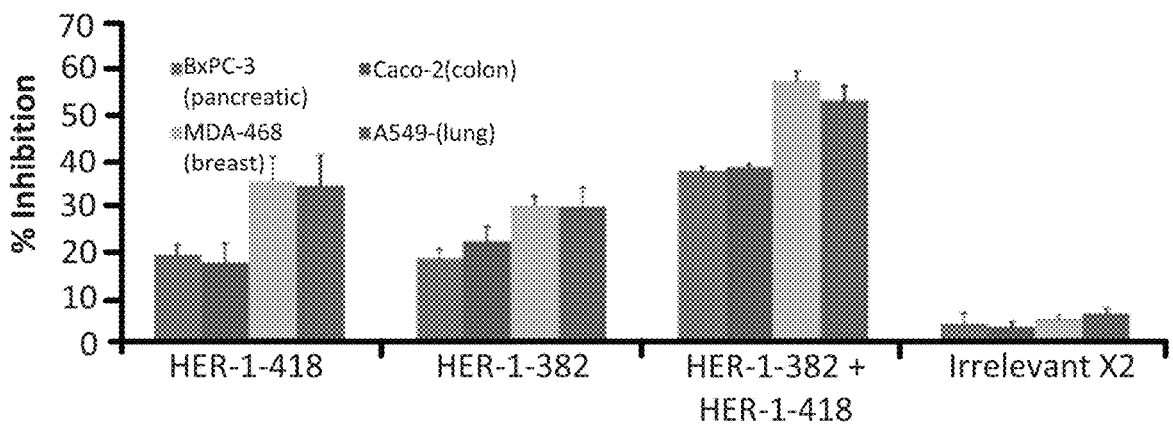

Combination Treatments of HER-1, HER-3, IGF-1R and HER-2 Peptide Vaccines and Chimeric Peptides Provide Synergistic Results HER-1 Epitope Combination Treatment Results:

The above Examples indicate that both HER-1 (382-410) and HER-1 (418-435) epitopes prevented tumor growth in vivo in the FVB/n model and similarly reduced the amount of proliferating cells and microvascular density. Accordingly, the effects of combination treatment with these two novel HER-1 epitopes on the proliferation and phosphorylation of breast, lung, pancreatic and colon cancer cell lines was evaluated. Single treatments inhibited these key signaling pathways but a combination approach involving the two peptide epitopes HER-1 (382-410) and HER-1 (418-435) caused significantly higher inhibition. Results are shown in FIG. 25, which illustrates that targeting two different parts of the receptors can increase inhibition rates.

Figure 26A:
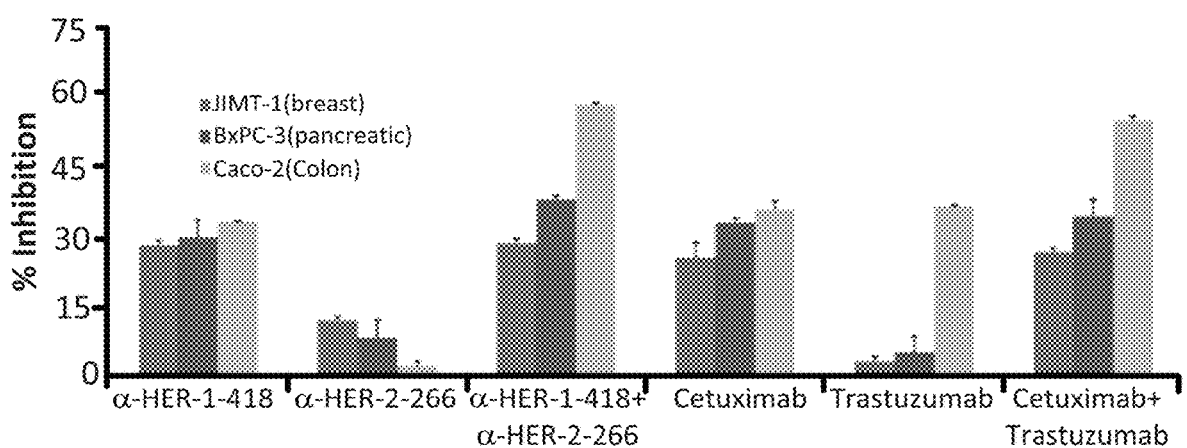
FIG. 26 (A-C) contains graphs showing (A) the results of a MTT proliferation assay using combination treatment with HER-1 and HER-2 antibodies as inhibitors in colon (10,000/well), breast (5000/well for MCF-7 and 4000/well for JIMT-1), and pancreatic (4000/well) cancer cells in a 96-well plate; and (B & C) receptor phosphorylation as measured using human phospho-EGFR/HER-2 ELISA kits. Each inhibitor was used at a concentration of 200 μg that was determined after a dose dependent titration from 12.5 μg-200 μg.
Figure 26B:
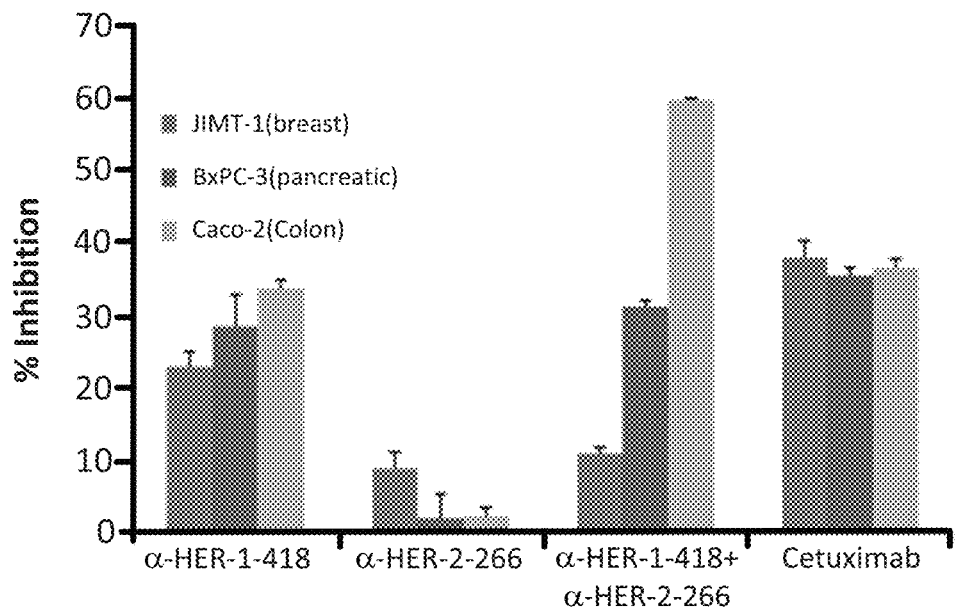
Figure 26C:
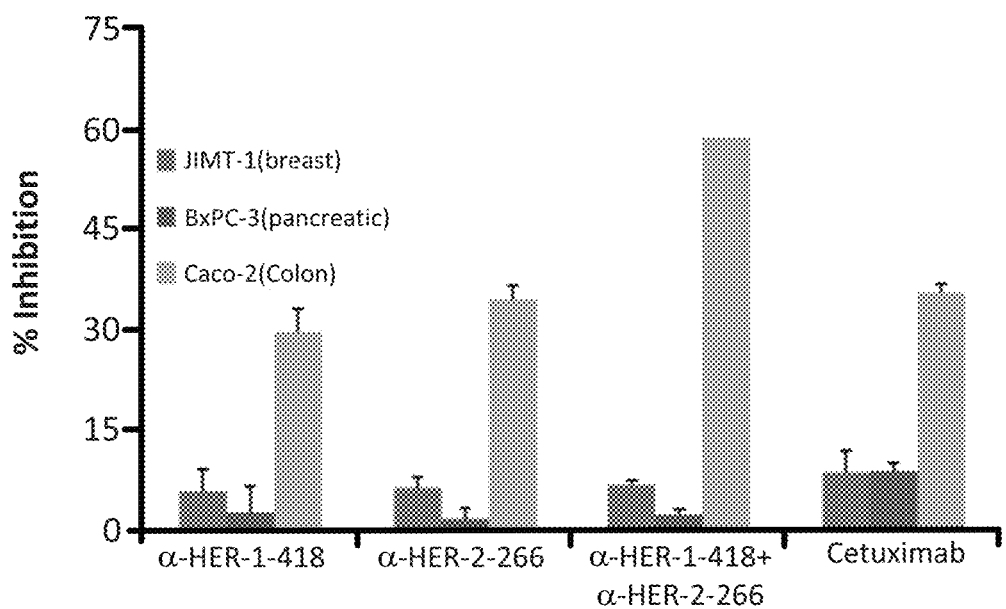

HER-1/HER-2 Anti-Peptide Antibody Combination Treatment Results:

Combination treatment with HER-1 and HER-2 peptide vaccine antibodies showed greater inhibition of in vitro proliferation and phosphorylation of breast, pancreatic and colon cancer cells. In FIG. 26 A, the effects of combination treatment with HER-1 and HER-2 antipeptide vaccine antibodies in three different cell lines are shown: (i) JIMT-1 trastuzumab resistant breast cell line (ii) BxPC-3 pancreatic and (iii) Caco-2 colon cells. Single treatments were able to cause inhibition of proliferation but combination treatment caused a greater inhibition of proliferation. The results were most significant in the Caco-2 colon cells and this is because the cells express relatively high levels of HER-1 and HER-2. The BxPC-3 and JIMT-1 cells are low expressing HER-2 cell lines with normal HER-1 expression and this explains why the combination effects were less significant trastuzumab. A HER-2 monoclonal-antibody also showed no anti-proliferative effects on JIMT-1 and BxPC-3 due to their low HER-2 expression. FIGS. 26 (B & C) show phosphorylated levels of HER-1 and HER-2 following treatment with both HER-1 and HER-2 peptide vaccine antibodies. Single treatment caused significant inhibition while combination treatment caused an even greater inhibition and this was most significant in the Caco-2 cells with high HER-1 and HER-2 expression.

Figure 27A:
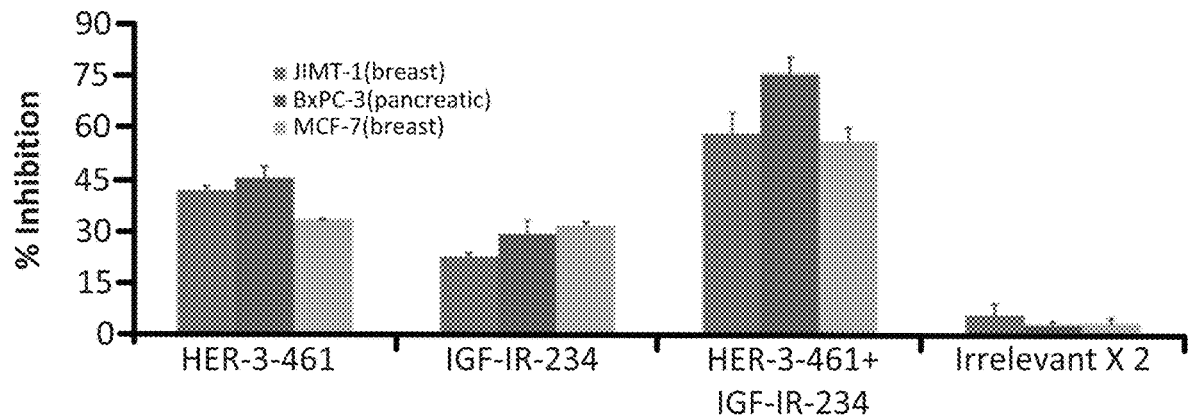
FIG. 27 (A-C) contains graphs showing (A) the results of a MTT proliferation assay using combination treatment with HER-3 and IGF-1R epitopes as inhibitors in colon (10,000/well), breast (5000/well for MCF-7 and 4000/well for JIMT-1), and pancreatic (4000/well) cancer cells in a 96-well plate; and (B & C) receptor phosphorylation as measured using human phospho-HER-3/IGF-1R ELISA kits. Each inhibitor was used at a concentration of 200 μg that was determined after a dose dependent titration from 12.5 μg-200 μg.
Figure 27B:
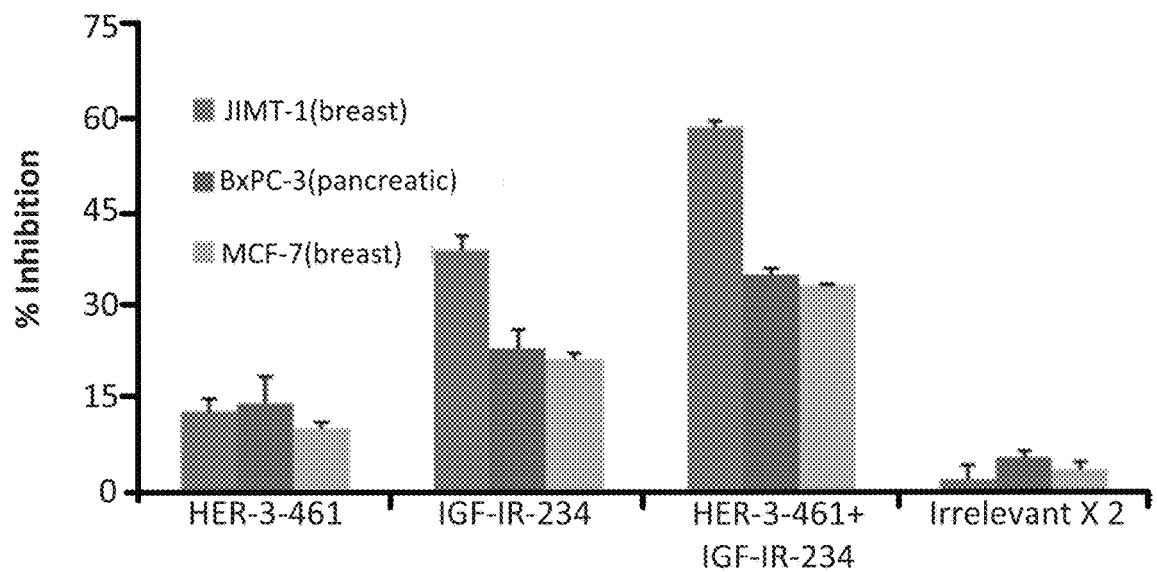
Figure 27C:
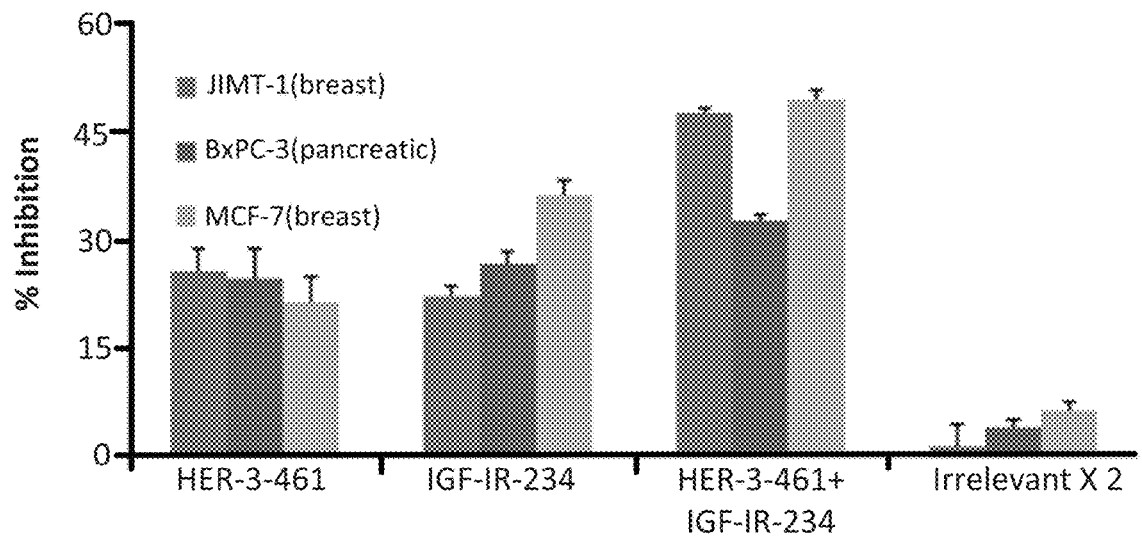

IGF-1R/HER-3 Epitope Combination Treatment Results:

The effects of epitopes on IGF-1 and HRG signaling in MCF-7, JIMT-1 and BxPC-3 cells were also evaluated where protein lysates after treatment was used to measure phosphorylated levels of the receptors in a sandwich ELISA method using Human-phospho-HER-3/IGF-IR ELISA kit from R&D diagnostics. Results in FIG. 27 A show that combination treatment in three different cell lines (two breast and one pancreatic) caused an increase in inhibition of proliferation (<60%) to either single treatment (35%). In FIGS. 27 (B & C), the effects of combination treatment on receptor phosphorylation were markedly increased compared to individual treatments. Overall, the results points to the potential benefits of targeting HER-3 and IGF-IR combinations in cancers that express these receptors.

Figure 28A:
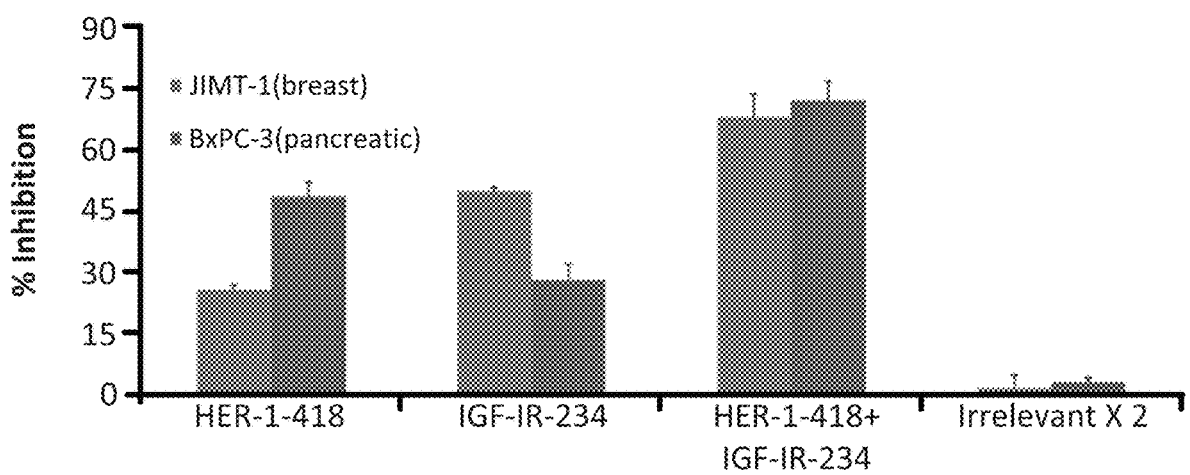
FIG. 28 (A-C) contains graphs showing (A) the results of a MTT proliferation assay using combination treatment with HER-1 and IGF-1R epitopes as inhibitors in breast (5000/well) and pancreatic (4000/well) cancer cells in a 96-well plate; and (B & C) receptor phosphorylation as measured using human phospho-HER-1/IGF-1R ELISA kits. Each inhibitor was used at a concentration of 200 μg that was determined after a dose dependent titration from 12.5 μg-200 μg.
Figure 28B:
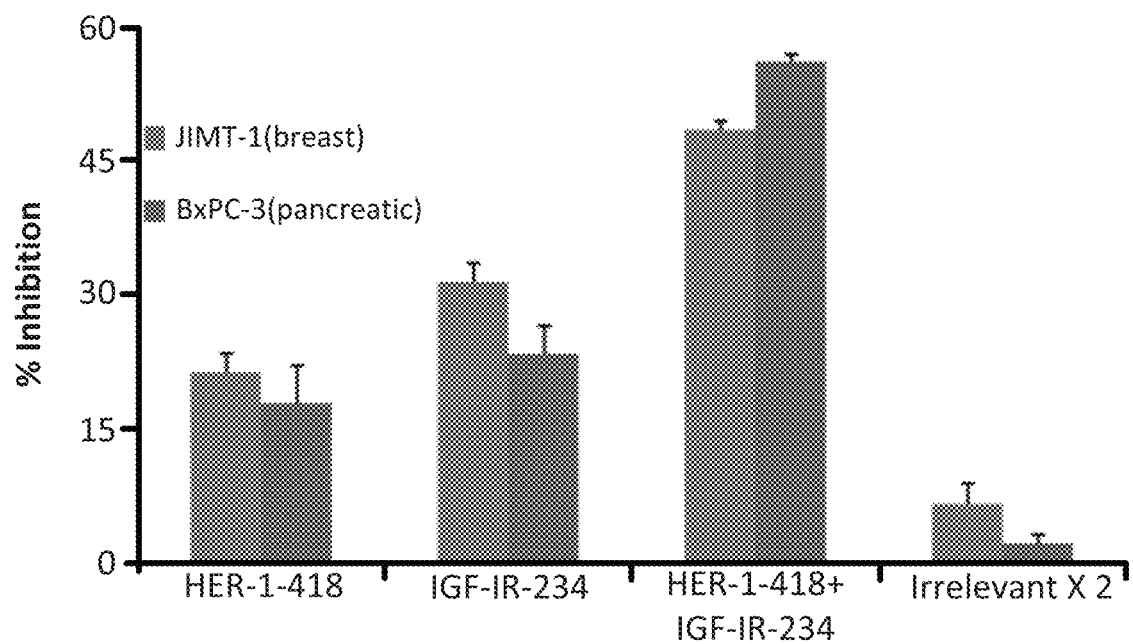
Figure 28C:
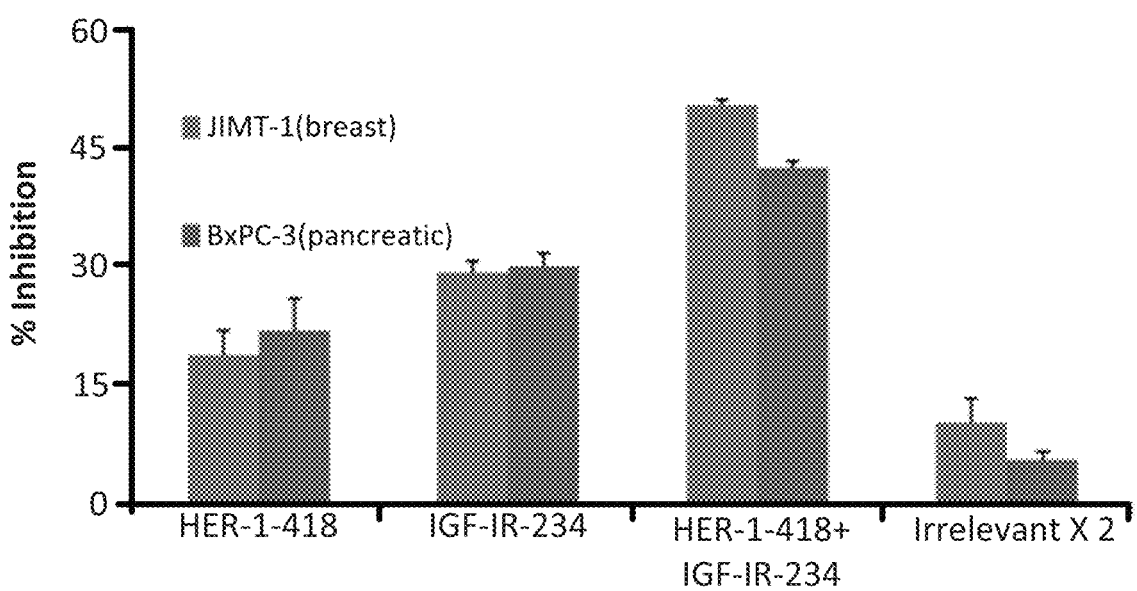
Figure 29A:
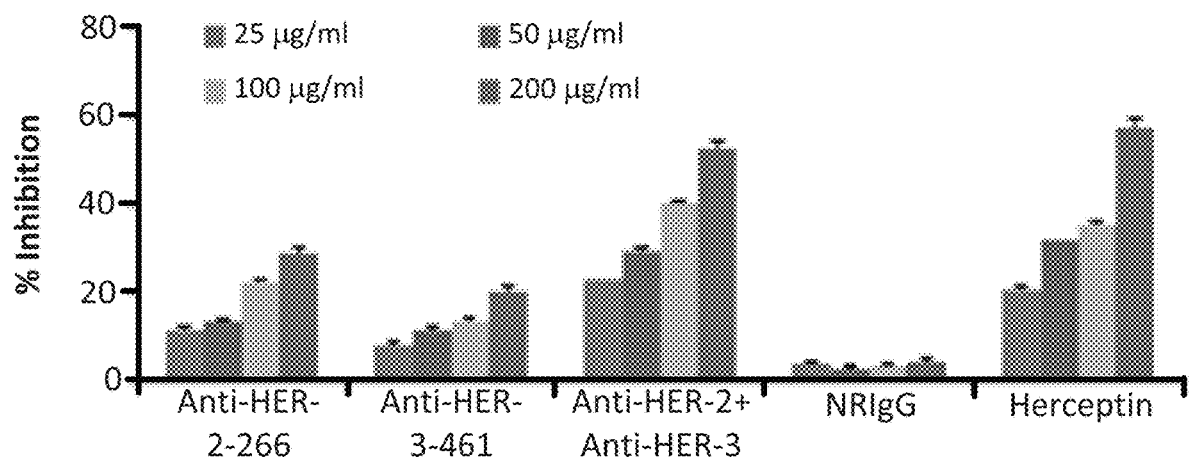
FIG. 29 (A-F) contains graphs showing (A, C & E) the results of a MTT proliferation assay using combination treatment with HER-2 and HER-3 antibodies as inhibitors in breast (10,000/well), pancreatic (5000/well) and colon (4000/well) cancer cells in a 96-well plate. Antibodies were used at increasing concentrations as shown and Herceptin was used as a positive control. (B, D & F) show receptor phosphorylation as measured using human phospho-HER-2/HER-3 ELISA kits. Each inhibitor was used at a concentration of 200 μg that was determined after a dose dependent titration from 12.5 μg-200 μg.
Figure 29B:
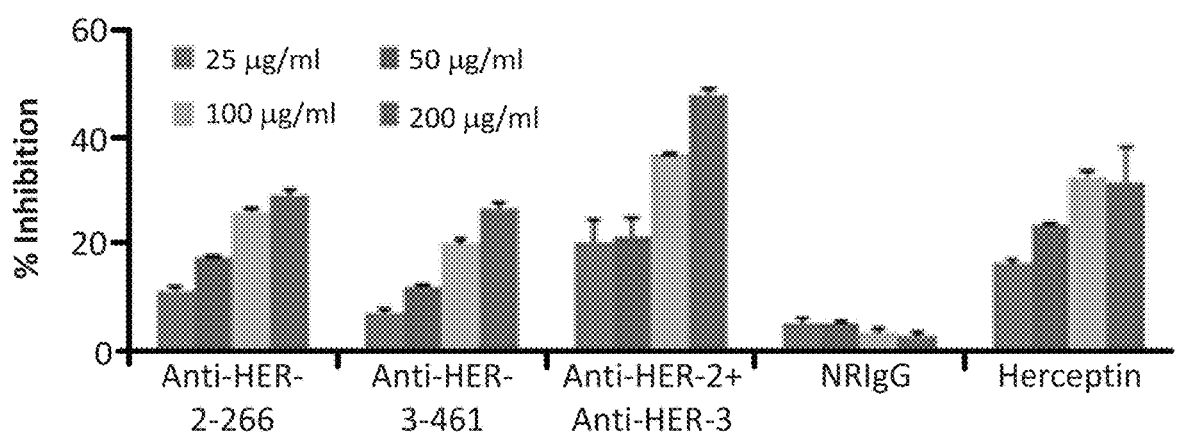
Figure 29C:
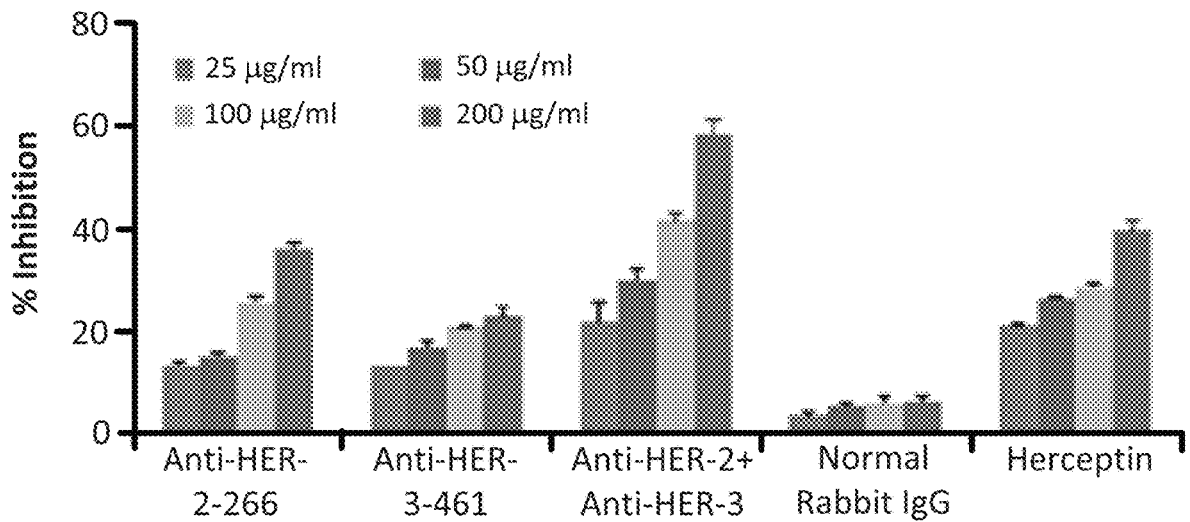
Figure 29D:
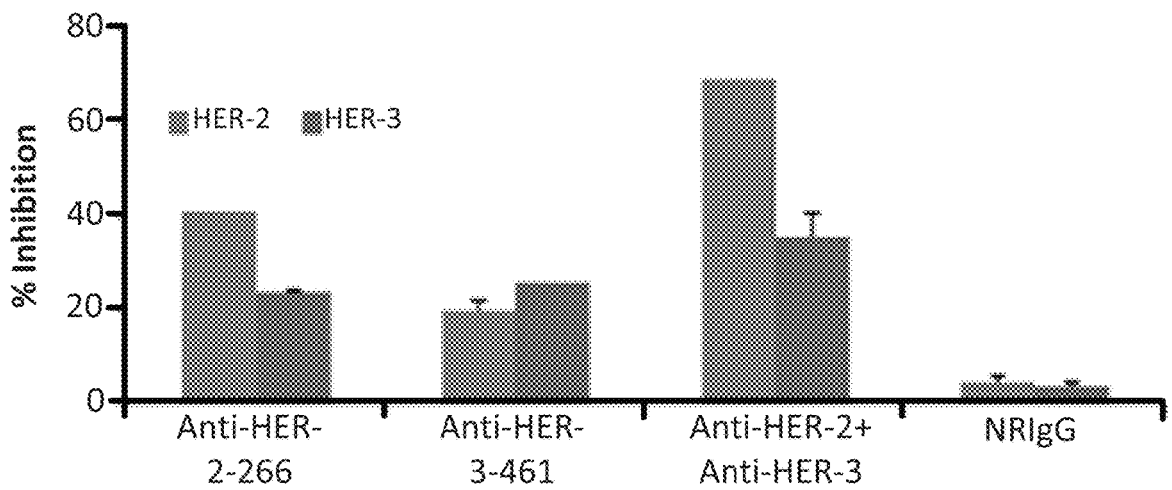
Figure 29E:
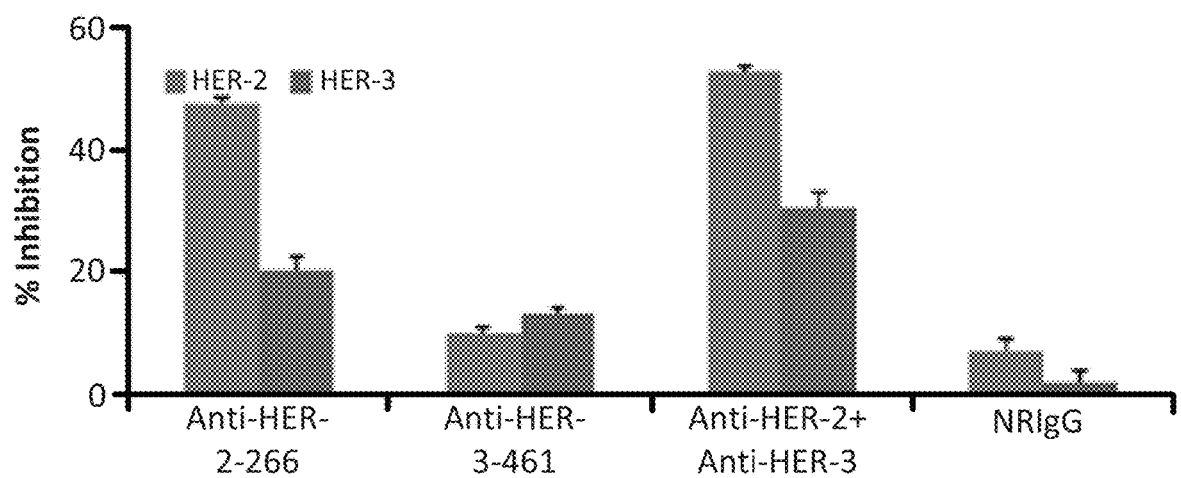
Figure 29F:
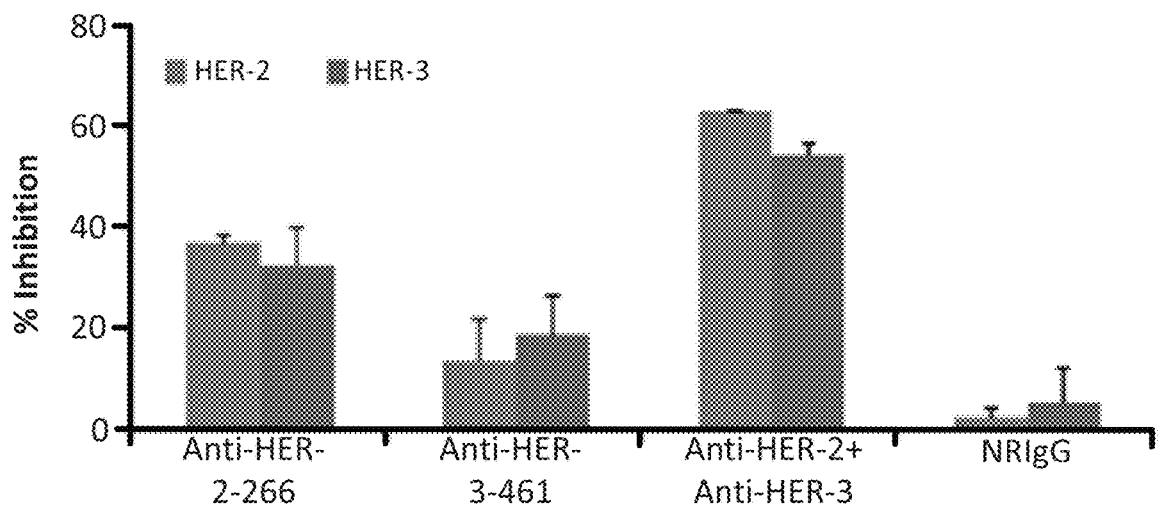

IGF-1R/HER-1 Epitope Combination Treatment Results:

Results in FIG. 28 show the effects of combination treatment with HER-1 and IGF-IR epitopes on two cell lines that have relatively high IGF-IR and HER-1 expression. The results in FIG. 28 validate the hypothesis that combined treatment with epitopes of HER-1 and IGF-1R are far superior to individual treatment in inhibition of proliferation and HER-1 and/or IGF-1R phosphorylation. These preliminary results indicate that targeting two relevant signaling pathways will be beneficial in future therapies of breast and pancreatic cancers.

HER-2/HER-3 Anti-Peptide Antibody Combination Treatment Results:

Results in FIG. 29 Panel A show that combination treatment with HER-2 and HER-3 peptide vaccine antibodies in three different cell lines, BT-474 breast cancer cell line, Capan-2 pancreatic and HT-29 colon cells caused an increased rate of inhibition of proliferation versus single treatments. Similarly, as shown in Panel B, phosphorylated levels of HER-2 and HER-3 following combined treatment with both HER-2 and HER-3 peptide antibodies caused enhanced inhibition of phosphorylation as compared to individual treatment. Significant inhibition was achieved in the BT-474 breast cancer cell which has high HER-2 and HER-3 over-expression. Overall, the results points to the benefits of a combination approach targeting HER-3 and HER-2 in breast, pancreatic and colon cancers.

I claim:

1. A HER-1 chimeric peptide for stimulating an immune response to a HER-1 protein comprising one or more HER-1 B cell epitopes, a T helper (Th) epitope, and a linker joining the HER-1 B cell epitope to the Th epitope, wherein:
   a. the one or more HER-1 B cell epitopes consist of a sequence selected from the group consisting of: SEQ ID NO: 1, SEQ ID NO: 2, and SEQ ID NO: 3;
   b. the Th epitope comprises a sequence selected from the group consisting of: SEQ ID NO: 12, SEQ ID NO:13, SEQ ID NO: 14, SEQ ID NO: 15, SEQ ID NO: 16 SEQ ID NO: 17, SEQ ID NO: 18, and SEQ ID NO:19; and
   c. the linker comprises a sequence that is from 1 to 15 amino acids in length.

2. The chimeric peptide of claim 1, wherein the Th epitope comprises SEQ ID NO:12.

3. The chimeric peptide of claim 1, wherein the linker comprises SEQ ID NO:20.

4. The chimeric peptide of claim 2, wherein the HER-1 B cell epitope consists of SEQ ID NO:3.

5. An IGF-1R chimeric peptide for stimulating an immune response to an IGF-1R protein comprising one or more IGF-1R B cell epitopes, a T helper (Th) epitope, and a linker joining the IGF-1R B cell epitope to the Th epitope, wherein:
   a. the one or more IGF-1R B cell epitopes consist of a sequence selected from the group consisting of SEQ ID NO:8, SEQ ID NO:9, SEQ ID NO:10, and SEQ ID NO:11;
   b. the Th epitope comprises a sequence selected from the group consisting of: SEQ ID NO: 12, SEQ ID NO:13, SEQ ID NO: 14, SEQ ID NO: 15, SEQ ID NO: 16 SEQ ID NO: 17, SEQ ID NO: 18, and SEQ ID NO:19; and
   c. the linker comprises a sequence that is from 1 to 15 amino acids in length.

6. The chimeric peptide of claim 5, wherein the Th epitope comprises SEQ ID NO:12.

7. The chimeric peptide of claim 5, wherein the linker comprises SEQ ID NO:20.

8. The chimeric peptide of claim 6, wherein the IGF-1R B cell epitope consists of SEQ ID NO:10 or SEQ ID NO:11.

* * * * *

```
                        SEQUENCE LISTING

<160> NUMBER OF SEQ ID NOS: 54

<210> SEQ ID NO 1
    <211> LENGTH: 28
    <212> TYPE: PRT
    <213> ORGANISM: Homo sapiens

<400> SEQUENCE: 1

Ile Leu Pro Val Ala Phe Arg Gly Asp Ser Phe Thr His Thr Pro Pro
    1               5                   10                  15

Leu Asp Pro Gln Glu Leu Asp Ile Leu Lys Thr Val
                20                  25

<210> SEQ ID NO 2
    <211> LENGTH: 29
    <212> TYPE: PRT
    <213> ORGANISM: Homo sapiens

<400> SEQUENCE: 2

Leu Ile Gln Ala Trp Pro Glu Asn Arg Thr Asp Leu His Ala Phe Glu
    1               5                   10                  15

Asn Leu Glu Ile Ile Arg Gly Arg Thr Lys Gln His Gly
                20                  25

<210> SEQ ID NO 3
    <211> LENGTH: 18
    <212> TYPE: PRT
    <213> ORGANISM: Homo sapiens

<400> SEQUENCE: 3

Ser Leu Asn Ile Thr Ser Leu Gly Leu Arg Ser Leu Lys Glu Ile Ser
    1               5                   10                  15

Asp Gly

<210> SEQ ID NO 4
    <211> LENGTH: 33
    <212> TYPE: PRT
    <213> ORGANISM: Homo sapiens

<400> SEQUENCE: 4

Val Pro Arg Cys Pro Gln Pro Leu Val Tyr Asn Lys Leu Thr Phe Gln
    1               5                   10                  15

Leu Glu Pro Asn Pro His Thr Lys Tyr Gln Tyr Gly Gly Val Cys Val
```

```
                20                  25                  30

Ala

<210> SEQ ID NO 5
<211> LENGTH: 19
<212> TYPE: PRT
<213> ORGANISM: Homo sapiens

<400> SEQUENCE: 5

Glu Arg Leu Asp Ile Lys His Asn Arg Pro Arg Arg Asp Cys Val Ala
1               5                   10                  15

Glu Gly Lys

<210> SEQ ID NO 6
<211> LENGTH: 24
<212> TYPE: PRT
<213> ORGANISM: Homo sapiens

<400> SEQUENCE: 6

Phe Val Met Leu Asn Tyr Asn Thr Asn Ser Ser His Ala Leu Arg Gln
1               5                   10                  15

Leu Arg Leu Thr Gln Leu Thr Glu
            20

<210> SEQ ID NO 7
<211> LENGTH: 23
<212> TYPE: PRT
<213> ORGANISM: Homo sapiens

<400> SEQUENCE: 7

Asp Thr Ile Asp Trp Arg Asp Ile Val Arg Asp Arg Asp Ala Glu Ile
1               5                   10                  15

Val Val Lys Asp Asn Gly Arg
            20

<210> SEQ ID NO 8
<211> LENGTH: 21
<212> TYPE: PRT
<213> ORGANISM: Homo sapiens

<400> SEQUENCE: 8

Gly Ile Asp Ile Arg Asn Asp Tyr Gln Gln Leu Lys Arg Leu Glu Asn
1               5                   10                  15

Cys Thr Val Ile Glu
            20

<210> SEQ ID NO 9
<211> LENGTH: 20
<212> TYPE: PRT
<213> ORGANISM: Homo sapiens

<400> SEQUENCE: 9

Glu Gly Tyr Leu His Ile Leu Leu Ile Ser Lys Ala Glu Asp Tyr Arg
1               5                   10                  15

Ser Tyr Arg Phe
            20

<210> SEQ ID NO 10
<211> LENGTH: 26
<212> TYPE: PRT
<213> ORGANISM: Homo sapiens
```

```
<400> SEQUENCE: 10

Leu Leu Phe Arg Val Ala Gly Leu Glu Ser Leu Gly Asp Leu Phe Pro
1               5                   10                  15

Asn Leu Thr Val Ile Arg Gly Trp Lys Leu
            20                  25

<210> SEQ ID NO 11
<211> LENGTH: 19
<212> TYPE: PRT
<213> ORGANISM: Homo sapiens

<400> SEQUENCE: 11

Ala Cys Pro Pro Asn Thr Tyr Arg Phe Glu Gly Trp Arg Cys Val Asp
1               5                   10                  15

Arg Asp Phe

<210> SEQ ID NO 12
<211> LENGTH: 18
<212> TYPE: PRT
<213> ORGANISM: Artificial
<220> FEATURE:
<223> OTHER INFORMATION: Artificial sequence based upon MVF peptide of
      measles virus

<400> SEQUENCE: 12

Lys Leu Leu Ser Leu Ile Lys Gly Val Ile Val His Arg Leu Glu Gly
1               5                   10                  15

Val Glu

<210> SEQ ID NO 13
<211> LENGTH: 19
<212> TYPE: PRT
<213> ORGANISM: Clostridium tetani

<400> SEQUENCE: 13

Asn Ser Val Asp Asp Ala Leu Ile Asn Ser Thr Ile Tyr Ser Tyr Phe
1               5                   10                  15

Pro Ser Val

<210> SEQ ID NO 14
<211> LENGTH: 17
<212> TYPE: PRT
<213> ORGANISM: Clostridium tetani

<400> SEQUENCE: 14

Pro Gly Ile Asn Gly Lys Ala Ile His Leu Val Asn Asn Gln Ser Ser
1               5                   10                  15

Glu

<210> SEQ ID NO 15
<211> LENGTH: 15
<212> TYPE: PRT
<213> ORGANISM: Clostridium tetani

<400> SEQUENCE: 15

Gln Tyr Ile Lys Ala Asn Ser Lys Phe Ile Gly Ile Thr Glu Leu
1               5                   10                  15

<210> SEQ ID NO 16
<211> LENGTH: 21
<212> TYPE: PRT
<213> ORGANISM: Clostridium tetani
```

```
<400> SEQUENCE: 16

Phe Asn Asn Phe Thr Val Ser Phe Trp Leu Arg Val Pro Lys Val Ser
1               5                   10                  15

Ala Ser His Leu Glu
            20

<210> SEQ ID NO 17
<211> LENGTH: 15
<212> TYPE: PRT
<213> ORGANISM: Measles virus

<400> SEQUENCE: 17

Leu Ser Glu Ile Lys Gly Val Ile Val His Arg Leu Glu Gly Val
1               5                   10                  15

<210> SEQ ID NO 18
<211> LENGTH: 15
<212> TYPE: PRT
<213> ORGANISM: Hepatitis B virus

<400> SEQUENCE: 18

Phe Phe Leu Leu Thr Arg Ile Leu Thr Ile Pro Gln Ser Leu Asn
1               5                   10                  15

<210> SEQ ID NO 19
<211> LENGTH: 20
<212> TYPE: PRT
<213> ORGANISM: Plasmodium vivax

<400> SEQUENCE: 19

Thr Cys Gly Val Gly Val Arg Val Arg Ser Arg Val Asn Ala Ala Asn
1               5                   10                  15

Lys Lys Pro Glu
            20

<210> SEQ ID NO 20
<211> LENGTH: 4
<212> TYPE: PRT
<213> ORGANISM: Artificial
<220> FEATURE:
<223> OTHER INFORMATION: Artificial linker sequence

<400> SEQUENCE: 20

Gly Pro Ser Leu
1

<210> SEQ ID NO 21
<211> LENGTH: 36
<212> TYPE: PRT
<213> ORGANISM: Homo sapiens

<400> SEQUENCE: 21

Cys His Pro Glu Cys Gln Pro Gln Asn Gly Ser Val Thr Cys Phe Gly
1               5                   10                  15

Pro Glu Ala Asp Gln Cys Val Ala Cys Ala His Tyr Lys Asp Pro Pro
            20                  25                  30

Phe Cys Val Ala
            35

<210> SEQ ID NO 22
<211> LENGTH: 14
<212> TYPE: PRT
```

<213> ORGANISM: Homo sapiens

<400> SEQUENCE: 22

Val Ala Cys Ala His Tyr Lys Asp Pro Pro Phe Cys Val Ala
1               5                   10

<210> SEQ ID NO 23
<211> LENGTH: 30
<212> TYPE: PRT
<213> ORGANISM: Homo sapiens

<400> SEQUENCE: 23

Val Ala Arg Cys Pro Ser Gly Val Lys Pro Asp Leu Ser Tyr Met Pro
1               5                   10                  15

Ile Trp Lys Phe Pro Asp Glu Glu Gly Ala Cys Gln Pro Leu
            20                  25                  30

<210> SEQ ID NO 24
<211> LENGTH: 14
<212> TYPE: PRT
<213> ORGANISM: Homo sapiens

<400> SEQUENCE: 24

Ile Trp Lys Phe Pro Asp Glu Glu Gly Ala Cys Gln Pro Leu
1               5                   10

<210> SEQ ID NO 25
<211> LENGTH: 31
<212> TYPE: PRT
<213> ORGANISM: Homo sapiens

<400> SEQUENCE: 25

Leu His Cys Pro Ala Leu Val Thr Tyr Asn Thr Asp Thr Phe Glu Ser
1               5                   10                  15

Met Pro Asn Pro Glu Gly Arg Tyr Thr Phe Gly Ala Ser Cys Val
            20                  25                  30

<210> SEQ ID NO 26
<211> LENGTH: 36
<212> TYPE: PRT
<213> ORGANISM: Homo sapiens

<400> SEQUENCE: 26

Ala Cys Pro Tyr Asn Tyr Leu Ser Thr Asp Val Gly Ser Cys Thr Leu
1               5                   10                  15

Val Cys Pro Leu His Asn Gln Glu Val Thr Ala Glu Asp Gly Thr Gln
            20                  25                  30

Arg Cys Glu Lys
        35

<210> SEQ ID NO 27
<211> LENGTH: 19
<212> TYPE: PRT
<213> ORGANISM: Homo sapiens

<400> SEQUENCE: 27

Cys Pro Leu His Asn Gln Glu Val Thr Ala Glu Asp Gly Thr Gln Arg
1               5                   10                  15

Cys Glu Lys

<210> SEQ ID NO 28
<211> LENGTH: 24

<212> TYPE: PRT
<213> ORGANISM: Homo sapiens

<400> SEQUENCE: 28

Cys Pro Ile Asn Cys Thr His Ser Cys Val Asp Leu Asp Asp Lys Gly
1               5                   10                  15

Cys Pro Ala Glu Gln Arg Ala Ser
            20

<210> SEQ ID NO 29
<211> LENGTH: 19
<212> TYPE: PRT
<213> ORGANISM: Homo sapiens

<400> SEQUENCE: 29

Thr Gly Thr Asp Met Lys Leu Arg Leu Pro Ala Ser Pro Glu Thr His
1               5                   10                  15

Leu Asp Met

<210> SEQ ID NO 30
<211> LENGTH: 22
<212> TYPE: PRT
<213> ORGANISM: Homo sapiens

<400> SEQUENCE: 30

Ala Val Leu Asp Asn Gly Asp Pro Leu Asn Asn Thr Thr Pro Val Thr
1               5                   10                  15

Gly Ala Ser Pro Gly Gly
            20

<210> SEQ ID NO 31
<211> LENGTH: 22
<212> TYPE: PRT
<213> ORGANISM: Homo sapiens

<400> SEQUENCE: 31

Leu Trp Lys Asp Ile Phe His Lys Asn Asn Gln Leu Ala Leu Thr Leu
1               5                   10                  15

Ile Asp Thr Asn Arg Ser
            20

<210> SEQ ID NO 32
<211> LENGTH: 35
<212> TYPE: PRT
<213> ORGANISM: Homo sapiens

<400> SEQUENCE: 32

Thr Leu Ile Asp Thr Asn Arg Ser Arg Ala Cys His Pro Cys Ser Pro
1               5                   10                  15

Met Cys Lys Gly Ser Arg Cys Trp Gly Glu Ser Ser Glu Asp Cys Gln
            20                  25                  30

Ser Leu Thr
        35

<210> SEQ ID NO 33
<211> LENGTH: 21
<212> TYPE: PRT
<213> ORGANISM: Homo sapiens

<400> SEQUENCE: 33

Ala Leu Val Thr Tyr Asn Thr Asp Thr Phe Glu Ser Met Pro Asn Pro
1               5                   10                  15

```
Glu Gly Arg Tyr Thr
            20

<210> SEQ ID NO 34
<211> LENGTH: 24
<212> TYPE: PRT
<213> ORGANISM: Homo sapiens

<400> SEQUENCE: 34

Pro Leu His Asn Gln Glu Val Thr Ala Glu Asp Gly Thr Gln Arg Ala
1               5                   10                  15

Glu Lys Cys Ser Lys Pro Cys Ala
            20

<210> SEQ ID NO 35
<211> LENGTH: 18
<212> TYPE: PRT
<213> ORGANISM: Homo sapiens

<400> SEQUENCE: 35

Pro Glu Ser Phe Asp Gly Asp Pro Ala Ser Asn Thr Ala Pro Leu Gln
1               5                   10                  15

Pro Glu

<210> SEQ ID NO 36
<211> LENGTH: 20
<212> TYPE: PRT
<213> ORGANISM: Homo sapiens

<400> SEQUENCE: 36

Leu Tyr Ile Ser Ala Trp Pro Asp Ser Leu Pro Asp Leu Ser Val Phe
1               5                   10                  15

Gln Asn Leu Gln
            20

<210> SEQ ID NO 37
<211> LENGTH: 19
<212> TYPE: PRT
<213> ORGANISM: Homo sapiens

<400> SEQUENCE: 37

Leu Phe Arg Asn Pro His Gln Ala Leu Leu His Thr Ala Asn Arg Pro
1               5                   10                  15

Glu Asp Glu

<210> SEQ ID NO 38
<211> LENGTH: 34
<212> TYPE: PRT
<213> ORGANISM: Homo sapiens

<400> SEQUENCE: 38

Cys Leu Pro Cys His Pro Glu Cys Gln Pro Gln Asn Gly Ser Val Thr
1               5                   10                  15

Cys Phe Gly Pro Glu Ala Asp Gln Cys Val Ala Cys Ala His Tyr Lys
            20                  25                  30

Asp Pro

<210> SEQ ID NO 39
<211> LENGTH: 18
<212> TYPE: PRT
<213> ORGANISM: Homo sapiens
```

```
<400> SEQUENCE: 39

Lys Pro Asp Leu Ser Tyr Met Pro Ile Trp Lys Phe Pro Asp Glu Glu
1               5                   10                  15

Gly Ala

<210> SEQ ID NO 40
<211> LENGTH: 20
<212> TYPE: PRT
<213> ORGANISM: Homo sapiens

<400> SEQUENCE: 40

Ile Asn Gly Thr His Ser Cys Val Asp Leu Asp Lys Gly Cys Pro
1               5                   10                  15

Ala Glu Gln Arg
            20

<210> SEQ ID NO 41
<211> LENGTH: 18
<212> TYPE: PRT
<213> ORGANISM: Homo sapiens

<400> SEQUENCE: 41

Leu Leu Ser Trp Val His Trp Ser Leu Ala Leu Leu Leu Tyr Leu His
1               5                   10                  15

His Ala

<210> SEQ ID NO 42
<211> LENGTH: 15
<212> TYPE: PRT
<213> ORGANISM: Homo sapiens

<400> SEQUENCE: 42

Ser Gln Ala Ala Pro Met Ala Glu Gly Gly Gly Gln Asn His His
1               5                   10                  15

<210> SEQ ID NO 43
<211> LENGTH: 21
<212> TYPE: PRT
<213> ORGANISM: Homo sapiens

<400> SEQUENCE: 43

Ser Cys Val Pro Leu Met Arg Cys Gly Gly Cys Ser Asn Asp Glu Gly
1               5                   10                  15

Leu Glu Cys Val Pro
            20

<210> SEQ ID NO 44
<211> LENGTH: 21
<212> TYPE: PRT
<213> ORGANISM: Homo sapiens

<400> SEQUENCE: 44

Ile Thr Met Gln Ile Met Arg Ile Lys Pro His Gln Gly Gln His Ile
1               5                   10                  15

Gly Glu Met Ser Phe
            20

<210> SEQ ID NO 45
<211> LENGTH: 22
<212> TYPE: PRT
<213> ORGANISM: Artificial Sequence
```

```
<220> FEATURE:
<223> OTHER INFORMATION: VEGF 102-122 mimic

<400> SEQUENCE: 45

Ile Thr Met Gln Cys Gly Ile His Gln Gly Gln His Pro Lys Ile Met
1               5                   10                  15

Ile Cys Glu Met Ser Phe
            20

<210> SEQ ID NO 46
<211> LENGTH: 23
<212> TYPE: PRT
<213> ORGANISM: Artificial Sequence
<220> FEATURE:
<223> OTHER INFORMATION: Modified L-amino acid VEGF sequence

<400> SEQUENCE: 46

Phe Ser Met Glu Cys Ile Met Arg Ile Lys Pro His Gln Gly Gln His
1               5                   10                  15

Ile Gly Cys Gln Met Thr Ile
            20

<210> SEQ ID NO 47
<211> LENGTH: 18
<212> TYPE: PRT
<213> ORGANISM: Homo sapiens

<400> SEQUENCE: 47

Asn Lys Cys Glu Cys Arg Pro Lys Lys Asp Arg Ala Arg Gln Glu Asn
1               5                   10                  15

Pro Cys

<210> SEQ ID NO 48
<211> LENGTH: 18
<212> TYPE: PRT
<213> ORGANISM: Homo sapiens

<400> SEQUENCE: 48

Lys Cys Glu Cys Arg Pro Lys Lys Asp Arg Ala Arg Gln Glu Asn Pro
1               5                   10                  15

Cys Gly

<210> SEQ ID NO 49
<211> LENGTH: 14
<212> TYPE: PRT
<213> ORGANISM: Homo sapiens

<400> SEQUENCE: 49

Lys Cys Ser Cys Lys Asn Thr His Ser Arg Cys Lys Ala Arg
1               5                   10

<210> SEQ ID NO 50
<211> LENGTH: 11
<212> TYPE: PRT
<213> ORGANISM: Homo sapiens

<400> SEQUENCE: 50

Thr Arg Val Ser Ile Met Leu Leu Leu Val Thr
1               5                   10

<210> SEQ ID NO 51
<211> LENGTH: 11
<212> TYPE: PRT
```

```
<213> ORGANISM: Homo sapiens

<400> SEQUENCE: 51

Gly Ala Cys Glu Arg Asp Val Gln Cys Gly Ala
1               5                   10

<210> SEQ ID NO 52
<211> LENGTH: 18
<212> TYPE: PRT
<213> ORGANISM: Homo sapiens

<400> SEQUENCE: 52

Cys Thr Pro Leu Gly Arg Glu Gly Glu Cys His Pro Gly Ser His
1               5                   10                  15

Lys Val

<210> SEQ ID NO 53
<211> LENGTH: 26
<212> TYPE: PRT
<213> ORGANISM: Homo sapiens

<400> SEQUENCE: 53

Cys Thr Pro Leu Gly Arg Glu Gly Glu Cys His Pro Gly Ser His
1               5                   10                  15

Lys Val Pro Phe Phe Arg Lys Arg Lys His
            20                  25

<210> SEQ ID NO 54
<211> LENGTH: 17
<212> TYPE: PRT
<213> ORGANISM: Homo sapiens

<400> SEQUENCE: 54

Cys Ser Arg Phe Pro Asp Gly Arg Tyr Arg Cys Ser Met Asp Leu Lys
1               5                   10                  15

Asn
```